(12) United States Patent
Powell et al.

(10) Patent No.: US 9,624,465 B2
(45) Date of Patent: Apr. 18, 2017

(54) COMPOSITIONS AND METHODS FOR COLLECTING ALGAE

(71) Applicant: University of Maryland Center for Environmental Science, Cambridge, MD (US)

(72) Inventors: Ryan J. Powell, Reisterstown, MD (US); Russell T. Hill, Baltimore, MD (US)

(73) Assignee: University of Maryland Center for Environmental Science, Cambridge, MD (US)

( * ) Notice: Subject to any disclaimer, the term of this patent is extended or adjusted under 35 U.S.C. 154(b) by 0 days.

(21) Appl. No.: 14/194,292

(22) Filed: Feb. 28, 2014

(65) Prior Publication Data
US 2014/0248680 A1 Sep. 4, 2014

Related U.S. Application Data

(60) Provisional application No. 61/770,390, filed on Feb. 28, 2013, provisional application No. 61/897,345, filed on Oct. 30, 2013, provisional application No. 61/915,594, filed on Dec. 13, 2013.

(51) Int. Cl.
| | | |
|---|---|---|
| *C12N 1/12* | (2006.01) | |
| *C12N 1/02* | (2006.01) | |
| *C12R 1/07* | (2006.01) | |
| *C12M 1/26* | (2006.01) | |
| *C12N 1/20* | (2006.01) | |

(52) U.S. Cl.
CPC ............... *C12N 1/12* (2013.01); *C12M 33/00* (2013.01); *C12N 1/02* (2013.01); *C12N 1/20* (2013.01); *C12R 1/07* (2013.01)

(58) Field of Classification Search
None
See application file for complete search history.

(56) References Cited

U.S. PATENT DOCUMENTS

2011/0263002 A1* 10/2011 Zhang et al. .............. 435/252.1

FOREIGN PATENT DOCUMENTS

| EP | 2546199 A1 | 1/2013 |
| WO | WO-2015066217 A1 | 5/2015 |

OTHER PUBLICATIONS

Biddy, M., et al., "Whole Algae Hydrothermal Liquefaction Technology Pathway," National Renewable Energy Laboratory(NREL) and Pacific Northwest National Laboratory (PNNL), Unites States (2013), Accessed at http://www.nrel.gov/docs/fy13osti/58051.pdf, accessed on Jul. 21, 2015.
Chisti, Y., "Biodiesel from Microalgae Beats Bioethanol," Trends in Biotechnology 26(3):126-131, Cell Press, United States (2008).
(Continued)

*Primary Examiner* — Louise W Humphrey
*Assistant Examiner* — Charles Zoltan Constantine
(74) *Attorney, Agent, or Firm* — Rubin and Rudman LLP; Judith U. Kim

(57) ABSTRACT

The invention relates to compositions containing *Bacillus* sp., optionally with magnetite, useful in methods for collecting algae. The invention also relates to methods for collecting algae by contacting algae and bare maghemite and compositions thereof.

8 Claims, 16 Drawing Sheets

(56) References Cited

OTHER PUBLICATIONS

Figure 1:
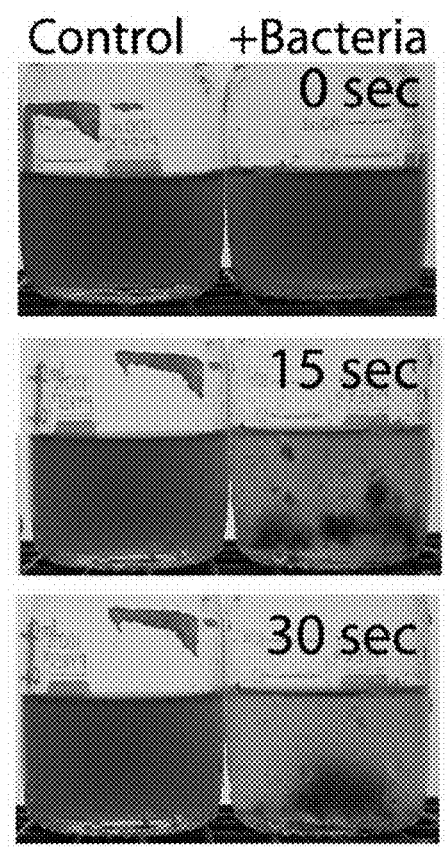

Divakaran, R. and Sivasankara Pillai, V.N., "Flocculation of Algae Using Chitosan," Journal of Applied Phycology 14:419-422, Kluwer Academic Publishers, Netherlands (2002).

Dubinsky, Z. and Rotem, J., "Relations Between Algal Populations and the pH of their Media," Oecologia 16(1):53-60, Springer-Verlag, Germany (1974).

Garrote, G.L., et al., "Lactobacilli Isolated from Kefir Grains: Evidence of the Presence of S-layer Proteins," Journal of Dairy Research 71(2):222-230, Proprietors of Journal of Dairy Research. England (2004).

Gärdes, A., "Diatom-Associated Bacteria are Required for Aggregation of Thalassiosira Weissflogii," The ISME Journal 5(3):436-445, International Society for Microbial Ecology, England (2011).

GenBank Accession No. KF015297, "Bacillus sp. RP1137 16S ribosomal RNA gene, partial sequence," (accessed at http://www.ncbi.nlm.nih.gov/nuccore/KF015297 accessed on Feb. 6, 2015), Accessed on Jul. 9, 2015, 2 pages.

Hermansson, M., "The DLVO Theory in Microbial Adhesion," Colloids and Surfaces B: Biointerfaces 14(1-4):105-119, Elsevier Science B.V., Netherlands (1999).

Hu, Y.R., et al., "Efficient Harvesting of Marine Microalgae Nannochloropsis Maritima Using Magnetic Nanoparticles," Bioresource Technology 138:387-390, Elsevier Science Pub. Co., England (2013).

International Search Report and Written Opinion for International Patent Application No. PCT/US2014/062968, International Searching Authority, Alexandria, Virginia, United States, mailed on Mar. 26, 2015, 11 pages.

Kamentsky, L., et al., "Improved Structure, Function and Compatibility for CellProfiler: Modular High-Throughput Image Analysis Software," Bioinforrnatics 27(8):1179-1180, Oxford University Press, England (2011).

Lavoie, A. and De La Noue, J., "Harvesting Microalgae with Chitosan," Journal of the World Mariculture Society 14(1-4):685-694, World Aquaculture society, United states (1983).

Lee, J., et al., "Microalgae-Associated Bacteria Play a Key Role in the Flocculation of Chlorella Vulgaris," Bioresource Technology 131:195-201, Elsevier Science Pub. Co., England (2013).

Lortal, S., et al., "S-Layer of Lactobacillus-Helveticus ATCC-12046: Isolation, Chemical Characterization and Reformation After Extraction with Lithium Chloride," Journal of General Microbiology 138:611-618, SGM, England (1992).

Marquis, R.E., et al., "Cation Exchange in Cell Walls of Gram-Positive Bacteria," Canadian Journal of Microbiology 22(7):975-982, Canadian Science Publishing, Canada (1976).

Nontembiso, P., et al., "Assessment of Bioflocculant Production by Bacillus sp. Gilbert, a Marine Bacterium Isolated from the Bottom Sediment of Algoa Bay," Marine Drugs 9(7):1232-1242, MDPI, Switzerland (2011).

Oh, H.M., et al., "Harvesting of Chlorella Vulgaris using a Bioflocculant from Paenibacillus sp. AM49," Biotechnology Letters 23:1229-1234, Kluwer Academic Publishers, Netherlands (2001).

Pal, M.K., et al., "Studies on the Conformation of and Metal Ion Binding by Teichoic Acid of *Staphylococcus aureus*," Biopolymers 30(3-4):273-277, Wiley, United States (1990).

Pavoni, J.L., et al., "Bacterial Exocellular Polymers and Biological Flocculation," Water Pollution Control Federation 44(3):414-429, Water Environment Federation, United States (1972).

Powell, R.J. and Hill, R.T., "Rapid Aggregation of Biofuel-Producing Algae by the Bacterium *Bacillus* sp. strain RP1137," Applied and Environmental Microbiology 79(19):6093-6101, American Society for Microbiology, United States (Oct. 2013).

Powell, R.J. and Hill, R.T., "Rapid Harvest of Microalgae Using a Novel Bacterial Isolate," was made on Jun. 13, 2012, during 2nd International Conference on Algal Biomass, Biofuels & Bioproducts, in San Diego.

Richardson, J.W., et al., "Economic Comparison of Open Pond Raceways to Photo Bio-Reactors for Profitable Production of Algae for Transportation Fuels in the Southwest," Algal Research 1(1):93-100, Elsevier B.V., Netherlands (2012).

Sabarth, N., et al., "Identification of Helicobacter Pylori Surface Proteins by Selective Proteinase K Digestion and Antibody Phage Display,"Journal of Microbiological Methods 62(3):345-349, Elsevier Biomedical, Netherlands (2005).

Schenk, P.M., et al., "Second Generation Biofuels: High-Efficiency Microalgae for Biodiesel Production," Bioengineering Research 1:20-43, Springer Science + Business Media, LLC, Germany (2008).

Schlesinger, A., et al., "Inexpensive Non-Toxic Flocculation of Microalgae Contradicts Theories; Overcoming a Major Hurdle to Bulk Algal Production," Biotechnology Advances 30(5):1023-1030, Elsevier Science, England (2012).

Sirin, S., et al., "Harvesting the Microalgae Phaeodactylum Tricornutum with Polyaluminum Chloride, Aluminium Sulphate, Chitosan and Alkalinity-Induced Flocculation," Journal of Applied Phycology 24(5):1067-1080, Springer Science + Business Media, LLC, Germany (2012).

Sobeck, D.C. and Higgins, M.J., "Examination of Three Theories for Mechanisms of Cation-Induced Bioflocculation," Water Research 36(3):527-38, Pergamon Press., England (2002).

Tang, J., et al., "Magnetite Fe3O4 Nanocrystals: Spectroscopic Observation of Aqueous Oxidation Kinetics," Journal of Physical Chemistry B 107:7501-7506, American Chemical Society, United states (2003).

Uduman, N., et al. "Dewatering of Microalgal Cultures: A Major Bottleneck to Algae-Based Fuels," Journal of Renewable Sustainable Energy 2:012701, American Institute of Physics, United States (2010).

U.S. Energy Information Administration. Energy Explained: Your guide to understanding energy. U.S. Energy Information Administration, Washington, DC. Jan. 13, 2013, posting date, Accessed at http://www.eia.gov/energyexplained/, accessed on Jul. 21, 2015.

U.S. Environmental Protection Agency. Renewable fuel standard (RFS). U.S. Environmental Protection Agency, Washington, DC. Jan. 13, 2013, posting date. Accessed at http://www.epa.gov/OMSWWW/fuels/renewablefuels/index.htm, accessed on Jul. 21, 2015.

Waltz, E., "Biotech's Green Gold?," Nature Biotechnology 27(1):15-18 Nature America Publishing, United States (2009).

Wang, H., et al., "Novel Bacterial Isolate from Permian Groundwater, Capable of Aggregating Potential Biofuel-Producing Microalga Nannochloropsis Oceanica IMETI," Applied and Environmental Microbiology 78(5):1445-1453, American Society for Microbiology, United States (2012).

Yoon, J.H., et al., "Paenibacillus Kribbensis sp. nov. and Paenibacillus Terrae sp. nov., Bioflocculants for Efficient Harvesting of Algal Cells," International Journal of Systematic and Evolutionary Microbiology 53(Pt1):295-301, IUMS, England (2003).

Yuan, S.J., et al., "Identification of Key Constituents and Structure of the Extracellular Polymeric Substances Excreted by Bacillus Megaterium TF10 for their Flocculation Capacity," Environmental Science Technology 45(3);1152-1157, American Chemical Society, United States (2011).

* cited by examiner

SEQUENCE LISTING

<160> NUMBER OF SEQ ID NOS: 3

<210> SEQ ID NO 1
<211> LENGTH: 1483
<212> TYPE: DNA
<213> ORGANISM: Bacillus sp. RP1137

<400> SEQUENCE: 1

```
caggatgaac gctggcggcg tgcctaatac atgcaagtcg agcgaactga ttagaagctt      60
gcttctatga cgttagcggc ggacgggtga gtaacacgtg ggcaacctgc ctgtaagact     120
gggataactt cgggaaaccg aagctaatac cggataggat cttctccttc atgggagatg     180
attgaaagat ggtttcggct atcacttaca gatgggcccg cggtgcatta gctagttggt     240
gaggtaacgg ctcaccaagg caacgatgca tagccgacct gagagggtga tcggccacac     300
tgggactgag acacggccca gactcctacg ggaggcagca gtagggaatc ttccgcaatg     360
gacgaaagtc tgacggagca acgccgcgtg agtgatgaag gctttcgggt cgtaaaactc     420
tgttgttagg gaagaacaag tacgagagta actgctcgta ccttgacggt acctaaccag     480
aaagccacgg ctaactacgt gccagcagcc gcggtaatac gtaggtggca agcgttatcc     540
ggaattattg ggcgtaaagc gcgcgcaggc ggtttcttaa gtctgatgtg aaagcccacg     600
gctcaaccgt ggagggtcat tggaaactgg ggaacttgag tgcagaagag aaaagcggaa     660
ttccacgtgt agcggtgaaa tgcgtagaga tgtgaggga acaccagtgg cgaaggcggc     720
ttttttggtc tgtaactgac gctgaggcgc gaaagcgtgg ggagcaaaca ggattagata     780
ccctggtagt ccacgccgta aacgatgagt gctaagtgtt agagggtttc cgcccttag     840
tgctgcagct aacgcattaa gcactccgcc tggggagtac ggtcgcaaga ctgaaactca     900
aaggaattga cgggggcccg cacaagcggt ggagcatgtg gtttaattcg aagcaacgcg     960
aagaaccttac caggtcttg acatcctctg acaactctag agatagagcg ttccccttcg    1020
ggggacagag tgacaggtgg tgcatggttg tcgtcagctc gtgtcgtgag atgttgggtt    1080
aagtcccgca acgagcgcaa cccttgatct tagttgccag cattcagttg ggcactctaa    1140
ggtgactgcc ggtgacaaac cggaggaagg tggggatgac gtcaaatcat catgcccctt    1200
atgacctggg ctacacacgt gctacaatgg atggtacaaa gggctgcaag accgcgaggt    1260
caagccaatc ccataaaacc attctcagtt cggattgtag gctgcaactc gcctacatga    1320
agctggaatc gctagtaatc gcggatcagc atgccgcggt gaatacgttc ccgggccttg    1380
tacacaccgc ccgtcacacc acgagagttt gtaacacccg aagtcggtgg agtaaccgta    1440
aggagctagc cgcctaaggt gggacagatg attggggtga agt                      1483
```

<210> SEQ ID NO 2
<211> LENGTH: 14
<212> TYPE: DNA
<213> ORGANISM: Artificial Sequence
<220> FEATURE:
<223> OTHER INFORMATION: 700f primer
<220> FEATURE:
<221> NAME/KEY: misc_feature
<222> LOCATION: (4)..(4)
<223> OTHER INFORMATION: k is g or t
<220> FEATURE:
<221> NAME/KEY: misc_feature
<222> LOCATION: (8)..(8)
<223> OTHER INFORMATION: r is g or a

<400> SEQUENCE: 2
gtgkagcrgt gaaa      14

```
<210> SEQ ID NO 3
<211> LENGTH: 14
<212> TYPE: DNA
<213> ORGANISM: Artificial Sequence
<220> FEATURE:
<223> OTHER INFORMATION: 700r primer
<220> FEATURE:
<221> NAME/KEY: misc_feature
<223> OTHER INFORMATION: y is c or t

<400> SEQUENCE: 3
ctacgcattt cacy                                                              14
```

COMPOSITIONS AND METHODS FOR COLLECTING ALGAE

CROSS-REFERENCE TO RELATED APPLICATIONS

This application claims the benefit of the filing date of each of U.S. Appl. No. 61/770,390, filed Feb. 28, 2013, U.S. Appl. No. 61/897,345, filed Oct. 30, 2013, and U.S. Appl. No. 61/915,594, filed Dec. 13, 2013, each of which is incorporated by reference herein in entirety.

REFERENCE TO SEQUENCE LISTING SUBMITTED ELECTRONICALLY

The content of the electronically submitted sequence listing in ASCII text file (Name: 3492_0010003_Sequence-Listing_ascii.txt; Size: 2.90 KB; and Date of Creation: Feb. 27, 2014) filed with the application is incorporated herein by reference in its entirety.

STATEMENT REGARDING PRIOR DISCLOSURES BY THE INVENTOR OR A JOINT INVENTOR

A prior presentation, Powell, R. J. and Hill, R. T., "Rapid Harvest of Microalgae Using a Novel Bacterial Isolate," was made on Jun. 13, 2012, during $2^{nd}$ International Conference on Algal Biomass, Biofuels & Bioproducts, in San Diego, Calif. A prior journal article, Powell, R. J. and Hill, R. T., "Rapid Aggregation of Biofuel-Producing Algae by the Bacterium *Bacillus* sp. Strain RP1137," *Applied Environ. Microbiol.* 79:6093-6101, was published online on Jul. 26, 2013, and in print on Oct. 1, 2013. Copies of the presentation and publication will be provided in an Information Disclosure Statement pursuant to the guidance of 78 Fed. Reg. 11076 (Feb. 14, 2013).

BACKGROUND OF THE INVENTION

Field of the Invention

The invention relates to compositions containing *Bacillus* sp., optionally with magnetite, useful in methods for collecting algae. The invention also relates to methods for collecting algae by contacting algae and bare maghemite and compositions thereof.

Background Art

Algal derived biofuels are one of the best alternatives for economically replacing liquid fossil fuels with a fungible renewable energy source. Algae can accumulate more than 50% of their biomass in oil and can be grown in saline water on land not suitable for agriculture. These characteristics mean algal biofuels do not compete for fresh water and arable land with conventional food crops. In addition, less land will be needed to produce the needed fuel than is required for other biofuel feed stocks. One major problem with algal biofuels is the algae most suited for biofuel production are small in size and difficult to harvest. Efficient harvest is crucial because algae cultures yield a few grams of algae per liter of water. The algae must be separated from the water before the oil can be extracted. At the laboratory scale algae cultures can be harvested by centrifugation or filtration, but these methods are too energy and capital intensive for harvesting algae from the immense volumes of water needed for commercial scale production of algal biofuels. Chemical flocculation can be used at large scales, but requires treatment of the water after the algae are removed so the water can safely be reused or released into the environment.

There is a need for improved methods for collecting algae.

BRIEF SUMMARY OF THE INVENTION

The invention is directed to an isolated *Bacillus* sp. comprising a nucleic acid molecule having a polynucleotide sequence at least 99% identical to SEQ ID NO:1. The invention is directed to a composition comprising an alga and an isolated *Bacillus* sp. comprising a nucleic acid molecule having a polynucleotide sequence at least 99% identical to SEQ ID NO:1. In some embodiments, the *Bacillus* sp. is *Bacillus megaterium*, *Bacillus aryabhattai* or *Bacillus horikoshii*. In some embodiments, the *Bacillus* sp. is RP1137. In some embodiments, the alga is *Nannochloropsis* sp., *Tetraselmis* sp. or *Chaetoceros* sp.

The invention is directed to a method for collecting algae, comprising contacting an algae culture and an isolated *Bacillus* sp. comprising a nucleic acid molecule having a polynucleotide sequence at least 99% identical to SEQ ID NO:1, and forming an algae aggregate. In some embodiments, the method further comprises separating the algae aggregate from the culture. In some embodiments, the *Bacillus* sp. is *Bacillus megaterium*, *Bacillus aryabhattai* or *Bacillus horikoshii*. In some embodiments, the *Bacillus* sp. is RP1137. In some embodiments, the algae culture comprises *Nannochloropsis* sp., *Tetraselmis* sp. or *Chaetoceros* sp. In some embodiments, the algae aggregate is formed in less than 30 seconds following the contacting of the algae culture and the isolated *Bacillus* sp.

The invention is directed to a composition comprising magnetite and an isolated *Bacillus* sp. RP1137. In some embodiments, the composition further comprises an alga.

The invention is directed to a method for producing a *Bacillus*/magnetite conjugate, comprising contacting an isolated *Bacillus* sp. RP1137 and magnetite, and collecting the conjugated *Bacillus*/magnetite. In some embodiments, the *Bacillus* is a dead cell. In some embodiments, the mixing occurs in at a pH of 7.

The invention is directed to a method for collecting algae, comprising contacting the *Bacillus*/magnetite conjugate described herein and an algae culture, and forming an algae aggregate. In some embodiments, the method further comprises separating the algae aggregate from the culture. In some embodiments, the method further comprises recovering the *Bacillus*/magnetite conjugate and reusing the *Bacillus*/magnetite conjugate to form an algae aggregate from another algae culture.

In some embodiments, in the methods described herein, the pH of the culture is greater than 8. In some embodiments, the pH of the culture is 9 or greater. In some embodiments, the salinity of the culture is 0 ppt to 156 ppt. In some embodiments, the temperature of the culture is 10° C. to 40° C. In some embodiments, the algae are *T. chuii*, *T. sucia*, *Phaeodactylum* sp., *N. oceanica*, *N. oleoabundans*, *C. cryptica*, or *N. angularis*. In some embodiments, the ratio of the *Bacillus* to algae cells is 1:1 to 1:5. In some embodiments, the culture contains divalent cations.

In some embodiments, the methods of the invention further comprises lowering the pH of the culture to reverse the aggregation and reusing the *Bacillus* to form an algae aggregate in another algae culture.

In some embodiments, the magnetite is unoxidized powder. In some embodiments, the algae are in the exponential phase of growth. In some embodiments, the *Bacillus* sp. is in the exponential phase of growth. In some embodiments, the culture contains 1 mM to 30 mM calcium ions. In some embodiments, the salinity of the culture is 5 ppt to 200 ppt. In some embodiments, the temperature of the culture is 5° C. to 50° C.

The invention is directed to a method of producing maghemite, comprising heating magnetite powder, and oxidizing the magnetite to form maghemite. The invention is directed to a composition comprising an alga and bare maghemite. The invention is also directed to a method for collecting algae, comprising binding algae in a culture to bare maghemite, and forming an algae aggregate, wherein the binding of algae to bare maghemite is not reversible by altering the pH.

In some embodiments, the binding of algae to bare maghemite is not pH sensitive. In some embodiments, the method includes repeating the binding of algae in the culture to the bare maghemite, and increasing the algae aggregate.

In some embodiments, the algae is collected in a dry weight ratio of algae:maghemite of 1:1 or more. In some embodiments, the algae are green algae. The green algae can be *Nannochloropsis, Tetraselmis*, or *Scenedesmus*. In some embodiments, the algae are brown algae. The brown algae can be *Isochrysis*. In some embodiments, the algae are *Lemnaceae*.

In some embodiments, the algae culture is an artificial medium, e.g., growth media, or fresh, brackish or salt water. The algae culture can be a closed culture or an open culture. An open culture can be a pond, a lake, a bay, coastal waters, or an ocean.

BRIEF DESCRIPTION OF THE DRAWINGS/FIGURES

FIG. 1. Aggregation of algae is rapid upon addition of the bacterium *Bacillus* sp. RP1137. Aggregates form within 15 s, and by 30 s the aggregates have settled out of solution. RP1137 cells were added to the bottle of a *Tetraselmis* sp. on the right, and the bottle on the left served as a control.

Figure 2:
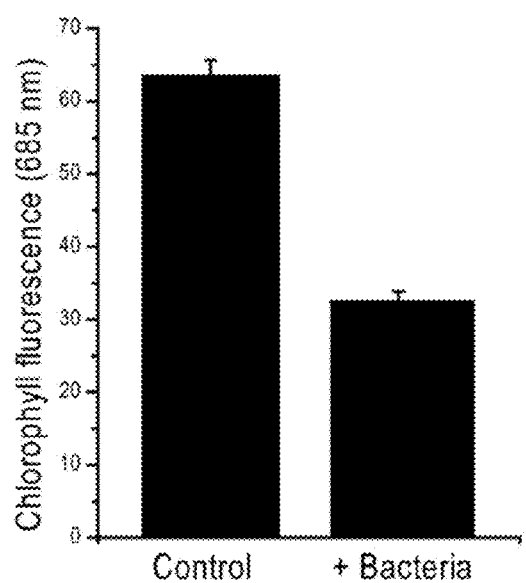

FIG. 2. *Nannochloropsis* sp. IMET1 chlorophyll fluorescence in the upper layer with (+Bacteria) and without (Control) the addition of the bacterium *Bacillus* sp. RP1137, showing reduction of algae density in suspension upon addition of bacteria.

Figure 3:
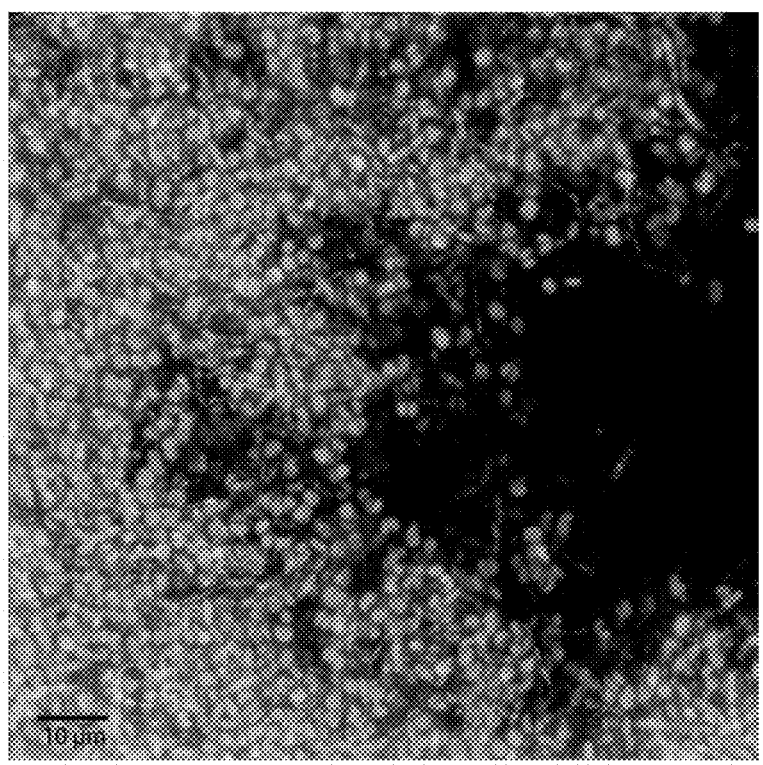

FIG. 3. Laser scanning confocal micrograph of an *N. oceanica* IMET1-*Bacillus* sp. RP1137 aggregate. Algae (green) were visualized by chlorophyll autofluorescence, and the bacteria (orange) were visualized using SYBR green I staining.

Figure 4:
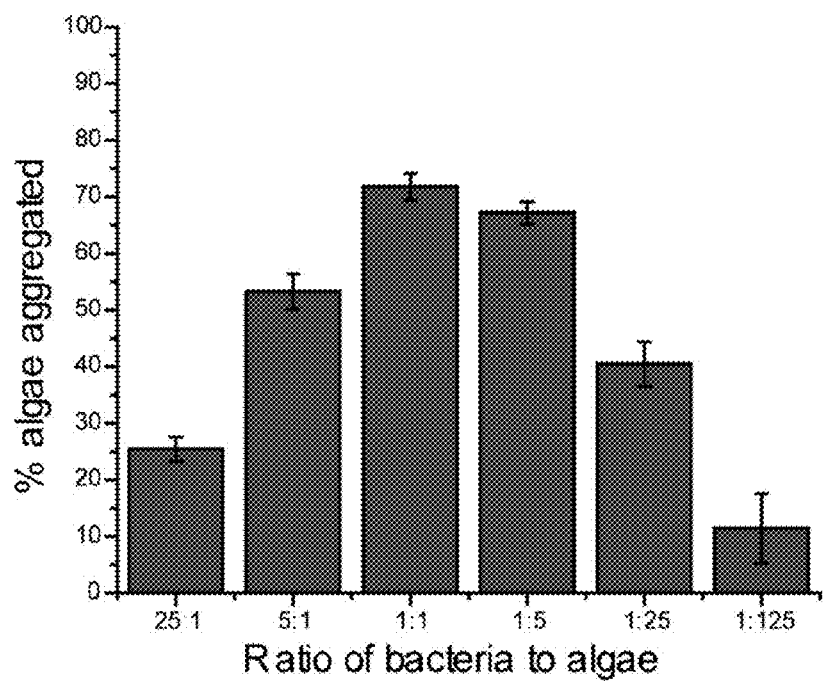

FIG. 4. Aggregation efficiency is the highest when one bacterium is added for every one to five algal cells present. At ratios above and below these ratios, aggregation efficiency is reduced. The result for the ratio of 5:1 is statistically significantly different from that for the ratio of 1:1 (P=8.0E−5). The result for the ratio of 1:1 is statistically significantly different from that for the ratio of 1:5 (P=0.009). Bars and error bars represent the means and standard errors, respectively, of five independent aggregation reactions. A value of 100% is aggregation of all algal cells.

Figure 5:
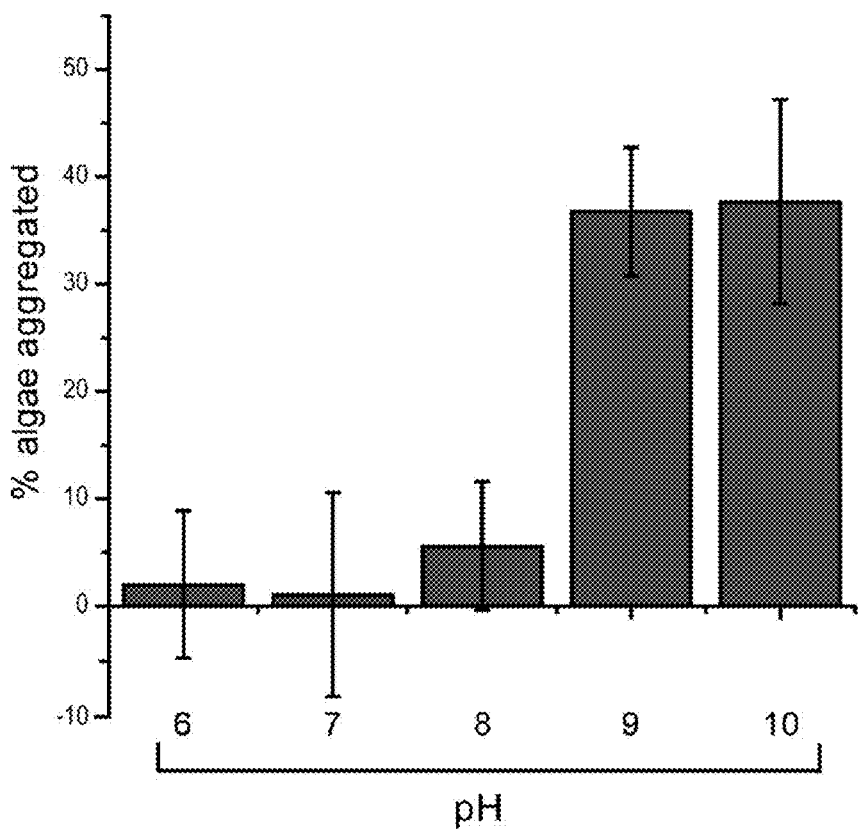

FIG. 5. Aggregation efficiency is pH dependent, with optimal aggregation occurring at pH 9 and above. Aggregation at pH 9 is significantly higher than that at pH 8 (P=5.9E−8). Aggregation above pH 9 is not significantly increased (P>0.05). There was no significant change in aggregation below pH 8 (P>0.05). Bars and error bars represent the means and standard errors, respectively, of eight independent aggregation reactions. A value of 100% is aggregation of all algal cells.

Figure 6:
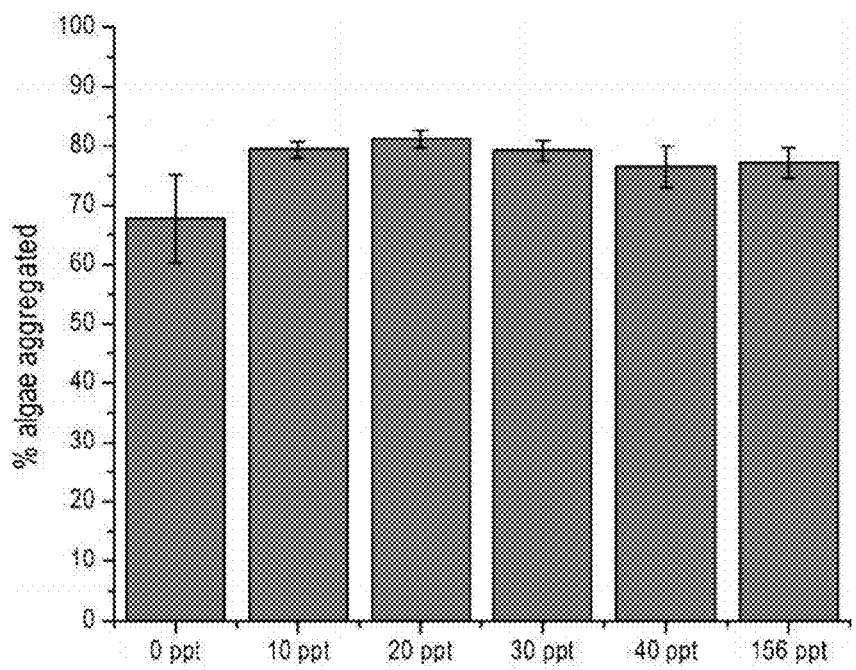

FIG. 6. Aggregation is inhibited at low salinity and high salinity relative to the 20 ppt salinity used in the algal medium. Aggregation is significantly reduced at 0 ppt compared to 10 ppt salinity (p=0.002) and 20 ppt (p=0.001). Samples at 20, 30 and 40 ppt salinity are not significantly different (p>0.05). A small but significant decrease in aggregation is observed between samples at 20 and 156 ppt salinity (p=0.002). Bar and error bars represent the mean and standard error respectively of eight independent aggregation reactions. A value of 100% is aggregation of all algal cells.

Figure 7:
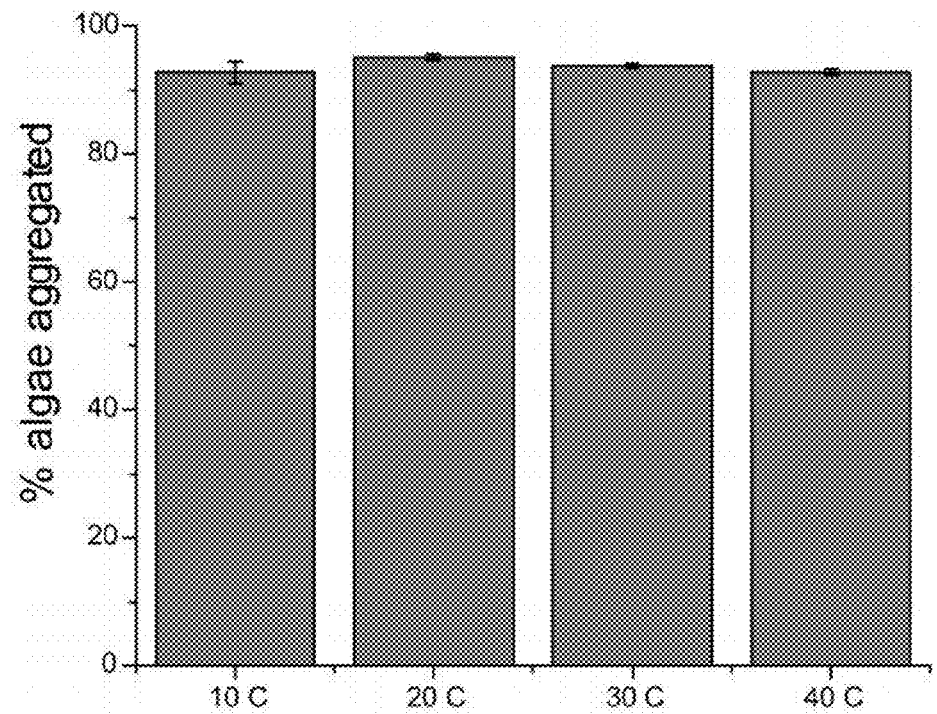

FIG. 7. Temperature has minor but significant effects on aggregation. Aggregation is optimal at 20° C. and is significantly higher at 20° C. than 10° C. (p=0.006), 30° C. (p=3.9E−5) and 40° C. (p=3.1E−7). Bar and error bars represent the mean and standard error respectively of eight independent aggregation reactions. A value of 100% is aggregation of all algal cells.

Figure 8:
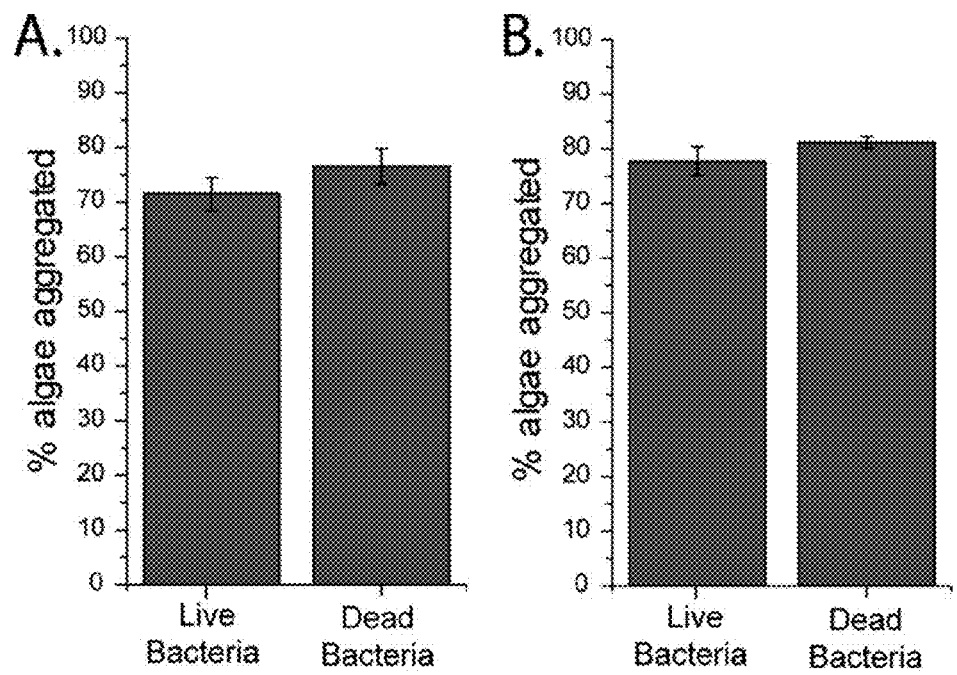

FIG. 8. The mechanism of aggregation does not depend on live bacteria or live algae. (A) Live algae were aggregated with both live and dead bacteria. Dead bacteria had a minor but significant increase in aggregation relative to live bacteria (P=0.06). (B) Dead algae were aggregated with both live and dead bacteria, with dead bacteria aggregating the dead bacteria significantly better (P=0.01). Bars and error bars represent the means and standard errors, respectively, of eight independent aggregation reactions. A value of 100% is aggregation of all algal cells.

Figure 9:
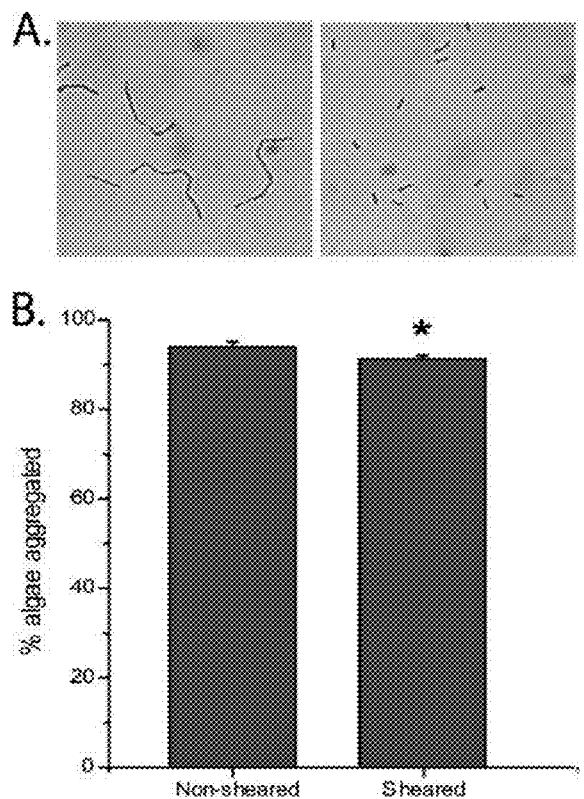

FIG. 9. Bacterial filament length has a minor effect on aggregation efficiency. (A) Phase-contrast image of RP1137 before shearing (left) and the same population of cells after shearing (right). (B) Aggregation of *Nannochloropsis* with non-sheared cells and sheared cells showing a statistically significant (P=2.71E−7) but minor effect due to filament length. Bars and error bars represent the means and standard errors, respectively, of 16 independent aggregation reactions. A value of 100% is aggregation of all algal cells.

Figure 10:
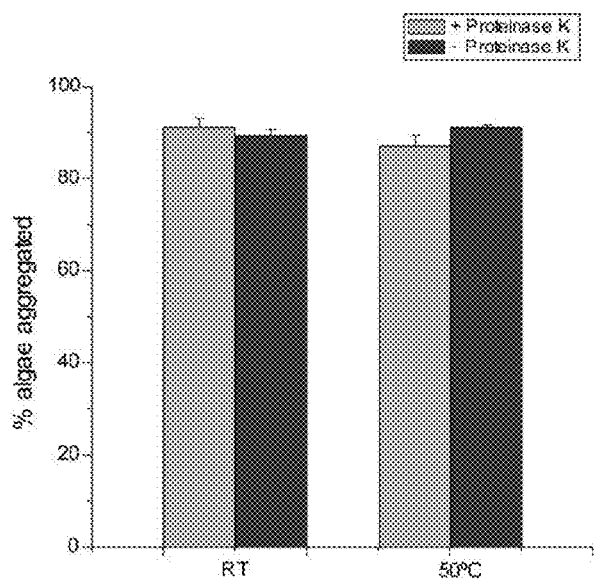

FIG. 10. Aggregation with RP1137 cells that were treated with proteinase K to digest surface associated proteins. Cells incubated at room temperature (RT) with proteinase K do not have a statistically significant difference in aggregation efficiency compared to untreated control (p>0.05), while cells treated at 50° C. show a minor but statistically significant decrease in aggregation efficiency (p=0.002) relative to the untreated control. Bar and error bars represent the mean and standard error respectively of eight independent aggregation reactions. A value of 100% is aggregation of all algal cells.

Figure 11:
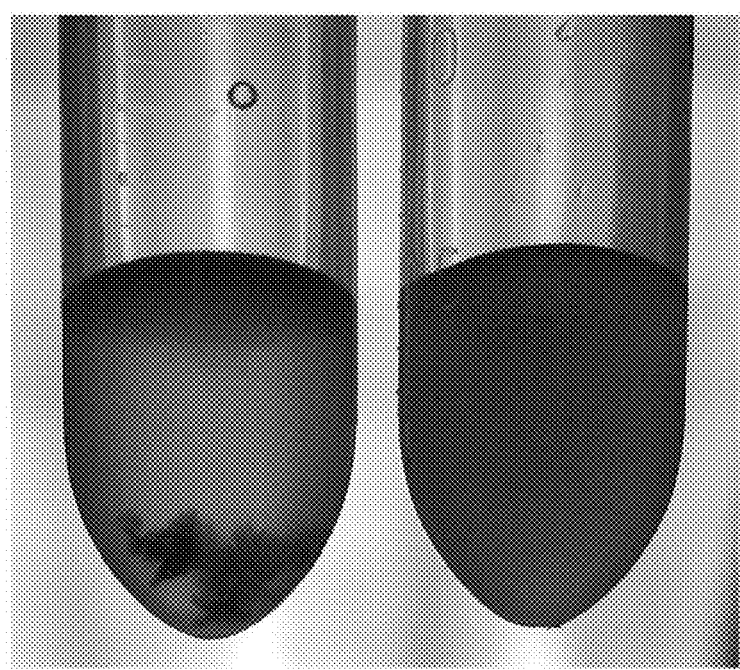
Figure 11:
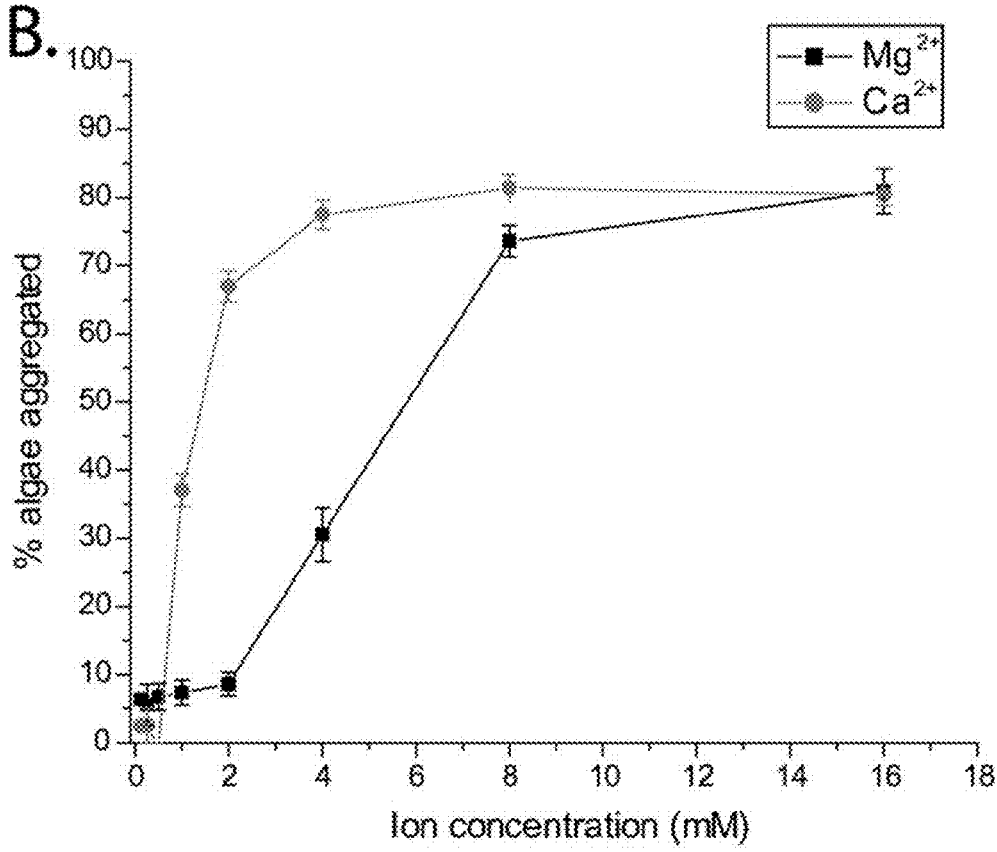

FIG. 11. Aggregation is dependent on divalent cations. (A) Aggregation in artificial seawater is inhibited by the addition of EDTA and EGTA (right) compared to that for the untreated control (left). (B) Dose-dependent effect of calcium and magnesium on aggregation, showing increasing aggregation with increasing concentrations of calcium or magnesium. Points and error bars represent the means and standard errors, respectively, of four independent aggregation reactions. A value of 100% is aggregation of all algal cells.

Figure 12:
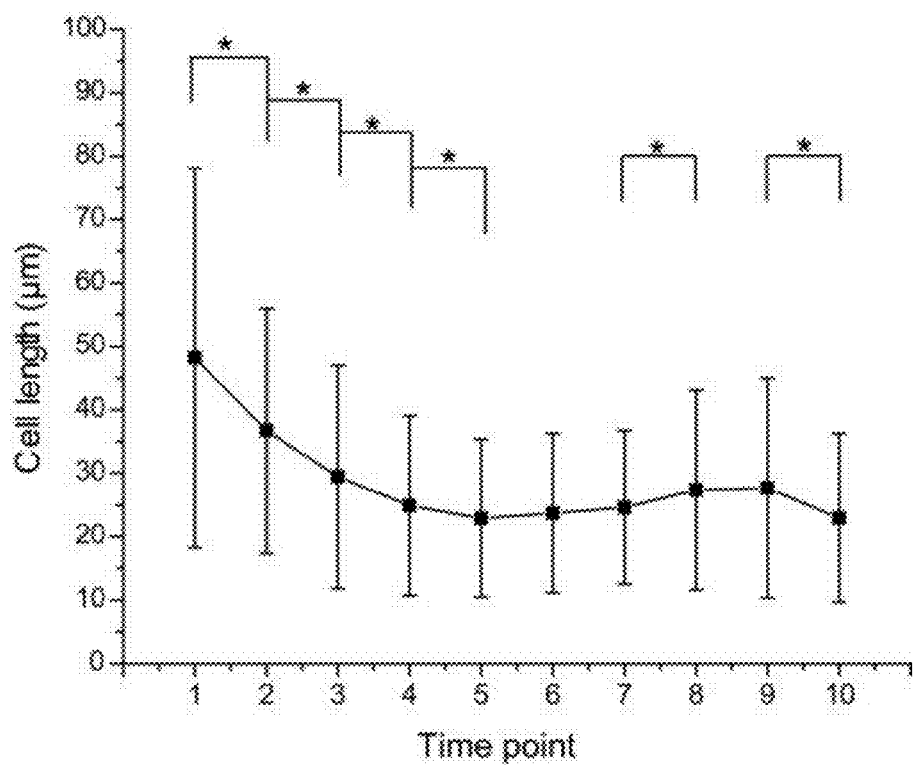

FIG. 12. *Bacillus* sp. RP1137 cell length changes over time. Bar and error bars represent the mean and standard error respectively of cell length measurements of between 900-1600 individual cells per time point. (*) indicates statistically significant difference where p<0.0005.

Figure 13:
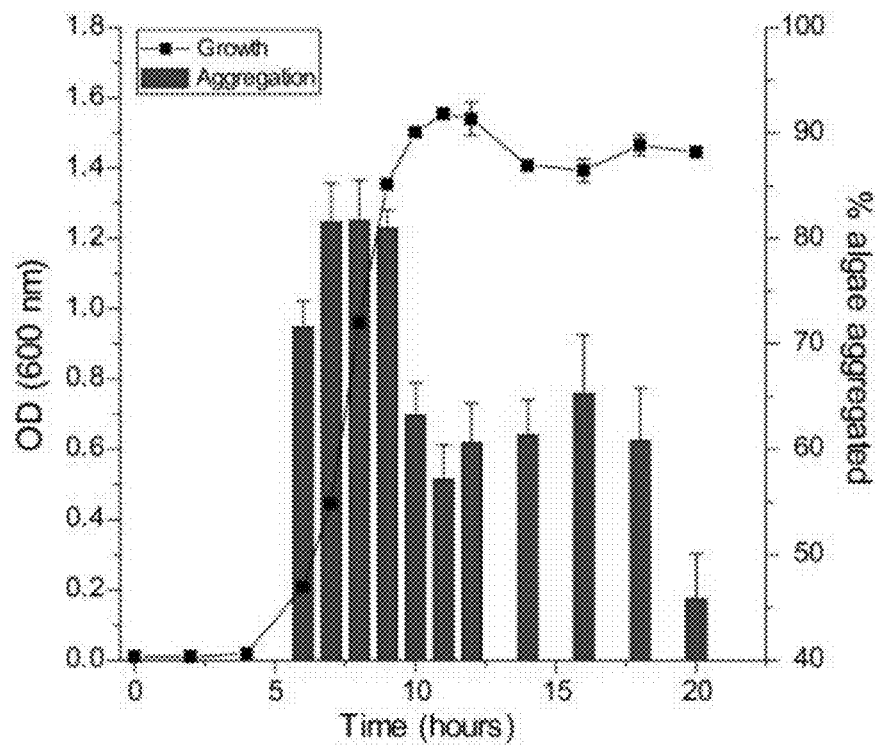

FIG. 13. Normalized aggregation efficiency of RP1137 cells is highest in exponential phase. Samples are normalized by cell surface area so the same surface area is available for aggregating algae at each time point. Bar and error bars represent the mean and standard error respectively of eight independent aggregation reactions. A value of 100% is aggregation of all algal cells.

Figure 14:
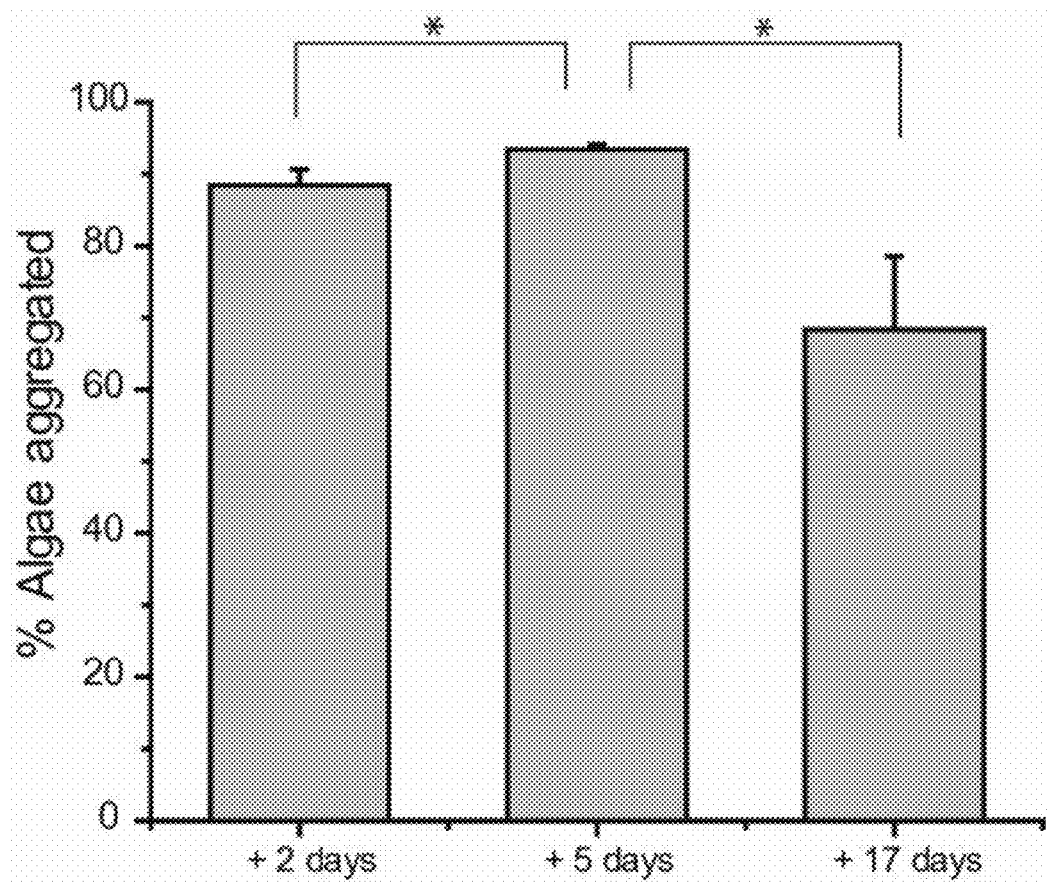

FIG. 14. Normalized aggregation efficiency of *Nannochloropsis* at two, five and 17 days after subculturing. Aggregation is most efficient at five days after subculture. Bar and error bars represent the mean and standard error respectively of eight independent aggregation reactions. (*) indicates statistically different samples with p<0.0005.

Figure 15:
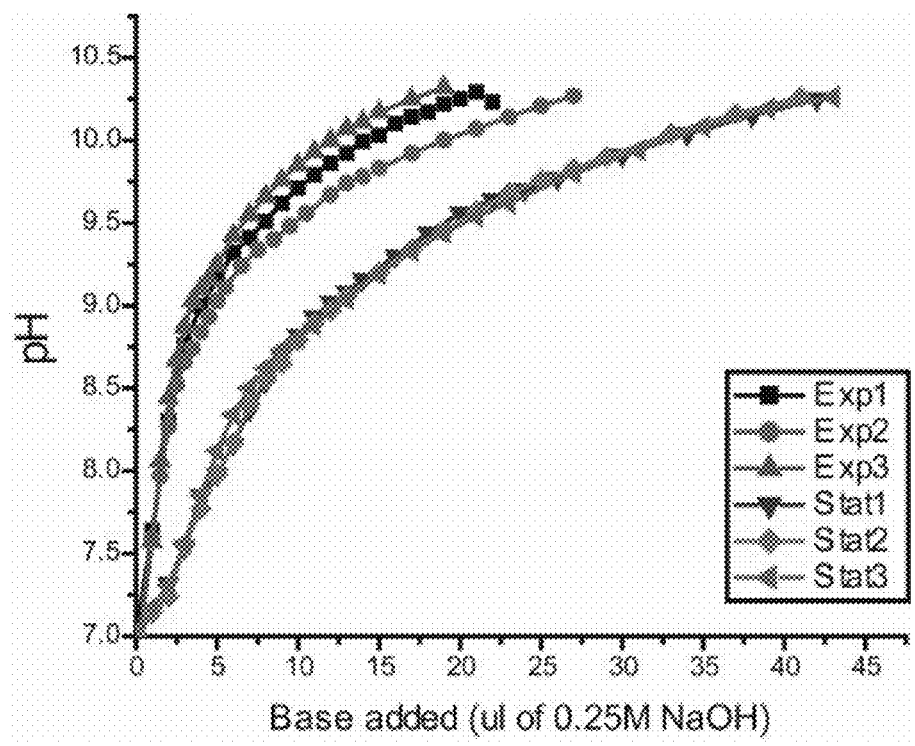

FIG. 15. Base titration curves of live RP1137 cells. Curves represent individual trials from RP1137 cells from either exponential phase (Exp) or stationary phase (Stat).

Figure 16:
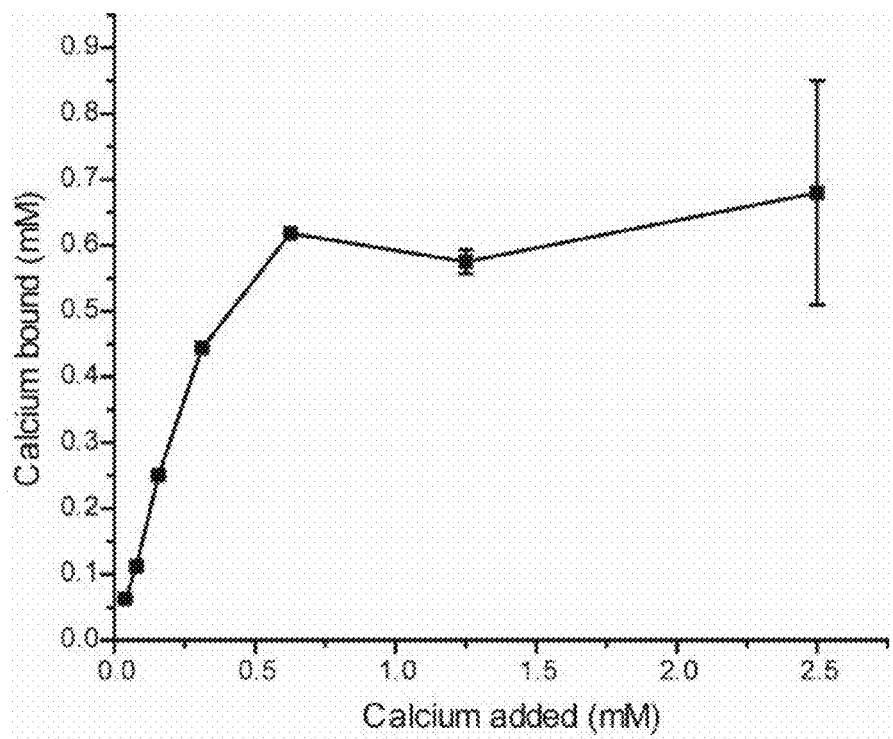

FIG. 16. Binding of calcium to RP1137 cells increases with increasing calcium concentrations. Points and error bars represent the mean and standard error respectively of three independent calcium-binding reactions.

Figure 17:
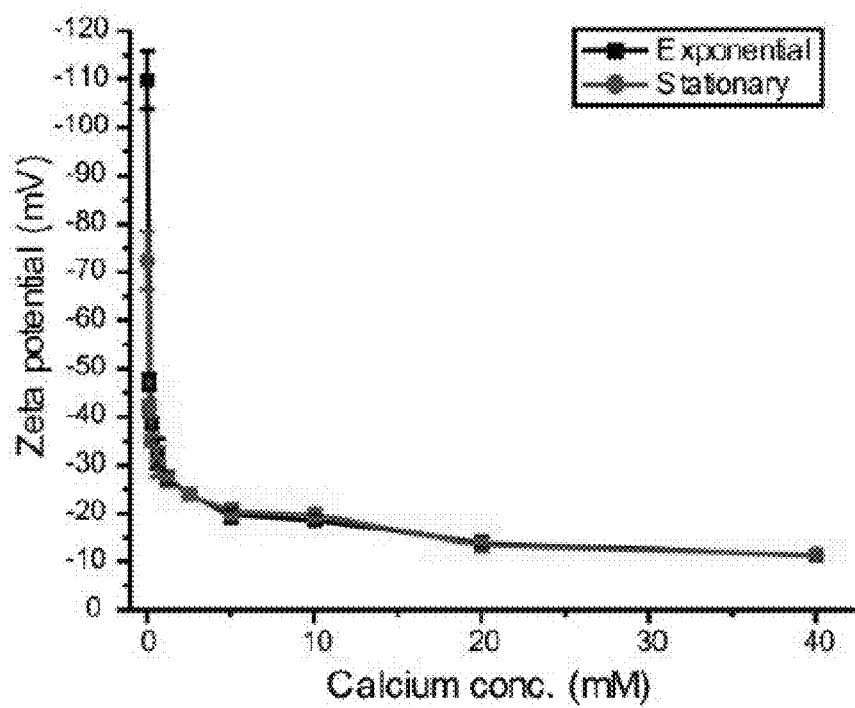
Figure 17:
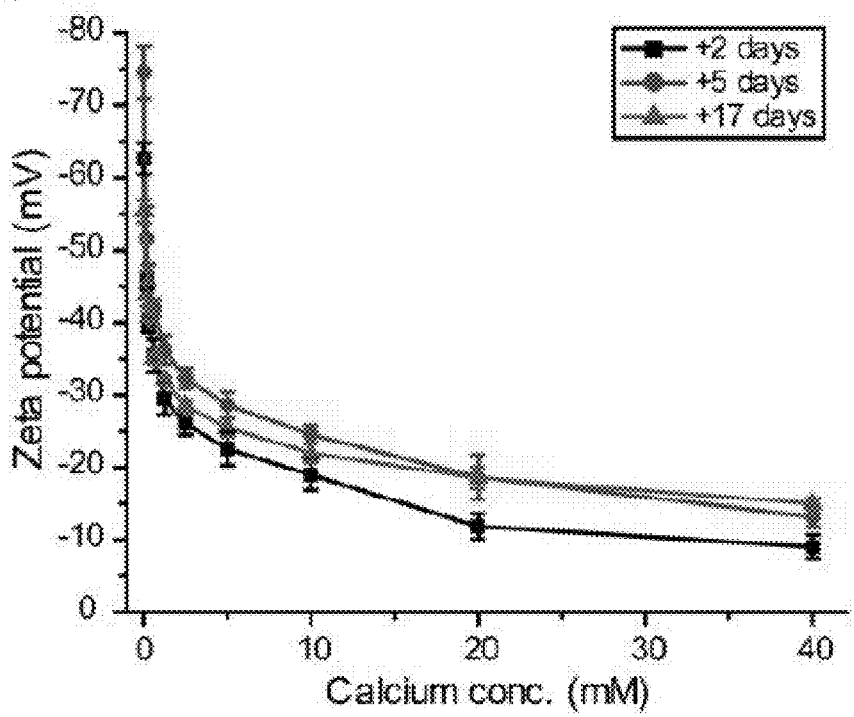

FIG. 17. Surface charge of RP1137 cells (A) and *Nannochloropsis* cells (B) at different stages of growth and different calcium concentrations. Charge decreases with increasing calcium concentration. Points and error bars represent the mean and standard error respectively of three biological replicates each with three technical replicates.

Figure 18:
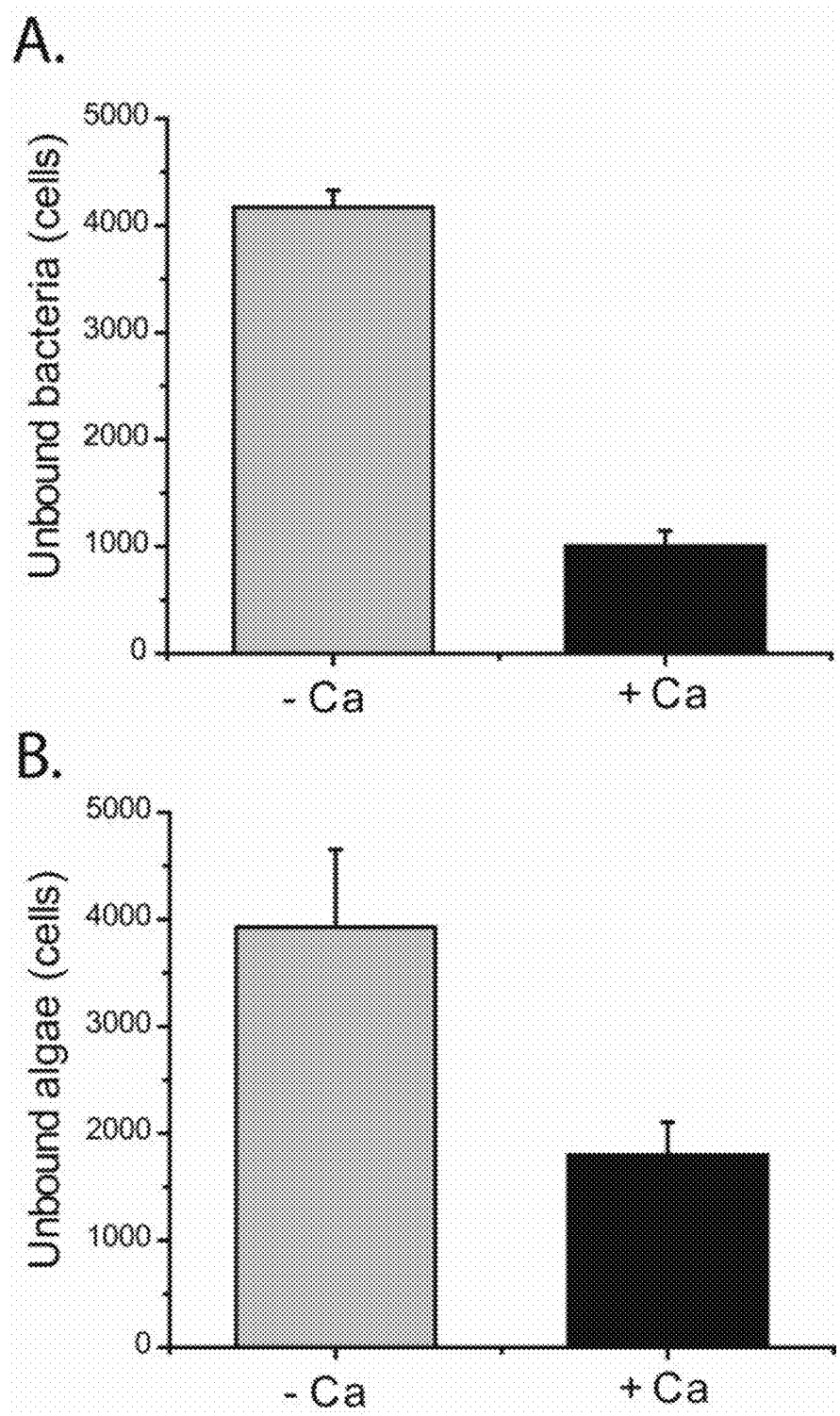

FIG. 18. Binding of RP1137 cells (A) and *Nannochloropsis* cells (B) to hydrophobic C18 beads in the presence or absence of 10 mM $CaCl_2$. Both RP1137 and *Nannochloropsis* cells bind more effectively to the beads in the presence of calcium. Bar and error bars represent the mean and standard error respectively of three biological replicates with three technical replicates each.

Figure 19:
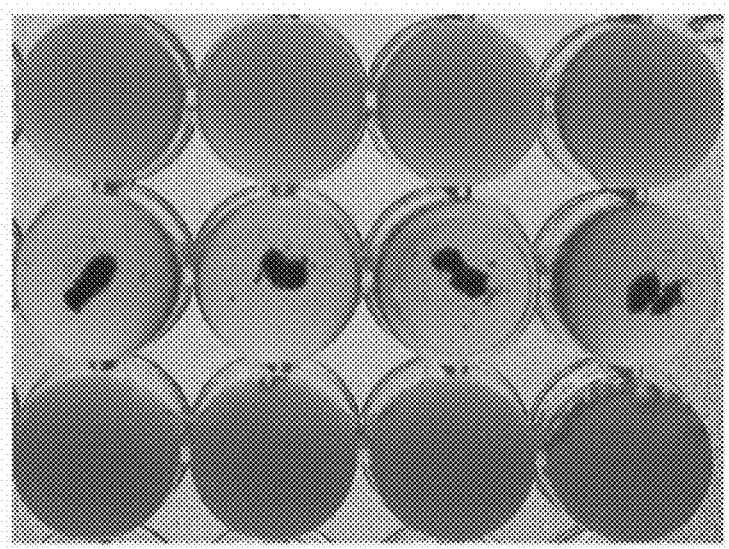
Figure 19:
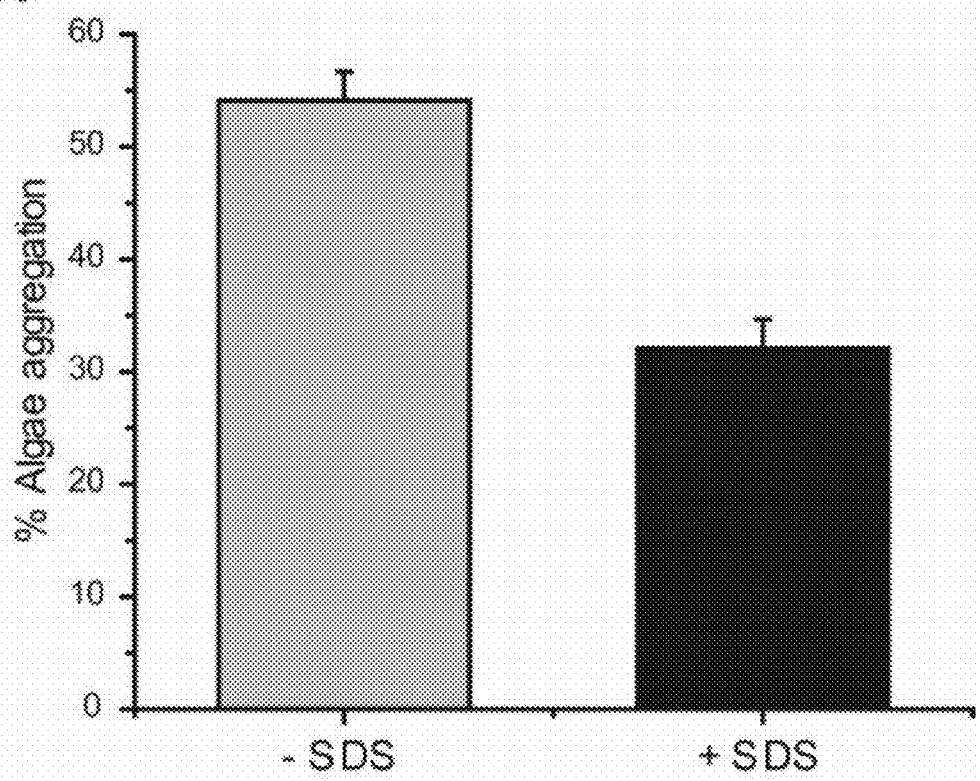

FIG. 19. Aggregation is inhibited by the presence of SDS. (A) Visual result showing the no bacteria controls, algae with bacteria and algae with bacteria and SDS. (B) Quantitation of the percent of algae aggregated with and without SDS using the filtration aggregation assay. Bar and error bars represent the mean and standard error respectively of four independent aggregation reactions. A value of 100% is aggregation of all algal cells.

Figure 20:
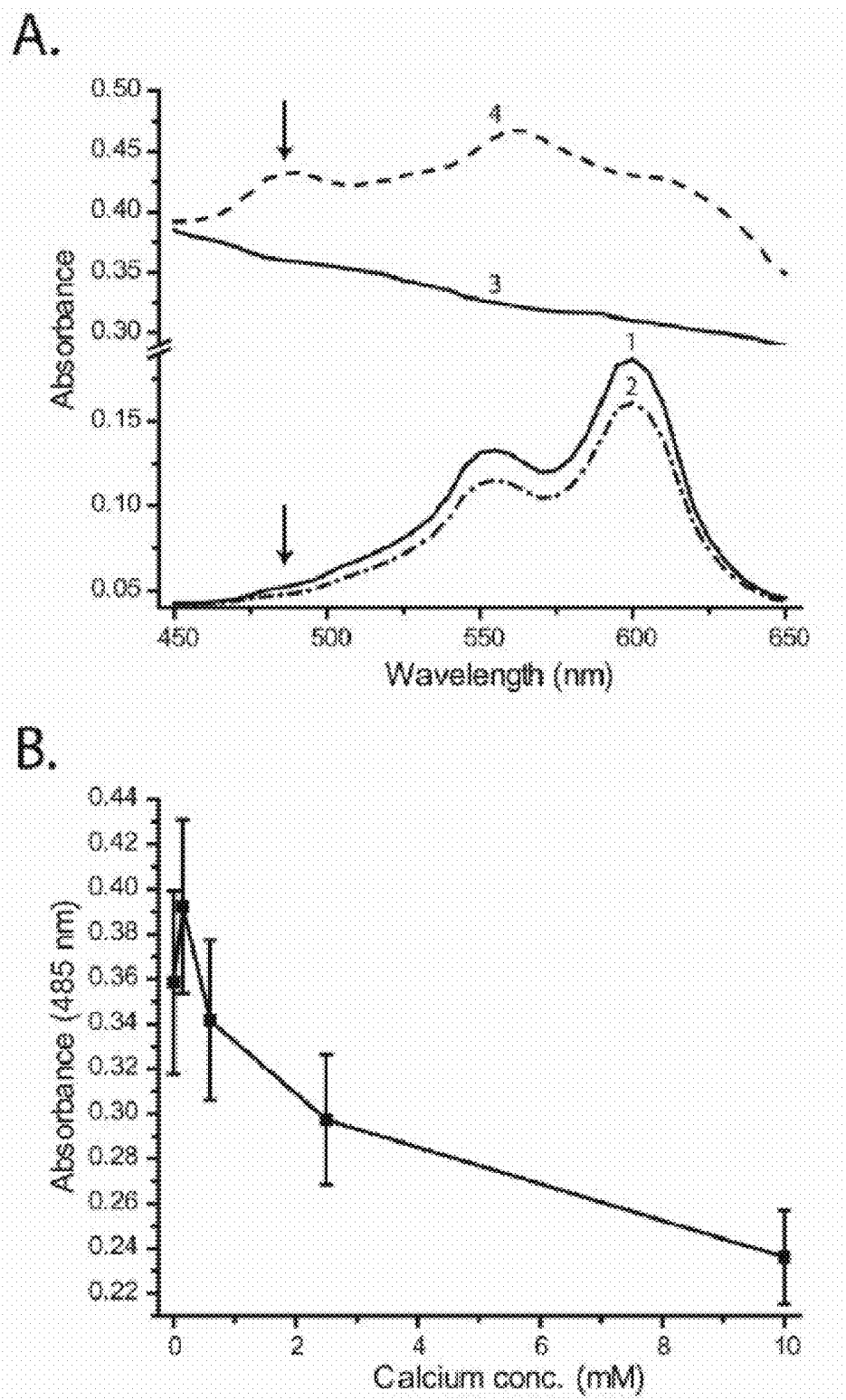

FIG. 20. Pinacyanol dye binding to RP1137 cells is disrupted by the addition of calcium. (A) Absorbance spectra of (1) Water+dye, (2) Water+dye+10 mM $CaCl_2$, (3) RP1137 cells alone and (4) RP1137 cells+dye. Arrows indicate position of the 485 nm absorbance band indicative of pinacyanol binding teichoic acid. (B) Absorbance of pinacyanol stained cells at 485 nm with increasing calcium concentration. Points and error bars represent the mean and standard error respectively of three biological replicates each with two technical replicates.

Figure 21:
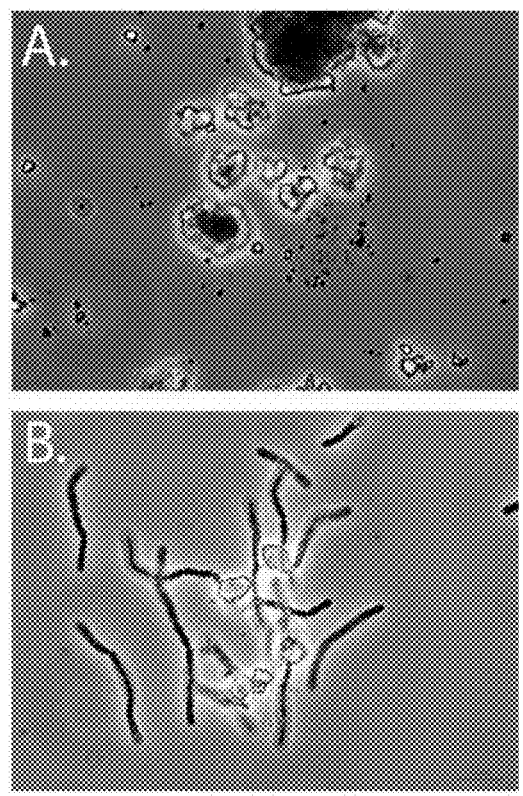

FIG. 21. Conjugation of bacteria to magnetite particles. (A) Particles alone after synthesis. (B) Particles conjugated to the aggregating bacterium.

Figure 22:
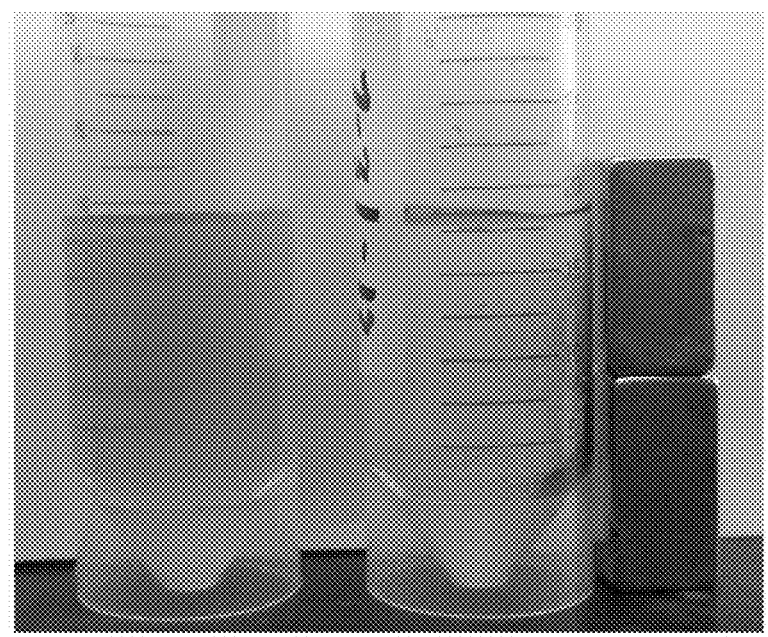

FIG. 22. Harvest of diverse algae from pond water. Pond water (left) and pond water plus maghemite particles (right) near a permanent magnet.

Figure 23:
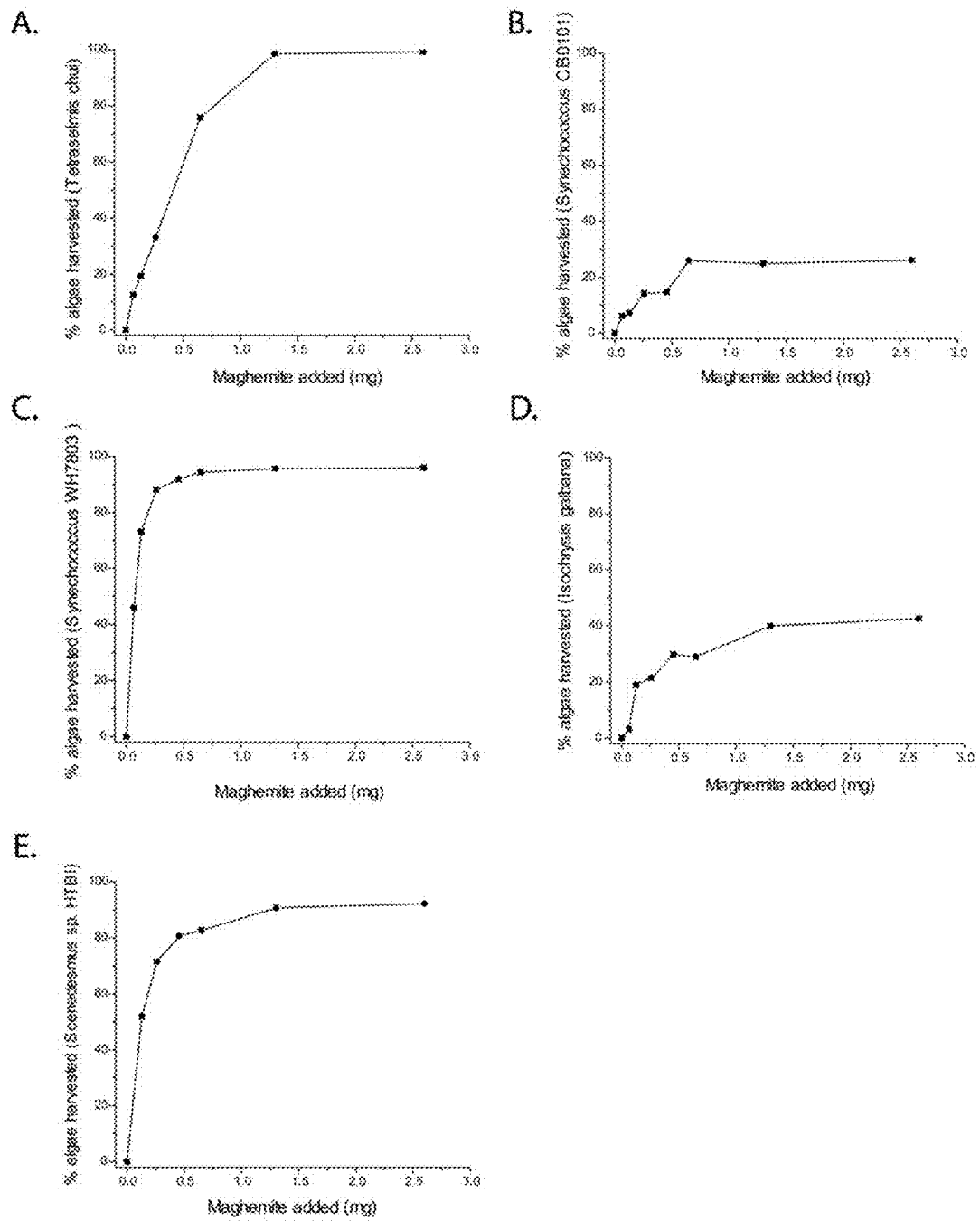

FIG. 23. Harvest efficiency of maghemite beads on different algae. Percentage of algae harvested is shown for (A) *Tetraselmis chui*, (B) *Synechococcus* CB0101, (C) *Synechococcus* WH7803, (D) *Isochrysis galbana* and (E) *Scenedesmus* sp. HTB1.

Figure 24:
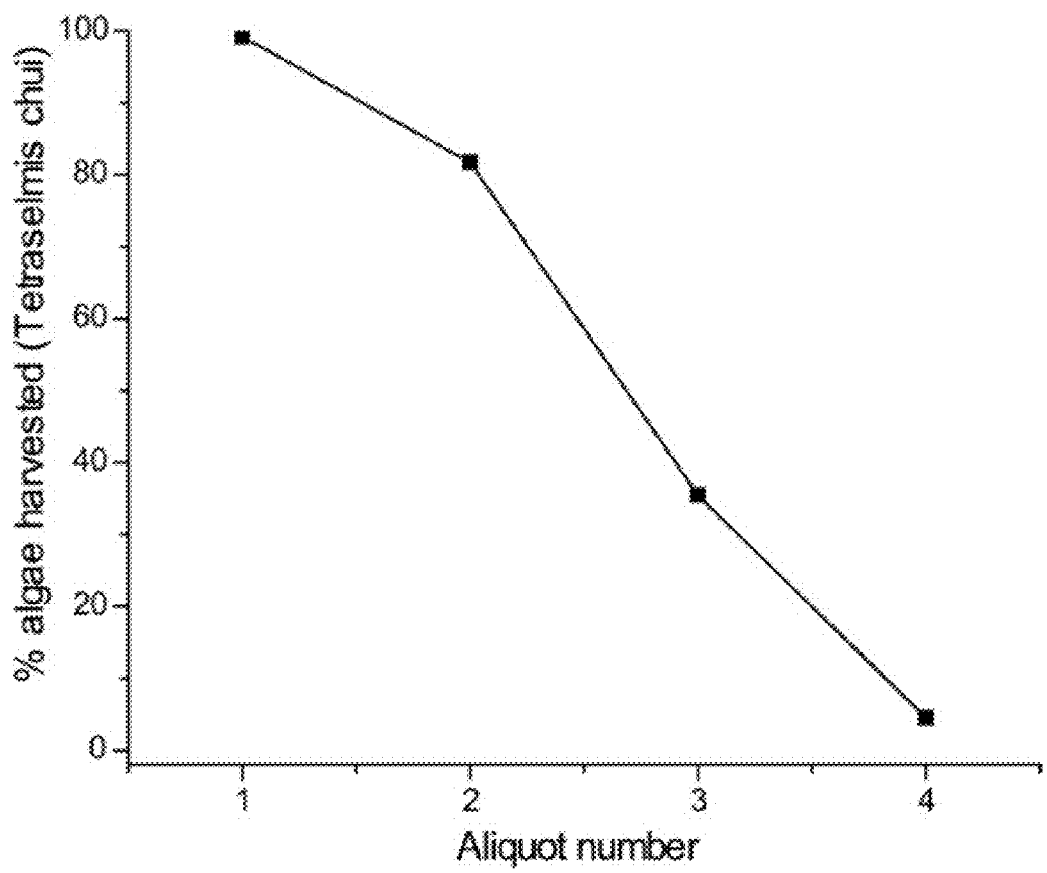

FIG. 24. Testing bead saturation by using the same batch of particles to harvest successive aliquots of algae. The results show the beads are not saturated until four successive rounds of harvesting.

DETAILED DESCRIPTION OF THE INVENTION

In the following sections, various exemplary compositions and methods are described in order to detail various embodiments. It will be obvious to one skilled in the art that practicing the various embodiments does not require the employment of all or even some of the details outlined herein, but rather that concentrations, times and other specific details may be modified through routine experimentation. In some cases, well-known methods or components have not been included in the description.

The invention is directed to an isolated *Bacillus* sp. comprising a nucleic acid molecule having a polynucleotide sequence at least 90% identical, 95% identical, 98% identical, 99% identical, or 100% identical to SEQ ID NO:1. The invention is directed to an isolated microorganism of the species deposited under ATCC Accession No. PTA-121034. The invention is directed to an isolated microorganism having the characteristics of the species deposited under ATCC Accession No. PTA-121034. The invention is directed to an isolated *Bacillus* sp. comprising a nucleic acid molecule having a polynucleotide sequence at least 90% identical, 95% identical, 98% identical, 99% identical, or 100% identical to a 16s rRNA polynucleotide of the microorganism deposited under ATCC Accession No. PTA-121034.

The invention is directed to a composition comprising an alga and an isolated *Bacillus* sp. comprising a nucleic acid molecule having a polynucleotide sequence at least 90% identical, 95% identical, 98% identical, 99% identical, or 100% identical to SEQ ID NO:1, The invention is directed to a composition comprising an alga and an isolated microorganism of the species deposited under ATCC Accession No. PTA-121034. The invention is also directed to a composition comprising an alga and an isolated microorganism having the characteristics of the species deposited under ATCC Accession No. PTA-121034. The invention is directed to a composition comprising an alga and an isolated *Bacillus* sp. comprising a nucleic acid molecule having a polynucleotide sequence at least 90% identical, 95% identical, 98% identical, 99% identical, or 100% identical to a 16S rRNA polynucleotide of the microorganism deposited under ATCC Accession No. PTA-121034.

The invention is directed to a method for collecting algae, comprising contacting an algae culture and an isolated *Bacillus* sp. comprising a nucleic acid molecule having a polynucleotide sequence at least 90% identical, 95% identical, 98% identical, 99% identical, or 100% identical to SEQ ID NO:1, and forming an algae aggregate. The invention is directed to a method for collecting algae, comprising contacting an algae culture and an isolated microorganism of the species deposited under ATCC Accession No. PTA-121034, and forming an algae aggregate. The invention is directed to a method for collecting algae, comprising contacting an algae culture and an isolated microorganism having the characteristics of the species deposited under ATCC Accession No. PTA-121034, and forming an algae aggregate. The invention is directed to a method for collecting algae, comprising contacting an algae culture and an isolated *Bacillus* sp. comprising a nucleic acid molecule having a polynucleotide sequence at least 90% identical, 95% identical, 98% identical, 99% identical, or 100% identical to a 16S rRNA polynucleotide of the microorganism deposited under ATCC Accession No, PTA-121034, and forming an algae aggregate. In some embodiments, the method can further comprising separating the algae aggregate from the culture.

The invention is directed to a composition comprising magnetite and an isolated *Bacillus* sp. RP1137. The *Bacillus* sp. RP1137, was deposited under the International Budapest Treaty on Feb. 28, 2014 at the American Type Culture Collection, Patent Depository, 10801 University Boulevard, Manassas, Va. 20110-2209, under ATCC Accession No, PTA-121034. The invention is directed to a composition comprising magnetite and an isolated *Bacillus* sp. comprising a nucleic acid molecule having a polynucleotide sequence at least 90% identical, 95% identical, 98% identical, 99% identical, or 100% identical to SEQ ID NO:1. The invention is directed to a composition comprising magnetite and an isolated microorganism of the species deposited under ATCC Accession No. PTA-121034. The invention is also directed to a composition comprising magnetite and an isolated microorganism having the characteristics of the species deposited under ATCC Accession No. PTA-121034. The invention is directed to a composition comprising magnetite and an isolated *Bacillus* sp. comprising a nucleic acid molecule having a polynucleotide sequence at least 90% identical, 95% identical, 98% identical, 99% identical, or 100% identical to a 16s rRNA polynucleotide of the microorganism deposited under ATCC Accession No. PTA-121034. In some embodiments, the composition can further comprise an alga.

The invention is directed to a method for producing a *Bacillus*/magnetite conjugate, comprising contacting an isolated *Bacillus* sp. RP1137 and magnetite, and collecting the conjugated *Bacillus*/magnetite. The invention is directed to a method for producing a *Bacillus*/magnetite conjugate, comprising contacting an isolated microorganism of the species deposited under ATCC Accession No. PTA-121034 and magnetite, and collecting the conjugated *Bacillus*/magnetite. The invention is directed to a method for producing a *Bacillus*/magnetite conjugate, comprising contacting an isolated microorganism having the characteristics of the species deposited under ATCC Accession No. PTA-121034 and magnetite, and collecting the conjugated *Bacillus*/magnetite. The invention is directed to a method for producing a *Bacillus*/magnetite conjugate, comprising contacting an isolated *Bacillus* sp, comprising a nucleic acid molecule having a polynucleotide sequence at least 90% identical, 95% identical, 98% identical, 99% identical, or 100% identical to a 16s rRNA polynucleotide of the microorganism deposited under ATCC Accession No. PTA-121034 and magnetite, and collecting the conjugated *Bacillus*/magnetite. The invention is directed to a method for producing a *Bacillus*/magnetite conjugate, comprising contacting an isolated *Bacillus* sp. comprising a nucleic acid molecule having a polynucleotide sequence at least 90% identical, 95% identical, 98% identical, 99% identical, or 100% identical to SEQ ID NO:1 and magnetite, and collecting the conjugated *Bacillus*/magnetite, in some embodiments, the *Bacillus* can be a live cell or a dead cell. In some embodiments, the dead cell is a fixed cell. A cell can be fixed by known methods, such as by, e.g., paraformaldehyde, formaldehyde, or glutaraldehyde.

The invention also includes a method for collecting algae, comprising contacting the *Bacillus*/magnetite conjugate described herein and an algae culture, and forming an algae aggregate. The method can further comprise separating the algae aggregate from the culture. The method can further comprise recovering the *Bacillus*/magnetite conjugate and reusing the *Bacillus*/magnetite conjugate to form an algae aggregate from another algae culture.

In some embodiments, the *Bacillus* is a *Bacillus* sp. that is a *Bacillus megaterium, Bacillus aryabhattai* or *Bacillus horikoshii,* In some embodiments, the *Bacillus* sp. is RP1137, deposited under the International Budapest Treaty on Feb. 28, 2014 at the American Type Culture Collection, Patent Depository, 10801 University Boulevard, Manassas, Va. 20110-2209, under ATCC Accession No. PTA-121034.

In some embodiments, the alga is *Nannochloropsis* sp., *Tetraselmis* sp. or *Chaetoceros* sp. In some embodiments, the algae can be *T. chuii, T. sucia, Phaeodactylum* sp., *N. oceanica, N. oleoabundans, C. cryptica,* or *N. angularis,* or combinations thereof. In some embodiments, the ratio of the *Bacillus* to algae cell aggregation can be 2:1 to 1:10, 1:1 to 1:5, or 1:1 to 1:2, or any ranges therein. In some embodiments, the compositions and methods described herein can be used to collect cyanobacteria.

In some embodiments, the contacting can occur at a pH of 7 or greater. The pH of the culture can be greater than 8, or 9 or greater. The salinity of the culture can be 0 ppt to 156 ppt, 20 ppt to 156 ppt, or any ranges therein. The temperature of the culture can be, e.g., 10° C. to 40° C., 10° C. to 20° C., 20° C., or any ranges therein.

In some embodiments, the culture can contain divalent cations such as, but not limited to, $Fe^{2+}$, $Ca^{2+}$, and $Mg^{2+}$, in a concentration of, e.g., a range of 1 mM to 60 mM, 50 mM, 40 mM, 30 mM, 20 mM, 10 mM, or any ranges therein. For example, the culture can contain 1 mM to 30 mM, or 1 mM to 20 mM, calcium ions.

The methods of the invention can further comprise lowering the pH of the culture to reverse the aggregation and reusing the *Bacillus* to form an algae aggregate in another algae culture.

In some embodiments, the magnetite is unoxidized powder.

In some embodiments, the algae are in an exponential phase of growth.

In some embodiments, the *Bacillus* sp. is in an exponential phase of growth.

In some embodiments, the salinity of the culture can be, e.g., 0 ppt to 300 ppt, 0 ppt to 200 ppt, 0 ppt to 160 ppt, 5 ppt to 200 ppt, or any ranges therein.

In some embodiments, the temperature of the culture can be 5° C. to 50° C., 10° C. to 40° C., 10° C. to 30° C., 10° C. to 20° C., or any ranges therein.

The invention is directed to a method of producing maghemite, comprising heating magnetite powder, and oxidizing the magnetite to form maghemite. The magnetite powder can be synthesized using known methods or commercially purchased.

The invention is directed to a composition comprising an alga and bare maghemite or bare maghemite that is not attached to a support. Bare maghemite is uncoated maghemite. Bare maghemite that is not attached to a support is not attached to or associated with additional support materials, such as, but not limited to, polymers, biopolymers such as, e.g., chitosan or chitosan acetate, and extracellular polymeric substances, such as polysaccharides, or glass.

The invention is also directed to a method for collecting algae, comprising binding algae in a culture to bare maghemite or bare maghemite that is not attached to a support, and forming an algae aggregate, wherein the binding of algae to bare maghemite is not reversible by altering the pH. The binding of algae to bare maghemite is not pH sensitive.

In some embodiments, the method can include repeating the binding of algae in the culture to the bare maghemite, e.g., to reach saturation, and increasing the algae aggregate. The repeating can be two times, three times, four times, or more.

In some embodiments, the algae can be collected in a dry weight ratio of algae:maghemite of 1:1 or more, 2:1 or more, 3:1 or more, 4:1 or more, or 1:1 to 5:1, or any ranges therein.

The algae that can be collected, flocculated, aggregated, or harvested include, but are not limited to, green algae or brown algae. The algae can be macroalgae or microalgae. The green algae can be *Nannochloropsis, Tetraselmis,* or *Scenedesmus*. The brown algae can be *Isochrysis*. The algae can be *Lemnaceae*. In some embodiments, the compositions and methods described herein can be used to collect cyanobacteria.

The culture can be a closed culture, e.g., a container or reactor, or an open culture, e.g., a pond, a lake, a bay, coastal waters, or an ocean. The culture can contain an artificial medium, e.g., growth media, or fresh, brackish or salt water.

In some embodiments, the compositions and methods of the invention can require separating suspension cultures (e.g., algae or cyanobacteria) from a media. Other embodiments can require compositions, methods and uses of a harvesting system for removing media compositions from suspension cultures. Yet other embodiments can require systems and methods for separating biomass from algae media for use in biofuel production and generation of related algal products. In some embodiments, the suspension cultures or wastewaters include, but not limited to, algae, bacteria, yeast, fungi, suspended solids in water and wastewater particulates, for removal or collection of algae therefrom.

In some embodiments of the present invention, collecting algae can require magnetic flocculation for harvesting an algae culture or algae removal from waters. For example, algae bind or be adsorbed on surfaces of the *Bacillus*, *Bacillus*/magnetite conjugate, or maghemite, as described herein, forming bacterial- and/or magnetically-linked algae complexes capable of removal from culture. In certain embodiments, the bacterial- and/or magnetically-linked algae can be separated from a media using a magnetic separator or sedimentation, such as by gravity or magnetic field. In accordance with these embodiments, magnetically-linked algae can be captured by a magnetic field (e.g., a magnet or magnetic field), concentrating the algae, and separating the algae from the culture or using other methods such as gravity.

In certain embodiments, the magnetic agents used for aggregation, flocculation or coagulation of the algae include magnetite or maghemite. Bare or uncoated magnetite or maghemite are used, having a purity level of at least 70%, 80%, 90%, 95%, 99%, or 100% by weight.

In some embodiments, magnetic flocculation for harvesting the algae can be performed without base addition and adjustment of the pH, in contrast to other methods known in the art, which require adjusting the pH to induce flocculation, such as a high pH (e.g., about 8.5 to about 11.5, about 9.0 to about 11.0, about 9.5 to about 10.5). The invention does not require cultures or wastewaters in combination with magnetic or heavy particles at a basic pH for precipitation/concentration followed by a more neutral or slightly acidic pH to allow separation of the algae aggregate from the cultures.

In some embodiments, the magnetic particles can be collected and regenerated for use in another culture or waste water. In other embodiments, continuous culturing, and optional concentrating, techniques disclosed herein can be used for cost effective and rapid harvesting.

In some embodiments, the cultures contain algae, but can also contain bacteria, e.g., cyanobacteria, fungi or yeast. Products contemplated herein for production from the algal yields can include, but are not limited to, biofuels, nutraceuticals, nutritional lipids, protein, vitamins, carbohydrates, and/or amino acids.

The inventions described herein can be used to alleviate or reduce generation of sludge, algae blooms, or other algae problems associated with water and wastewater clean-up or contaminant removal.

Algal strains contemplated for collecting, harvesting or concentration herein can include, but are not limited to, *Phaeodactulum tricornutum, Chlorella protothecoides, Nannochloropsis salina, Nannochloropsis sp, Tetraselmis succica, Tetraselmis chuii, Botrycoccus braunii, Chlorella sp., Chlorella ellipsoidea, Chlorella emersonii, Chlorella minutissima, Chlorella salina, Chlorella protothecoides, Chlorella pyrenoidosa, Chlorella sorokiniana, Chlorella vulgaris, Chroomonas salina, Cyclotella cryptica, Cyclotella sp., Dunaliella salina, Dunaliella bardawil, Dunaliella tertiolecta, Euglena gracilis, Gymnodinium nelsoni, Haematococcus pluvialis, Isochrysis galbana, Monoraphidium minutum, Monoraphidium sp., Neochloris oleoabundans, Nitzschia laevis, Onoraphidium sp., Pavlova lutheri, Phaeodactylum tricornutum, Porphyridium cruentum, Scenedesmus obliquuus, Scenedesmus quadricaula Scenedesmus sp., Stichococcus bacillaris, Spirulina platensis, Thalassiosira sp.* or combinations thereof.

*Bacillus*/magnetite conjugate or maghemite particles can bind algae to provide a magnetic property, resulting in algal movement/attraction under a magnetic field. In addition, particle-algae complexes can have a higher density than non-particle algae. For example, magnetite density can be about 5.0 g/cm$^3$ to about 5.5 g/cm$^3$. In certain embodiments, some heavier flocculated algae can settle out of solution by gravity with or without magnetic flocculation. This process can produce less sludge in the flocculation process.

Unlike some methods known in the art, which require a solid matrix of additional materials, such as solid foam and/or glass particles, the methods according to the invention can use *Bacillus*/magnetite conjugate or bare maghemite, without the need for additional support materials. The magnetite or maghemite is bare or uncoated.

The inventions described herein can be used in an open culture, e.g., is a pond, a lake, a bay, coastal waters, or an ocean, as no other chemicals, polymers, etc. are needed to practice the methods. Thus, clean-up of algae in the open waters can be easily facilitated without additional environmental harm caused by chemicals, polymers, etc. The inventions can also be used in a closed culture, e.g., small-scale or large-scale vessels. In some embodiments, the algae aggregate formed by contact with the *Bacillus*/magnetite conjugate or bare maghemite can be obtained in continuous processes in which the magnetizable aggregate is separated off from the culture, the *Bacillus*/magnetite conjugate or bare maghemite separated from the algae, and returned to the process again. This method makes it possible to collect algae continuously from a culture without the process needing to be interrupted.

In some embodiments, the methods can be carried out with reactors which have a reaction chamber. The reactor can be operated batch-wise or also continuously. By a batch-wise operation is meant that the reaction chamber is filled with a specific quantity of the algae culture, the algae culture is converted to an algae aggregate, the algae aggregate is optionally removed from the reaction chamber and the algae culture is worked up. The algae culture can be introduced in its entirety at the start of the conversion. However it is also possible to introduce only a part-quantity of the algae culture at the start of the conversion and to feed further part-quantities of algae culture into the reactor at time intervals ("fed-batch"). The concentration of algae culture and algae aggregate changes over time as the process proceeds. If live *Bacillus* cells are used, their concentrations will likewise changes as a result of their multiplication during the reaction.

The method of operating the reactor is not in principle subject to any limitations. It is for example possible to use a tank-shaped reactor, for example an agitated tank reactor in which the reactor content is moved continuously or in phases in order to homogenize the reactor content. However, it is also possible to use a tubular reactor type, for example a tube reactor in which the substrate is passed through the reaction chamber in a plug-shaped or turbulent stream.

The reactor can be provided with customary equipment. For example it can be provided that the reactor can be thermostatted, thus a cooling or a heating is provided. Inlets and outlets with which a substrate can be fed or a product removed can be provided on the reactor. A stirrer with which the reactor content can be moved and mixed can be provided. Furthermore, devices can be provided for measuring temperature, pressure or various other process parameters such as, e.g., pH. There are no limits per se to the design of the bioreactor or of the reaction chamber arranged therein. In particular for reactions which take place under anaerobic conditions, e.g., in the production of biogas, the reaction chamber is preferably designed closed.

The algae culture can contain customary components, for example buffer systems, trace elements, cofactors or salts. The concentration of the individual constituents of the substrate mixture is chosen depending on the reaction carried out within customary ranges.

The inventions described herein are useful at all ranges of pH, without the need for adding acid or base for the binding of the magnetic agent to the algae. If, in some embodiments, the pH can be in the neutral range, acidic range, or alkaline range, such as, e.g., pH 1 to 10, pH of 6 or less, pH of 6 or greater, pH of 7 or less, pH of 7 or greater, pH 4 to 9, pH 6 to 8, or any ranges therein.

The methods can be used to collect or separate algae from complex mixtures such as, e.g., waste water or sewage sludge, etc.

The magnetic agents, magnetite and maghemite, are bare or uncoated, i.e., do not need to be coated by, e.g., polycaprolactone or poly-3-hydroxybuturate or e.g. alginate or the like on the surface of the magnetizable support by enclosing them in the polymer matrix. The surface of the magnetic agent does not need to be chemically modified/coated in order to facilitate the attachment of algae.

In some embodiments, the magnetizable algae aggregate according to the invention can be separated from the culture or product mixture with a magnetic separation device. All magnetic separation devices known per se can be used as magnetic separation device. For example, permanent magnets which can be arranged stationary or movable in or at the separation device are suitable. However, similarly, e.g., electromagnets can also be used. Stationary magnets collect the magnetizable aggregate at a specific location in the separation device, while movably arranged magnetic separation devices can transport the magnetizable aggregate after separation, for example to a specific location, and collect it there. For this, for example a permanent magnet can be displaced along an outer wall of a separation tube. Once the magnetizable algae aggregate has been separated from the culture with the help of the magnetic separation device, it can be collected, e.g., by switching off the magnetic separation device with the result that the magnetizable algae aggregate, e.g., is detached again from a wall of the magnetic separation device and, e.g., can be rinsed and collected.

The magnetic separation device can be arranged in the reaction chamber itself, e.g., as an encased rod-shaped magnet. However, it is also possible to provide the separation device outside the reaction chamber and to transfer the algae aggregate from the reaction chamber into the magnetic separation device. The magnetic separation device can be located in the outlet of the reactor.

In some embodiments, the magnetizable agent can have a relatively small diameter so that a high surface area is produced on which the algae can bind. In some embodiments, the average particle diameter by mass ($D_{50}$) of the magnetizable agent can be 500 µm or less, e.g., greater than 10 µm to 500 µm, 300 µm or less, 200 µm or less, 100 µm or less, 50 µm or less, 40 µm or less, 30 µm or less, 20 µm or less, 10 µm or less, 5 µm or less, 2 µm or less, 1 µm or less, 0.5 µm or less, as nanoparticles, or any ranges therein. Alternatively, the $D_{50}$ of the magnetizable agent can be greater than 0.5 µm, greater than 1 µm. In some embodiments, the diameter of the support is less than 2 mm, according to another embodiment less than 1 mm. The $D_{50}$ can be ascertained for example by screen analysis. Suitable methods are given for example in DIN 66165-1 and -2. Alternatively the average particle size can be measured by means of laser diffraction. Suitable methods are described in ISO 13320:2009. In the case of larger particles (>100 µm) the particle size distribution can be ascertained for example by means of screen analysis. For smaller particles, the average particle diameter can be measured by laser diffractometry.

The magnetite and maghemite can also be formed by nanoparticles, which can have superparamagnetic properties. In some embodiments, the $D_{50}$ of the nanoparticles can be a range of from 1 nm to 1 µm. In order to have superparamagnetic properties the size of the magnetizable particles can be 1 nm to 10 nm. The particle size of the magnetizable particles can be suitably determined after the grinding of the starting materials.

The magnetic particles can have a spherical shape. However, it is also possible to have a different geometric shape, e.g., an irregularly shaped three-dimensional body.

The quantity of the magnetizable aggregate provided in the substrate mixture is chosen depending on the conditions under which the method according to the invention is carried out. Relative to the weight of the dry organic substrate the quantity of the magnetizable aggregate according to an embodiment is chosen in the range of from 1 to 70 wt. %, according to a further embodiment in the range of from 1 to 20 wt. % and according to yet another embodiment in the range of from 2 to 5 wt. %.

The *Bacillus* or magnetizable particles separated off from the algae aggregate can be recovered and optionally used for another algae culture.

All available methods can be used to return the separated magnetizable aggregate to the reaction chamber or algae culture. The return can be carried out continuously or portionwise by, for example, firstly collecting a specific quantity of magnetizable aggregate and then returning this to the reaction chamber. The return can be automated. However, it is also possible to carry out the return manually. The advantages of the method according to the invention are evident in particular in fermentations with slow-growing microorganisms.

According to some embodiments, the magnetite or maghemite particles have a magnetic mass susceptibility in the range of $5 \times 10^{-9}$ to $3.7 \times 10^{-7}$ m$^3$/kg.

By reducing the field strength, starting from the magnetic saturation, to the value of zero, a residual magnetization remains. This is measured in millitesla (mT). The residual magnetism then completely disappears if a magnetic force which is oppositely poled to the original field is applied to the material with the field strength Hc (coercive field strength).

A magnetic particle can be formed by a superparamagnetic substance. After switching off an external magnetic field, a superparamagnetic substance no longer displays any residual magnetism. A suitable superparamagnetic substance is, e.g., in the form of nanoparticles.

In some embodiments, the magnetizable areas are formed by a ferrimagnetic material. After switching off an external magnetic field, ferrimagnetic materials display only a low residual magnetism. Suitable ferrimagnetic materials include magnetite and maghemite.

The particulate magnetizable particles contained in the magnetizable aggregate according to the invention preferably has a bulk density in the range of from 100 to 1000 kg/m$^3$, according to an embodiment a bulk density in the range of from 200 to 800 kg/m$^3$ and according to a further embodiment a bulk density from 300 to 600 kg/m$^3$. The bulk density can be ascertained according to DIN EN 13055-1.

Both magnetite ($Fe_3O_4$), and maghemite (gamma-$Fe_2O_3$) are ferrimagnetic materials. These can be distinguished from ferromagnetic materials by the spinel structure and the oxidic chemistry.

Soft ferrimagnetic materials can be used for producing the magnetizable particles, as they largely lose their magnetization after the magnetic field is switched off and thus form no agglomerates.

The algae culture can have a high water content. In some embodiments, the water content of the algae culture can be 50 wt. % to 99 wt. %.

The aggregation time of the algae culture in the presence of the *Bacillus*, *Bacillus*/magnetite conjugate, or maghemite is, e.g., 1 second or less, 2 seconds or less, 3 seconds or less, 10 seconds or less, 1 minute or less, 1 hour or less, 2 hours or less, or 1 day or less, 3 to 28 days, or 40 days or less, three months or less, or any ranges therein.

The method can be carried out in a single reactor. However, it is also possible to connect several reactors in series and to operate the method in several stages. The different stages of the method can then be optimized to specific parameters.

The magnetic particles described herein have been used successfully with algae from a photobioreactor (closed growth system) and on algae from open water (pond). The harvesting system allows harvesting from natural bodies of water including lakes, ponds and the open ocean which is different from other harvesting systems. It also allows harvesting in more traditional algal cultivation systems such as photobioreactors and raceway ponds.

The maghemite particles can be used to harvest algae from any body of water, be it natural or artificial. They can be used to harvest farmed algae for the production of fuel or other products. Another use is for the harvest of algae for high value products such as pigments. They can be used for remediating harmful algal blooms in natural water ways or to remove nuisance algal blooms. The biomass from the blooms can be used for production of fuel, high value products for drug discovery (many algae produce potent compounds), aquaculture feed and for fertilizer.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

EXAMPLES

Example 1

Isolation Method

Aggregating strain *Bacillus* sp. RP1137 was discovered as a co-occurring bacterium in experiments investigating the ability of bacterial species to aggregate *Nannochloropsis* sp. IMET1, a microalgal strain with potential in biofuel production. *Bacillus* sp. RP1137 was isolated in pure culture and assayed alone for its ability to aggregate microalgae. By using pure cultures of strain RP1137 in aggregation assays it was possible to attribute the aggregation ability solely to this novel bacterial isolate.

Identification

To identify strain RP1137, we sequenced its 16S rRNA gene. The sequence of this gene acts as a barcode for identifying bacteria and allows us to determine its closest relative based on the degree of sequence homology to other known bacteria. The aggregating bacterium is closely related to several *Bacillus* sp., specifically its 16S rRNA gene has 99% sequence homology to *Bacillus megaterium*, *Bacillus aryabhattai* and *Bacillus horikoshii*. The 1% difference in sequence suggests that, with supporting data, it may be possible to designate this strain as a new species. The almost full-length 16S rRNA gene sequence of this bacterial strain is shown below.

```
16S rRNA gene sequence 5' -> 3' (1483 bp)
                                         (SEQ ID NO: 1)
CAGGATGAACGCTGGCGGCGTGCCTAATACATGCAAGTCGAGCGAACTGA

TTAGAAGCTTGCTTCTATGACGTTAGCGGCGGACGGGTGAGTAACACGTG

GGCAACCTGCCTGTAAGACTGGGATAACTTCGGGAAACCGAAGCTAATAC

CGGATAGGATCTTCTCCTTCATGGGAGATGATTGAAAGATGGTTTCGGCT

ATCACTTACAGATGGGCCCGCGGTGCATTAGCTAGTTGGTGAGGTAACGG

CTCACCAAGGCAACGATGCATAGCCGACCTGAGAGGGTGATCGGCCACAC

TGGGACTGAGACACGGCCCAGACTCCTACGGGAGGCAGCAGTAGGGAATC

TTCCGCAATGGACGAAAGTCTGACGGAGCAACGCCGCGTGAGTGATGAAG

GCTTTCGGGTCGTAAAACTCTGTTGTTAGGGAAGAACAAGTACGAGAGTA

ACTGCTCGTACCTTGACGGTACCTAACCAGAAAGCCACGGCTAACTACGT

GCCAGCAGCCGCGGTAATACGTAGGTGGCAAGCGTTATCCGGAATTATTG

GGCGTAAAGCGCGCGCAGGCGGTTTCTTAAGTCTGATGTGAAAGCCCACG

GCTCAACCGTGGAGGGTCATTGGAAACTGGGGAACTTGAGTGCAGAAGAG

AAAAGCGGAATTCCACGTGTAGCGGTGAAATGCGTAGAGATGTGGAGGGA

ACACCAGTGGCGAAGGCGGCTTTTTtGGTCTGTAACTGACGCTGAGGCGC

GAAAGCGTGGGGAGCAAACAGGATTAGATACCCTGGTAGTCCACGCCGTA

AACGATGAGTGCTAAGTGTTAGAGGGTTTCCGCCCTTTAGTGCTGCAGCT

AACGCATTAAGCACTCCGCCTGGGGAGTACGGTCGCAAGACTGAAACTCA

AAGGAATTGACGGGGGCCCGCACAAGCGGTGGAGCATGTGGTTTAATTCG
```

-continued

```
AAGCAACGCGAAGAACCTTACCAGGTCTTGACATCCTCTGACAACTCTAG

AGATAGAGCGTTCCCCTTCGGGGACAGAGTGACAGGTGGTGCATGGTTG

TCGTCAGCTCGTGTCGTGAGATGTTGGGTTAAGTCCCGCAACGAGCGCAA

CCCTTGATCTTAGTTGCCAGCATTCAGTTGGGCACTCTAAGGTGACTGCC

GGTGACAAACCGGAGGAAGGTGGGGATGACGTCAAATCATCATGCCCTT

ATGACCTGGGCTACACACGTGCTACAATGGATGGTACAAAGGGCTGCAAG

ACCGCGAGGTCAAGCCAATCCCATAAAACCATTCTCAGTTCGGATTGTAG

GCTGCAACTCGCCTACATGAAGCTGGAATCGCTAGTAATCGCGGATCAGC

ATGCCGCGGTGAATACGTTCCCGGGCCTTGTACACACCGCCCGTCACACC

ACGAGAGTTTGTAACACCCGAAGTCGGTGGAGTAACCGTAAGGAGCTAGC

CGCCTAAGGTGGGACAGATGATTGGGGTGAAGT
```

Aggregation of Microalgae

Upon addition of the bacterial strain (*Bacillus* sp. RP1137) and mixing, the algae immediately form large aggregates that fall out of suspension within seconds. This can clearly be seen in FIG. 1, which shows the aggregation process over 30 seconds. In FIG. 2, algal aggregation was quantified by measuring the change in algal chlorophyll fluorescence with and without the addition of *Bacillus* sp. RP1137. Because the *Bacillus* strain does not fluoresce, the reduction in fluorescence can be directly attributed to a reduction in suspended algae. Aggregation has been tested with several algal species and shown to work effectively with the algae *Nannochloropsis* sp. IMET-1, *Tetraselmis* sp. and *Chaetoceros* sp. These results are significant for several reasons. The first is the speed of aggregation, which is faster than simple chemical flocculation with NaOH and also produces bigger flocs that make separation of algae from water easier. The speed of the interaction implies the oil content of the algae should be unaffected by the harvest method. Another important advantage of this bacterial strain is the range of algae it can aggregate. The algae that can be aggregated by this bacterium are distantly related meaning the mechanism of aggregation is likely nonspecific and it will work with many algal strains. The bacterium could be used, for example, to harvest algae in many algal biofuel systems currently under development and also for the harvest of higher value algal commodities such as nutraceuticals, and pigments.

Example 2

Fossil fuels have provided the energy to drive development in the modern world. Most of the energy used in the United States comes from fossil fuels, including crude oil, coal, and natural gas (1 (full citations for numbered citations are provided at the end of the Examples)). Our energy infrastructure, particularly transportation, is built around the availability of liquid fuels, meaning that at least in the near term, a suitable sustainable replacement to fossil oil is desirable. Biofuels have been proposed as a means to switch from the current extractive means of liquid fuel generation to a sustainable form of liquid fuel generation.

First-generation biofuels are derived from food crops by converting corn and sugarcane into ethanol. Production of biofuels has been spurred by the Renewable Fuel Standard, which requires the production of 136 billion liters of renewable fuel by 2022 (2). The act that established this standard also requires the fuels produced to have a lower carbon footprint than the petroleum fuels that they replace (2). Second-generation biofuels are derived from cellulose, which is converted to ethanol. The cellulose can come from a variety of sources, including corn stover, wood, and switchgrass. Fuels from algae are often listed as the third and perhaps most promising iteration of biofuels due to several advantages over other biofuels. The term alga-derived biofuels refers to the production of biodiesel from algal lipids, as opposed to ethanol derived from first and second-generation approaches. Biodiesel can also be generated from oils extracted from canola, soy, and palm oils (3); however, chief among the advantages of algae is the productivity that is possible per unit area, with some algae being able to double their biomass in a few hours. Biofuels are based on converting biomass to fuel, so greater biomass productivity translates to greater fuel productivity. Other advantages of algae are the ability to grow in salt water or wastewater and to grow on land not suited for agriculture (4, 5). Algae can also be harvested multiple times per season, unlike many land-based crops (3).

Microalgae are promising candidates for producing renewable liquid fuels; however, several barriers must be reduced before large-scale production can be economically viable. It is important to note that these challenges are technical and economic in nature, as the process of creating biofuels from algae is proven. These barriers include supplying sufficient nutrients and $CO_2$ to the algae as well as mixing and controlling the pH in the large facilities needed to produce significant amounts of biofuel (6). Other challenges come from a systems perspective, where the reliability of production must be improved (6). The risk associated with inconsistent production stems from the presence of algal grazers as well as infections by bacteria or viruses, which can lower productivity or even result in the rapid decline of algal cultures.

We have focused on the harvest step of algal biofuel production because this step must be improved for algal biofuels to become economically viable. In an analysis done by Richardson et al., harvesting was the number one operating expense and number two capital expense in an outdoor production system (6). Harvesting microalgae efficiently and cheaply is one of the biggest challenges for algal biofuels. Even in dense algal cultures, the biomass represents only a few grams per liter of water. This water must be removed before the biomass can be converted into fuel. Several strategies have been developed to concentrate algae, including filtration, centrifugation, sedimentation, dissolved air flotation, electrocoagulation, chemical flocculation, and bio-aggregation (7). Each method has advantages and disadvantages with respect to cost, throughput, and posttreatment effects on both water and biomass, as reviewed in detail by Uduman et al. (7).

Bioaggregation can be achieved using biopolymers, such as chitosan (8-10), and extracellular polymeric substances, such as polysaccharides (11, 12). In this study, a bacterium designated *Bacillus* sp. strain RP1137 was isolated and identified, capable of rapidly aggregating microalgae that are candidates for biofuel production. The conditions were characterized under which aggregation is effective and the range of algae which the bacterium can aggregate.

Materials and Methods

Strains and Culture Conditions.

The bacterial strain *Bacillus* sp. RP1137 was grown in marine broth 2216 (BD, Franklin Lakes, N.J.) at 30° C. in 125-ml Erlenmeyer flasks with shaking at 180 rpm. Solid medium was prepared from marine broth 2216 by addition of 15 g/liter Difco technical agar (BD).

*Nannochloropsis oceanica* IMET1 was grown in f/2 medium (18) with a salinity of 20 ppt. This alga has been maintained for 10 years at the Institute of Marine and Environmental Technology by the Aquaculture Research Center in Baltimore, Md. The algae were grown in photobioreactors which consisted of 500-ml borosilicate glass bottles (Pyrex no. 1395; diameter, 13.6 cm; height, 26.2 cm) with three ports in the cap. Two ports were connected to tubes leading to the bottom of the bottle. Air was pumped into these two ports through 0.22-μm-pore-size syringe filters at a rate of 5 liters/min to provide constant mixing and to provide the carbon dioxide present in the air. The third port was used as a vent. The bottles were positioned 25 cm from 215-W Phillips white fluorescent lights with a light intensity of 275 μmol/m$^2$/s at the front of the bottle and were grown on a light-dark photoperiod of 14 and 10 h, respectively, at 25° C. Algae were subcultured weekly using an inoculating volume of 10% and were used for the experiments at an optical density at 600 nm ($OD_{600}$) of 1.0 and a pH of 10.2.

*Tetraselmis chuii, Tetraselmis sucia*, and a *Phaeodactylum* sp. were grown using the same setup described above and were also grown in f/2 medium. Cells were grown in 250-ml Erlenmeyer flasks at 180 rpm with shaking at 20° C. and with a light-dark photoperiod of 14 and 10 h, respectively.

*Neochloris oleoabundans* MK8520 was grown in *Neochloris* medium. This medium was composed of 5.82 g/liter NaCl, 2.47 g/liter $MgSO_4.7H_2O$, 1 g/liter $KNO_3$, 0.75 g/liter KCl, 66 mg/liter $CaCl_2$, 1.24 g/liter $H_3BO_3$, 4.2 g/liter $NaHCO_3$, 0.109 g/liter $KH_2PO_4$, 10 μg/liter thiamine HCl, 50 μg/liter biotin, 50 μg/liter vitamin $B_{12}$, 0.24 mg/liter $Na_2MoO_4.2H_2O$, 6.6 mg/liter $FeCl_3$, 0.1 mg/liter $CuSO_4.5H_2O$, 0.08 mg/liter $CoCl_2.6H_2O$, 3.2 mg/liter $MnCl_2.4H_2O$, 0.22 mg/liter $ZnCl_2$, and 40 mg/liter $Na_2EDTA$. Cells were grown in 250-ml Erlenmeyer flasks at 180 rpm with shaking at 20° C. and with a light-dark photoperiod of 14 and 10 h, respectively.

*Nitzschia angularis* MK8708 was grown in 100% Instant Ocean medium. This medium was composed of 35 g/liter Instant Ocean, 0.75 g/liter $NaNO_3$, 0.3 g/liter $Na_2SiO_3.9H_2O$, 15 mg/liter $NaH_2PO_4$, 20 mg/liter $Fe_2SO_4.7H_2O$, 17 mg/liter $Na_2EDTA$, 34.2 mg/liter $H_3BO_3$, 4.3 mg/liter $MnCl_2.4H_2O$, 0.3 mg/liter $ZnCl_2$, 0.13 mg/liter $CoCl_2.6H_2O$, 0.025 mg/liter $NaMoO_4.2H_2O$, 0.01 mg/liter $CuSO_4.5H_2O$, 0.26 mg/liter $NiSO_4.6H_2O$, 0.3 mg/liter vitamin B12, 6 mg/liter thiamine, and 0.3 mg/liter biotin. Cells were grown in 250-ml Erlenmeyer flasks at 180 rpm with shaking at 20° C. and with a light-dark photoperiod of 14 and 10 h, respectively.

*Cyclotella cryptica* MK89172 was grown in 50% Instant Ocean medium. This medium is the same as the 100% Instant Ocean medium listed above, except that 17.5 g/liter instead of 35 g/liter of Instant Ocean was used and the medium was supplemented with 8 g/liter glucose. Cells were grown in 250-ml Erlenmeyer flasks at 180 rpm with shaking at 20° C. and with a light-dark photoperiod of 14 and 10 h, respectively.

16S rRNA Gene-Based Strain Identification.

To identify the aggregating strain, 16S rRNA gene PCR was performed using primers 27f and 1492r (19), and RP1137 cells were added directly to the PCR mixture as the DNA template. Cycling conditions were one cycle at 95° C. for 3 min; 30 cycles of 95° C. for 30 s, 46° C. for 30 s, and 72° C. for 90 s; and then one cycle of 72° C. for 5 min. The ca. 1,465-bp product was purified using a Qiagen QIAquick PCR purification kit. The purified PCR product was sequenced using primers 27f, 1492r, 700f (GTGK-AGCRGTGAAA) (SEQ ID NO:2), and 700r (CTA CGCATTTCACY) (SEQ ID NO:3) to obtain full-length double-stranded sequence. The closest match for RP1137's 16S rRNA gene sequence was identified using NCBI's BLASTn algorithm.

Filtration Aggregation Assay.

Aggregation data were collected using a filtration aggregation 96-well assay. This assay was developed to allow testing of multiple parameters with replicates in a 96-well plate. Filtration rigs were built by sandwiching a 50 μm mesh between two pipette tip racks (Tip One; USA Scientific) and sealing this mesh in place with silicon. The resultant apparatus was designated a "filtration rig." The filtration rig fit neatly in a 96-well plate and retained aggregates on the mesh, while nonaggregated algal cells (diameter, 2 to 3 μm) passed through into the wells of the microtiter plate. In a typical aggregation experiment, 150 μl of algae at 1×10$^7$ cells/ml was pipetted into a round-bottom 96-well plate. A 100-fold-concentrated bacterial suspension (1.5 μl; original density, 1×10$^7$ cells/ml) was added to the algae in the designated wells to give a 1:1 alga-to-bacterium ratio. Wells not receiving bacteria served as negative controls for aggregation induced by the addition of bacteria. The plate was sealed with Parafilm, and the contents were mixed by vortexing for 1 min. A filtration rig was placed on a round-bottom 96-well plate, and the 150 μl containing the aggregates was pipetted from the first microtiter plate into the top of the filtration rig using wide-bore pipette tips. The plate and rig were centrifuged at 100×g for 10 s to ensure that the entire volume in the rig passed through the mesh into the second, lower 96-well plate. At this point, the aggregates were retained on the mesh and the nonaggregated cells had passed into the second plate. The algae in the second plate were suspended and diluted into the linear range for chlorophyll fluorescence measurement in a Spectromax M5 microplate reader. Chlorophyll fluorescence was measured with an excitation wavelength of 488 nm, a 515 nm-cutoff filter, and an emission wavelength of 685 nm. From these data, the percentage of algae that had aggregated and remained on the mesh was calculated from the fluorescence of the algae that were not aggregated using the formula $P=[1-(A/N)]\cdot 100$, where P is the percentage of algae aggregated, A is the fluorescence of the filtrate from the aggregated sample, and N is the fluorescence of the filtrate from the nonaggregated sample.

Fluorescence Microscopy.

Microscopy was used to visualize the structure of the bacterial-algal aggregates. A 1-ml aliquot of *Bacillus* sp. RP1137 was stained with 2.5 μl of SYBR green I nucleic acid stain for 10 min in the dark. The bacteria were concentrated by centrifugation at 13,000×g for 2 min, and the cell pellet was suspended in 10 μl of fresh medium, giving a 100-fold concentration of the bacteria. An 8-μl portion of this suspension was added to 800 μl of *Nannochloropsis* cells in f/2 medium at an $OD_{600}$ of 1.0, and the components were mixed. Aggregates were pipetted onto a slide and visualized using laser scanning confocal microscopy with a Zeiss Axioskop microscope and a Bio-Rad Radiance 2100 laser light source. Both algal chlorophyll and SYBR green I-stained bacteria were excited with a 488-nm argon laser. The SYBR green I signal was visualized using a 415/30-nm band-pass filter, and the chlorophyll autofluorescence was visualized with a 600-nm long-pass filter. Controls comprising bacteria only and algae only were used to ensure that there was no cross bleeding of signals between the two channels.

Temperature Dependence.

To determine the effect of temperature on aggregation, 150 µl of algae was transferred into PCR tubes. The PCR tubes were placed in a thermocycler to hold the algal suspensions at 10, 20, 30, or 40° C. These temperatures were chosen because they represent the range of temperatures likely to occur in an outdoor algal production pond. The algae at $1\times10^7$ cells/ml were incubated for 10 min to ensure that they reached the set temperatures. To half of the tubes at a given temperature, 1.5 µl of 100-fold-concentrated RP1137 cells (original density, $1\times10^7$ cells/ml) was added and the components were mixed by vortexing. The other half of the tubes served as no-aggregation controls. All samples were transferred to the top of the filtration aggregation rig, and the assay was continued as described above.

Salinity Dependence.

The salinity dependence of aggregation was determined by harvesting a 5-ml aliquot of algae at 5,580×g for each salinity tested. Half of the supernatant was removed (2.5 ml). *Nannochloropsis* was grown in 20-ppt salinity. To get 10-ppt salinity, 2.5 ml of distilled $H_2O$ (d$H_2O$) was added; for 20-ppt salinity, 2.5 ml of 20-ppt NaCl was added; for 30-ppt salinity, 2.5 ml of 40-ppt NaCl was added; for 40-ppt salinity, 2.5 ml of 60-ppt NaCl was added; and for 156-ppt salinity, 2.5 ml of 292-ppt NaCl was added. For the 0-ppt-salinity sample, the cell pellet was suspended in d$H_2O$ and the pH was adjusted to match that of the other samples (pH 10.2). The last sample had an effective salinity of 0.005 ppt due to the NaOH used to adjust the pH. After salinity adjustment, the filtration aggregation assay was carried out to quantify the effect of salinity on aggregation.

pH Dependence.

The pH dependence of aggregation was determined by adjusting the pH of a 200-ml aliquot of *Nannochloropsis* at $1\times10^7$ cells/ml in a beaker with constant stirring. The pH was adjusted with either 5 M NaOH or 5 M HCl; concentrated base or acid was used to limit changes in algal cell concentration. When pH stabilized at a desired value, 150 µl of the algal suspension was quickly pipetted into a 96-well plate. An overnight culture of *Bacillus* sp. RP1137 with a density $1\times10^7$ cells/ml was 100-fold concentrated, and 1.5 µl of the concentrate was added to half of the wells. The other half of the wells served as 0% aggregation negative controls. The filtration aggregation assay was carried out, and a final pH measurement was taken to ensure that the pH had not shifted significantly during the assay. This process was repeated for each pH tested.

Viability Dependence.

Two 5-ml portions of algae and two 5-ml portions of bacteria were used. To one algal sample and one bacterial sample, 5 ml of 8% paraformaldehyde (PFA; pH 7) was added and the components were mixed. To the other algal and bacterial samples, 5 ml of d$H_2O$ was added. All samples were then incubated at room temperature for 1 h with mixing every 15 min. All samples were then harvested by centrifugation at 5,580×g for 5 min. The supernatants were aspirated, and the algal samples were suspended in 5 ml of cell-free spent algal medium from the original algal culture. Bacterial samples were suspended in 5 ml of marine broth 2216. All samples were again concentrated by centrifugation, aspirated, and suspended. The algae were suspended in 5 ml to keep their original concentration, while the bacteria were suspended in 50 µl to give a 100-fold concentration. Aliquots (150 µl) of the algae at $1\times10^7$ cells/ml were transferred to a 96-well plate, and 1.5 µl of the concentrated bacteria per well (original density, $1\times10^7$ cells/ml) was used for aggregation experiments. The filtration aggregation assay was followed to complete quantitation of aggregation with the live and dead cells.

Cell Ratio.

For cell ratio experiments, the concentrations of bacteria and algae were determined using an Accuri C6 flow cytometer. Medium that had been filtered through a 0.22-µm-pore-size filter was used to grow both the algae and the bacteria. The same medium was used as the blank for determining the correct parameters for detecting cells. Chlorophyll fluorescence was used as the cutoff for gating algal cells. A forward-scatter-area cutoff of greater than 5,000 was used for gating RP1137 cells and excluded noncellular debris found in both sterile-filtered (pore size, 0.22 µm) marine broth 2216 and the RP1137 cultures. The algal cell concentration and volume (150 µl) were held constant in all wells in the 96 well-plate, while the concentration of the bacteria added was adjusted. The bacterial volume added was held constant. The bacterial culture was either concentrated by centrifugation or diluted to achieve the bacterium-alga ratios tested of 25:1, 5:1, 1:1, 1:5, 1:25, and 1:125. As before, 1.5 µl of concentrated bacteria was added to each well, and the filtration aggregation assay was used to quantify the percentage of algae that were aggregated.

Aggregation of Other Algae.

*T. chuii*, *T. sucia*, a *Phaeodactylum* sp., *N. oleoabundans* MK8520, *C. cryptica* MK89172, and *N. angularis* MK8708 were grown until the pH of cultures was between 9.5 and 10. The strains were tested using the filtration aggregation assay as described above.

Filament Shearing Assay.

RP1137 cells were split into two portions. One portion served as the control, and the other portion was sheared by passing the cells through a 28.5-gauge needle 80 times. The cells were then tested using the filtration aggregation assay as described above.

Proteinase K Digestion Assay.

RP1137 cells were digested with 100 µg/ml proteinase K in 1× phosphate-buffered saline (PBS) buffer at pH 7.4. Nondigested samples were incubated in 1×PBS. Samples were incubated for 2 h at room temperature or 50° C. The bacteria were then washed twice with 1×PBS to remove the proteinase K and then tested using the filtration aggregation assay.

Carbohydrate Inhibition Assay.

Glucose, galactose, mannose, and lactose were individually added to aliquots of *Nannochloropsis* cells at concentrations ranging from 200 to 800 mM. RP1137 cells were added to these algal aliquots to assay the effectiveness of each carbohydrate at inhibiting aggregation.

$Ca^{2+}$ and $Mg^{2+}$ Dependence Assay.

*Nannochloropsis* and RP1137 cells were washed three times in pH 10.3 deionized water. The washing procedure involved concentrating the cells via centrifugation, followed by aspiration of the supernatant and resuspension of the cells in pH 10.3 deionized water. A 0.5 M stock of $CaCl_2$ or $MgSO_4$ was added to the algae to obtain the final $Ca^{2+}$ or $Mg^{2+}$ concentrations of 0.125, 0.25, 0.5, 1, 2, 4, 8, and 16 mM. The algal solution containing the metal ions was then tested using the filtration aggregation assay with RP1137 cells.

Nucleotide Sequence Accession Number.

The GenBank accession number for the 16S rRNA gene sequence from *Bacillus* sp. RP1137 is KF015297.

Results

Isolation of an Alga-Aggregating Bacterium.

An environmental bacterium that was able to rapidly aggregate algae was isolated from a *Nannochloropsis oceanica* IMET1 aggregation experiment. When this bacterium was added to *Tetraselmis* cultures and mixed, it quickly aggregated the algae, with most of the algae settling out of solution in large aggregates in 30 s (FIG. 1). This new strain was serendipitously found as a contaminant in a broth culture of HW001, a bacterium previously reported to have the ability to aggregate algae (16). The contaminant was isolated into pure culture and was shown to have an ability to aggregate algae superior to that of HW001. The 16S rRNA gene of this new isolate was PCR amplified and sequenced. The sequence was identified using BLASTn and was found to have a 99% sequence identity to *Bacillus megaterium* strain PPB7. This aggregating strain was designated *Bacillus* sp. RP1137. Previous work by Wang et al. showed that bacteria whose 16S rRNA sequence matches the 16S rRNA sequence of *Bacillus* sp. RP1137 are not present in *Nannochloropsis* cultures, and indeed, no bacteria within the phylum *Firmicutes* were found (16), indicating that it is unlikely that RP1137 is a major component of the natural algal bacterial community. The original cryopreserved stock of HW001 was examined and found to be pure. Comparison of the 16S rRNA gene sequences to all sequences derived from culture-based and culture-independent analyses in the laboratory revealed no matches. *Bacillus megaterium* species can be found in seawater, freshwater, and soil (20), suggesting that the environment where the strain originated will likely remain unknown.

To investigate the nature of the aggregates formed when *Bacillus* sp. RP1137 was added to *Nannochloropsis* cultures, the aggregates were visualized by laser scanning confocal microscopy. Visualization of the microstructure of the aggregates was done to help elucidate the mechanism of aggregation. The bacteria in these images are filamentous and are intercalated between algal cells (FIG. 3). In general, the bacteria are mostly in contact with algae, with little bacterium-to-bacterium contact along the length of the cell. The algae are in contact with both the bacterial cells and other algal cells. Packing of the cells in the aggregates is tight, with apparent cell-to-cell contact, which suggests that the mechanism of aggregation involves interactions at the cell surface.

Determination of the Optimal Bacterium-Alga Ratio.

Microscopy showed that the bacterial filaments within an aggregate are intertwined throughout the structure and interact with multiple algal cells. This raised the question of how many bacteria are needed per algal cell to efficiently form these aggregates. The optimal bacterium-to-alga ratio is also important for practical use of this strain in harvesting algae, to maximize aggregation efficiency with a minimum of bacteria. To test multiple ratios of bacteria to algae and get statistically meaningful data, a 96-well plate aggregation assay was developed and is discussed in detail in the Materials and Methods section. Briefly, the bacteria and algae are combined in a 96-well plate and mixed to form aggregates. The entire volume of each well (aggregated and nonaggregated cells) is passed through a mesh with 50-μm openings. *Nannochloropsis* cells in culture are mostly found as single, spherical cells with a diameter of 2 to 3 μm. The few natural aggregates are small and have an average cross-sectional area of 71.6 μm$^2$ (16). The aggregates easily pass through the mesh, which has 2,500-μm$^2$ openings. The algal-bacterial aggregates are retained on this mesh, while nonaggregated cells pass through into a second 96-well plate. The algal cells that pass through into the second plate are then quantitated using chlorophyll fluorescence, and the quantity is compared to the quantity for a control where only algae (no bacteria were added to induce aggregation) were passed through the mesh. From these data, the percentage of algae that have been aggregated by the bacteria can be calculated. This process is referred to here as the filtration aggregation assay.

To determine the optimal bacterium-to alga ratio, the volume and concentration of algae were held constant in each well and different concentrations of bacteria were added. Ratios of between 25 bacteria to 1 algal cell and 1 bacterium to 125 algal cells were tested. The ratio of bacteria to algae for optimal aggregation was 1:1, with 1:5 bacteria to algae being only slightly less efficient than 1:1 bacteria to algae at aggregating *Nannochloropsis* (FIG. 4). These data are consistent with the visual results seen in fluorescence micrographs, where one bacterial cell interacts with several algal cells. At less than one bacterium per five algal cells, the efficiency of aggregation decreases. The efficiency of aggregation also decreases when the number of bacteria used becomes higher than the number of algae. This is likely due to increased self-aggregation between bacterial cells, leaving fewer bacteria to aggregate algal cells. Self-aggregation does occur when the bacteria are present in pure culture if the pH of the culture is increased to >10, which is similar to the pH in dense *Nannochloropsis* cultures. The data presented above indicate that there is an optimal ratio of bacteria to algae cell for bioaggregation and at higher or lower ratios, the efficiency of aggregation decreases.

Characterization of the Physical Conditions that Affect Algal Aggregation.

Next we were interested in determining which physical factors affect aggregation of the algae. From the microscopy data, it appears the mechanism of aggregation likely involves cell-to-cell contact, as opposed to aggregation of the algae by unassociated cellular exudates. To begin unraveling the nature of this cell-to-cell adhesion, we decided to test if aggregation is pH dependent. Solution pH dictates the surface charge of exposed proteins and will affect both specific and nonspecific protein-driven interactions. From a practical standpoint, the effect of pH on aggregation is also important because dense algal cultures can quickly increase pH through carbon fixation and also rapidly decrease pH through respiration. The effect of pH on aggregation was tested by adjusting the pH of the aliquots of algal cultures with either NaOH or HCl. The pH values tested ranged from 6 to 10. In this experiment, the pH of the algae was set, and then the filtration aggregation assay was run and a final pH reading was taken to ensure that the pH did not change significantly during the experiment. The pH value did have a significant effect on aggregation, as shown in FIG. 5. At pH 8 and below there was no significant aggregation, and at pH 9 and above aggregation was the highest. These data show that the aggregation of *Nannochloropsis oceanica* IMET1 by *Bacillus* sp. RP1137 is pH dependent, with aggregation occurring only when the pH is above 9. When the pH of the solution was decreased, disaggregation was observed, showing that aggregation was also reversible (data not shown).

In addition to pH, the salinity and temperature of algal production ponds can vary. The effect of salinity on aggregation was determined by adjusting the salinity of aliquots of *Nannochloropsis* cultures from 0 to 156 ppt. Optimal aggregation occurred at 20 ppt salinity, with minor but significant decreases in aggregation occurring at between 20 ppt and 156 ppt (see FIG. 6). Aggregation was also significantly decreased at 0-ppt salinity compared to 20-ppt salinity. The aggregates at 0 ppt were also noticeably smaller (data not shown).

Outdoor algal production ponds can experience changes in temperature, which could result in different potential harvesting conditions. We tested the effect of temperature by performing the aggregation process at between 10 and 40° C. Large differences that would be significant in practical applications at different temperatures were not observed; however, minor statistically significant changes were observed (see FIG. 7). Optimal aggregation occurred at 20° C.

One concern in using bacterial bioaggregation as a means of harvesting microalgae is that the production of the bacteria must be scaled with the production of the microalgae. One way to dramatically reduce the number of bacteria needed is to recycle the bacterial cells, effectively using the bacteria as aggregating microparticles. This would be made easier if dead cells retained their aggregation phenotype. To test if dead cells still aggregated algae, Bacillus sp. RP1137 cells were killed with 4% paraformaldehyde and the aggregation potential of these dead cells was compared to that of the same number of live cells. The efficiency of aggregation by the PFA-killed cells had a minor but significant increase relative to that by live cells (FIG. 8A). These data show that the aggregation phenotype of RP1137 is not due to a response by the cell and is instead a passive characteristic that is likely part of the cell surface. As a further step, aggregation of live and PFA-killed Nannochloropsis algae was attempted with both live and dead Bacillus sp. RP1137 cells. The aggregation efficiency with PFA-killed algal cells had a minor but significant increase relative to that with live algal cells (P=0.009). As with the live algae, the dead bacteria had a minor but significant increase in aggregation efficiency relative to that of the live RP1137 cells (FIG. 8B).

Aggregation of Candidate Biofuel-Producing Algae.

Bacillus sp. RP1137 effectively aggregates Nannochloropsis oceanica IMET1 in a pH-dependent and reversible manner. The Bacillus sp. RP1137 cells can also be used effectively after the cells have been killed by fixation. Next, we were interested in seeing if this bacterium can aggregate algae other than Nannochloropsis. A panel of algal strains that are of interest for their potential as biofuel production strains was tested. The strains tested were T. chuii, T. sucia, a Phaeodactylum sp., N. oleoabundans MK8520, C. cryptica MK89172, and N. angularis MK8708. The bacterium Bacillus sp. RP1137 was able to aggregate both of the Tetraselmis species, with a measured aggregation efficiency of 78.3%±4.3% for T. sucia and an efficiency of 13.1%±3.1% for T. chuii. The bacterium was also able to aggregate the Phaeodactylum sp. with a 17.3%±3% efficiency. N. oleoabundans, C. cryptica, and N. angularis had little or no aggregation, with efficiencies of 6%±4.4%, 1.3%±9%, and 0.02%±5.7%, respectively. However, these three nonaggregating algae could be aggregated in a bacterium-dependent manner if concentrated base was added to the solution. The concentrated base increased the pH to ca. 11, which is above the pH that the algae can achieve naturally (data not shown).

Characterization of Mechanism of Aggregation.

Next, we were interested in exploring the mechanism of algal aggregation by the bacterium RP1137. Nannochloropsis oceanica IMET1 was used as the model alga for these investigations. From the confocal microscopy images, we hypothesized that RP1137's filamentous morphology was important for aggregation of algae. To test this, we sheared the filaments by passing the cells through a 28.5-gauge needle repeatedly. Shearing reduced the RP1137 population to single cells and doublets (FIG. 9A). Sheared and unsheared cells were used for aggregation assays. The results showed that the morphology of the cells did have a significant effect on aggregation (P=2.71E−7), with sheared cells having a 2.6% decrease in aggregation efficiency compared to that of the unsheared cells (FIG. 9B). While the difference is statistically significant, this minor difference between filaments and single cells or doublets indicates that the filamentous form of RP1137 is not a major factor in the process of aggregation.

Fixed RP1137 cells are still able to aggregate algae, suggesting that the cell surface rather than active metabolic processes are important. To determine if the aggregation potential of the cells is dependent on exposed surface proteins, we digested RP1137 cells with proteinase K. This approach has been used with Helicobacter pylori to digest off and identify surface proteins (21). When cells were incubated at room temperature with proteinase K, there was no significant difference in aggregation efficiency between digested and nondigested RP1137 cells (see FIG. 10 in the supplemental material). Cells incubated with proteinase K at 50° C. displayed a significant (P=0.002) yet small decrease in aggregation efficiency of 4% compared to that for the nondigested controls, indicating that proteinase K-cleavable surface proteins are not a major factor in the aggregation process.

Adhesion between different cells is often mediated by lectin-carbohydrate-type interactions. These interactions can be disrupted by blocking the lectin with the addition of other carbohydrates. To determine whether lectin-carbohydrate interactions are important in aggregation, glucose, galactose, lactose, and mannose were added to the aggregation reaction mixtures at concentrations ranging from 200 mM to 800 mM. No significant inhibition of aggregation was observed during any of these experiments (data not shown).

We next hypothesized that divalent cations are required for aggregation. As an initial test of this hypothesis, we added 50 mM EDTA and 50 mM ethylene glycol tetraacetic acid (EGTA) to Nannochloropsis in f/2 medium while maintaining the pH at 10.3. Both EDTA and EGTA chelate divalent cations, with EDTA having a higher affinity for magnesium and EGTA having a higher affinity for calcium. EDTA and EGTA at 50 mM were sufficient to inhibit aggregation by RP1137 cells (FIG. 11A). To confirm the importance of divalent cations, we next performed dose-dependent aggregation assays in deionized water with different concentrations of magnesium or calcium ions. The cells were washed several times with deionized water (pH 10.3) to remove trace ions. Fixed algae and fixed bacterial cells were used. Aggregation was found to be highly dependent on the concentration of magnesium and calcium present in solution with the algae (FIG. 11B). At micromolar concentrations of either ion, little or no aggregation was observed. At 8 mM calcium, maximum aggregation efficiency was observed, while maximum aggregation efficiency with magnesium occurred at 16 mM. Addition of calcium or magnesium to Nannochloropsis alone did not precipitate aggregation in the absence of RP1137 cells. These data show that aggregation of Nannochloropsis by RP1137 is highly dependent on the magnesium and calcium concentrations.

Discussion

We show that live and dead Bacillus sp. RP1137 cells can rapidly aggregate Nannochloropsis oceanica IMET1 in a pH-dependent manner. Aggregation of Nannochloropsis oceanica IMET1 by Bacillus sp. RP1137 occurred extremely rapidly (in seconds). We also showed that Bacillus sp. RP1137 can aggregate other biofuel-producing algae. The study identified and evaluated the aggregation ability of this bacterial isolate and tested the robustness of its aggregation phenotype under different conditions. Due to the practical implications of the work, experiments were generally carried out in algal growth medium so that the results could be directly interpreted. It is also worth noting that a simple assay was developed to quantify aggregation potential, to avoid some pitfalls that befall other methods when trying to measure algae aggregated upon addition of bacteria. For example, using the dry weight of the aggregated algae is complicated by the unknown biomass that is contributed by the bacteria to the aggregates. The other common method to quantitate aggregation is to measure sedimentation rates, usually via determination of the absorbance of the supernatant (15). The bacteria added during aggregation assays contribute to the absorbance, occluding the removal of algae from the water column. To deal with these complications, the filtration aggregation assay measures chlorophyll autofluorescence to exclude any signal from the bacteria. Additionally, our method measures the uniform, nonaggregated algal fraction to get an accurate signal of the amount of algae remaining after aggregation. By comparing the remaining fluorescence after aggregation to the fluorescence of the same algal stock that received no treatment, the percentage of algae aggregated can be calculated.

One of the most important questions for the practicality of using bacteria as a means to harvest algae is how many bacteria are needed to harvest a given number of algae. Here the data show that a ratio of one bacterium to five algal cells is sufficient to efficiently harvest the algae. At ratios below this ratio, the efficiency of aggregation decreased; this decrease was likely due to individual bacterial cells being coated by algae and preventing the formation of larger flocs. When the number of bacteria increased above one to one, the efficiency of aggregation also decreased. This may be due to increased bacterium-to-bacterium interactions, which again occlude the formation of larger aggregates. These hypotheses will require further investigation. The bacteria can grow to densities 10 times higher than those of the algae, meaning that if the bacteria are used once, then 1 unit volume of bacteria is needed to aggregate 50 volumes of algae. This represents a substantial amount of bacteria to be cultured for a large-scale algal production facility. As a means to decrease the amount of bacteria needed and gain information about the mechanism of aggregation, we tested if bacteria that had been killed with paraformaldehyde could still effectively aggregate the algae. These killed cells exhibited an aggregation potential equivalent to that of their live counterparts. Mechanistically, this rules out any response by the cell to initiate aggregation and suggests that the mechanism of aggregation is associated with factors located at the cell surface. When cells were fixed by paraformaldehyde, their structure was preserved, which opens the possibility of incorporating the fixed cells onto a solid surface that would allow them to be reused after the algae have been removed from the water. This type of reuse of the bacterial cells could be facilitated by the finding that the aggregation process can be reversed by lowering the pH. An additional advantage of using killed cells is that there is no concern of contamination of the main algal culture or the environment, because the cells will not propagate.

The physical conditions under which harvesting of algae by *Bacillus* sp. RP1137 is most effective were investigated. Of the conditions tested, pH was the most critical, with aggregation occurring when the pH was at or above 9. In general, a lower percentage of algae was aggregated in experiments testing the effects of pH on aggregation than in other experiments. This may be because these earlier pH experiments were done with RP1137 cells at a different phase of growth than cells in later experiments. Preliminary data suggest that the aggregation potential of RP1137 changes over the growth period of the culture (results not shown). Obtaining pH values in this range does not require addition of base to the medium because algal cultures naturally increase the pH via the consumption of $CO_2$ during photosynthesis. Maximum values of pH of 10.2 to 10.4 were routinely observed in the *Nannochloropsis* cultures used in this study, with the pH varying from 7.5 in newly inoculated cultures to nearly 10.3 to 10.4 in dense cultures. In naturally occurring systems and algal production ponds, the pH varies throughout the day (22). Water temperature also varies during a day and throughout the year. We tested the effect of temperature and found only minor differences among the temperatures tested. There was also no large effect of salinity on aggregation, except at 0-ppt salinity, where aggregation was 15% lower than that for the samples tested with salinity at 20 ppt. It should be noted that in the pH, temperature, and salinity experiments, data were collected on aliquots of algae that were first grown under standard conditions and for which, after harvesting of a sample, the condition being tested was then varied so that the direct effect of these conditions on the aggregation ability of these cells could be measured. These measurements are likely dependent on how the particular condition tested impacts the surface chemistry of the cells. However, cells grown for extended periods of time under differing conditions of salinity, temperature, or pH may have different surface characteristics than the cells tested in these experiments.

The aggregation of several different algae by RP1137 was tested to determine if this bacterium could be used for harvesting other algae besides *Nannochloropsis*. The results showed that this bacterium can aggregate two strains of *Tetraselmis* and a *Phaeodactylum* species. The results also showed that this bacterium can aggregate *N. oleoabundans*, *C. cryptica*, and *N. angularis* effectively after first increasing the pH by the addition of base. These data show that *Bacillus* sp. RP1137 has the potential to aggregate other algae and may be useful for the harvesting of other algae besides the potential biofuel producer *N. oceanica* IMET1, although optimization would be needed to achieve the efficiencies that we achieved with *Nannochloropsis* aggregation.

The mechanism by which RP1137 interacts with and aggregates algae was investigated. RP1137 forms long filaments which were hypothesized to aid aggregation by increasing bridging between separate algal cells. We tested this hypothesis by shearing the filaments to break them into single cells or doublets and then using the sheared cells in aggregation assays. We found a significant, though minor, decrease in the percentage of algae aggregated in the sheared population. This suggests that the filaments are not the major phenotype responsible for aggregation. The minor effect of filament length and the fact that killed cells retain the ability to aggregate microalgae suggest that the cell surface characteristics may be important in aggregation. There are different types of potential cell surface interactions that could lead to aggregation, including specific and nonspecific protein interactions. To look for an effect due to surface proteins, we digested RP1137 cells with proteinase K to digest exposed and cleavable proteins. Digestion at room temperature yielded no significant difference in the aggregation potential of digested cells relative to that of a non-digested control. A significant, though minor, decrease in the percentage of algae aggregated was observed when the cells were digested at 50° C., at which proteinase K has higher activity. The lack of a large effect upon digestion with proteinase K does not exclude the possibility that surface-localized proteins play a role in aggregation. The strong effect on aggregation of higher pH values, when the bacterial cell surface would likely become increasingly negatively charged, suggested that the aggregation mechanism may be charge related. The finding that aggregation was completely abolished by washing the algae and bacteria several times in deionized water indicated that ionic species may be important for aggregation. Addition of EDTA and EGTA completely abolished aggregation in f/2 medium, suggesting that divalent cations are important for aggregation. The calculated concentrations of the major divalent cations in the f/2 medium used were 5.9 mM and 30.5 mM for the calcium and magnesium ions, respectively. To confirm the dependence of aggregation on these divalent cations, experiments in which magnesium or calcium concentrations were varied were performed. In these experiments, a strong dose-dependent increase in aggregation was observed with the addition of calcium or magnesium. Our preliminary investigation of the mechanism of aggregation therefore points to a charge-based mechanism that is dependent on divalent cations. In Gram-positive organisms like RP1137, it is known that negatively charged teichoic acids and peptidoglycan can bind magnesium and calcium ions (21). Therefore, we hypothesize that these divalent cations bind to these components in the cell wall of RP1137 and reduce the negative surface charge. Calcium ions may also neutralize the surface charge on *Nannochloropsis* cells, allowing both cell types to overcome electrostatic repulsion and form aggregates. Little is known about the cell wall of *Nannochloropsis*, though it is likely decorated with polysaccharides. Aggregation via charge neutralization with divalent cations has been hypothesized in other studies in which bacteria were found to be involved in aggregation (20) and in which algal autoflocculation in response to calcium was studied (23). The underlying mechanism of aggregation by RP1137 is likely similar to that of another *bacillus, Paenibacillus kribbensis*, the aggregation potential of which was also correlated with higher pH and the presence of calcium (15, 17).

Choosing the best method of harvesting algae will differ on the basis of the species used and the culturing system; however, some common measures can be used to compare different methods of harvest. In particular, efficiency of harvest, harvest rate, and energy input are important parameters. Efficiency of harvest refers to the percentage of algae that are removed from the water. In this study, the bacterium *Bacillus* sp. RP1137 has a typical harvest efficiency with *Nannochloropsis*, where 70 to 95% of the chlorophyll is removed from the water. Preliminary work suggests that the difference in efficiency is due to changes in bacterial growth stage and warrants further investigation. These values are similar to the harvest efficiency of 83% reported for the aggregation of *Chlorella vulgaris* by the bacterium *Paenibacillus kribbensis* (15, 17); however, *Bacillus* sp. RP1137 is capable of aggregating multiple algae. Other flocculating agents, such as aluminum sulfate and polyacrylamide, resulted in harvest efficiencies of 72% and 78%, respectively (15). Harvest can also be done using the following other physical means with the indicated harvest efficiencies: tangential flow filtration (70 to 89%), dissolved air flotation (80 to 90%), electrocoagulation (95%), and centrifugation, which has a greater than 95% harvest efficiency (7). It should be pointed out that these methods were tested with different algal strains, but they do provide a baseline of what can typically be achieved by the different harvest methods available. The *Bacillus* sp. RP1137-based harvest efficiency compares favorably with the harvest efficiencies of these known methods of algal harvest. Another important measure of a harvesting system is the rate at which the algae can be removed from the water, sometimes known as harvest productivity. The rate of aggregation by *Bacillus* sp. RP1137 is fast, with large aggregates forming in seconds, which is similar to the times for other flocculation-type harvest methods. In comparison, centrifuges, while having excellent harvesting efficiencies, have low harvesting rates.

Aggregation is typically a low-energy method to remove algae from water (7). It could be estimated that the energy associated with harvesting using *Bacillus* sp. RP1137 would involve the energy needed to grow the bacterium and the energy needed to apply the bacteria to the algal culture. Other systems of harvest are often energy intensive, with centrifugation requiring 8 kWh/m$^3$ of water, which contributes to the operating cost (7). Energy efficiency must be considered because the final product of algal biofuels is energy. Any system that costs more energy than is recovered from the algae is not sustainable.

Creating the next generation of liquid fuel infrastructure on the basis of the sustainable conversion of algal biomass to fuels will require the development of new technologies to reduce the barriers to large-scale production. One of the largest barriers to economically viable scale-up remains the harvesting step. Here we presented a new bacterial isolate that rapidly aggregates algae in a reversible manner. After fixation, the aggregation phenotype remains, a situation which effectively renders the cells specialized aggregating microparticles that may permit reuse of the cells with further research. Our results indicate that *Bacillus* sp. RP1137 may be useful in reducing one of the barriers to large-scale algal biofuel production.

Example 3

Algal derived biofuels are one of the best alternatives for economically replacing liquid fossil fuels with a fungible renewable energy source. Production of fuel from algae is technically feasible but not yet economically viable. Harvest of dilute algal biomass from the surrounding water remains one of the largest barriers to economic production of algal biofuel. We identified *Bacillus* sp. strain RP1137 and showed this strain can rapidly aggregate several biofuel producing algae in a pH and divalent cation dependent manner. In this study, we further characterize the mechanism of algal aggregation by RP1137. We show aggregation of both algae and bacteria is optimal in the exponential phase of growth and that the density of ionizable residues on the RP1137 cell surface changes with growth stage. Aggregation is likely via charge neutralization through binding of calcium ions to the cell surface of both algae and bacteria. We show charge neutralization occurs at least in part through binding of calcium to negatively charged teichoic acid residues. The addition of calcium also renders both algae and bacteria more able to bind to hydrophobic beads, suggesting aggregation may be occurring through hydrophobic type interactions. Knowledge of the aggregation mechanism may enable engineering of RP1137 to obtain more efficient algal harvesting.

Algal Aggregation by Bacteria

Energy underlies economies and is the largest single market in the world. However, most energy systems are based on finite nonrenewable resources that increasingly have higher direct and indirect costs. A growing research effort focuses on developing and deploying renewable energy sources to supplement fossil fuels. Research into renewable liquid fuels is of particular interest in the US because transportation is almost exclusively powered by petroleum.

Algal biofuels represent one of the best alternatives to sustainably produce fungible liquid fuels. Algae act as self-replicating bioreactors that use light energy to chemically reduce $CO_2$ into useful energy storage molecules. Unlike traditional crops, algae can be grown on land not suitable for agriculture and can be grown in wastewater or saltwater (24, 25). Algae have rapid growth rates, sometimes doubling their biomass in several hours, and can be harvested multiple times per year (26). Algal biomass is ideally suited for conversion to crude oil via hydrothermal liquefaction, which produces an oil that can be refined in existing refineries and also allows the recovery of limiting nutrients such as nitrogen and phosphorous (27).

While technologically feasible, studies have shown algal biofuels are not yet economically viable (28). Furthermore, to our knowledge no company has yet successfully produced algal biofuel at a profit. Only when profitability is achieved will algal biofuels become a self-sustaining venture that can make a significant impact on the production of renewable fuels. Harvest of the algal biomass has been identified as one of the key hurdles to economically producing fuel from algae (28). Algal biomass must be concentrated and most of the water removed before the biomass can be converted to fuel. Mature technologies for algal harvest include filtration, centrifugation, sedimentation, electrocoagulation, dissolved air floatation, chemical flocculation and bio-aggregation (29). Bio-aggregation uses biological agents such as extracellular polymeric substances, chitosan or whole 63 cells to form easily harvestable aggregates (30-34).

We described the algae aggregating bacterium *Bacillus* sp. RP1137 (40). This bacterium can rapidly aggregate multiple algae that are candidates for biofuel production. Aggregation is pH and divalent cation dependent (40). Fixed cells were also shown to be as effective as live cells at aggregating algae.

In this study we define the mechanism of algal aggregation by *Bacillus* sp. RP1137. We determine that aggregation is growth stage dependent and that calcium is involved in charge neutralization at the cell surface. Calcium binding to negatively charged teichoic acids is responsible, at least in part, for charge neutralization at the RP1137 cell surface. Finally, charge neutralization dispels electrostatic repulsion and likely allows the bacterial and algal cells to bind via hydrophobic type interactions.

Methods

Strains and Culture Conditions.

Liquid cultures of *Bacillus* sp. strain RP1137 were grown in marine broth 2216 (BD, Franklin Lakes, N.J.) at 30° C. in 125 ml Erlenmeyer flasks with shaking at 180 rpm. Marine broth 2216 plus 15 g/l Difco technical agar (BD) was used for solid medium. *Nannochloropsis oceanica* IMET1 was grown as described before (40). Briefly, *N. oceanica* was grown in 20 ppt salinity f/2 medium (41) in 500 ml ported photo-bioreactors at 25° C. with a light/dark photoperiod of 14/10.

Filtration Aggregation Assay.

A filtration aggregation assay was used to quantitate the amount of algae that were aggregated under a given condition. This assay has been described in detail (40). Briefly, the assay involves carrying out aggregation reactions with *N. oceanica* IMET1 and *Bacillus* sp. strain RP1137 in a 96 well plate. The entire volume of the reaction is then passed through a 50 μm mesh, aggregates that are larger than the mesh are retained and smaller particles pass through. Chlorophyll fluorescence is measured in the flow-through and compared to control samples without bacteria added to determine the percent of algae that are aggregated upon addition of the bacteria. Unless noted otherwise, aggregation assays were carried out in deionized water where pH was adjusted to 10.5 with NaOH and 10 mM $CaCl_2$ has been added.

Bacterial Aggregation Efficiency Time Course.

RP1137 cells were streaked from cryo-stocks and a single colony was used to start a 10 ml culture in marine broth medium. The culture was incubated at 30° C. in a 125 ml flask with 180 rpm shaking. From the initial culture three subcultures were started at a calculated optical density (OD) of 0.01 in 200 ml of marine broth.

Cultures were grown in 1 L flasks at 30° C. with 180 rpm shaking. Time points were taken every one to two hours for 24 hours. At each time point cells were collected, concentrated by Algal aggregation by bacteria centrifugation at 5580×g for 5 minutes, supernatant was aspirated, the cell pellet was suspended in 4% PFA in 1×PBS pH 7.4 and incubated for one hour at room temperature. Cells were then concentrated by centrifugation, the supernatant was aspirated and cells were suspended in 1×PBS to wash the cells. The cells were then again concentrated by centrifugation and suspended in a fresh aliquot of 1×PBS. Filtration aggregation assays were carried out using bacteria from each time point. The samples were normalized by cell surface area per milliliter (described below) so each sample had the same surface area available for interacting with algal cells.

Algal Aggregation Efficiency Time Course.

*N. oceanica* IMET1 cultures were grown as described above. Samples of algae were taken at two, five and 17 days after being subcultured, which represents early exponential, exponential and stationary phases of growth respectively. Cells were fixed following the protocol used for the bacterial cells. Samples were normalized by cell surface area per ml (described below) so each sample had the same available surface area for interacting with bacterial cells.

Determining Cell Size and Surface Area.

Cells from the time course were stained in 1×SYBR green I nucleic acid stain for 10 minutes in the dark. Cells were then visualized on a Zeiss Axioplan microscope with excitation from a Zeiss X-Cite 120Q Iris FL light source using a filter cube with a 470/40 BP excitation filter, a FT 495 dichroic mirror and a 525/50 BP emission filter. Cells were diluted or concentrated as needed to obtain well separated cells. The volume of each field of view was determined using the known depth of the bacterial hemacytometer and the height and width of the field of view. For each time point 20-30 fields of view were captured and saved as TIFF files. Image processing was done in Cell Profiler (42) with the following series of commands in a custom pipeline: LoadImage, ColorToGrey, IdentifyPrimaryObjects, ReassignObjectNumbers, MeasureObjectSizeShape and ExportToSpreadsheet. LoadImage imports the images. ColorToGrey converts the image to greyscale to reduce processor time. IdentifyPrimaryObjects was used to find and identify objects using the Otsu global algorithm, a 4-40 pixel cutoff and a 0.02-1 threshold cutoff. ReassignObjectNumbers was used to join cells within a filament into one object using a six pixel cutoff. MeasureObjectSizeShape was used to measure the perimeter and area of the identified objects. ExportToSpreadsheet was used to export the data as a .cvs file for import into Microsoft Excel for further analysis. Data were converted from pixels to micrometers using data gathered from a stage micrometer. Cell length was approximated by dividing cell perimeter by two; this provides a good estimate of cell length for filamentous bacilli though it does introduce a slight overestimate of the absolute size of the cells. To obtain cell surface area for normalization both perimeter and area data are used. The key parameter needed, but unavailable directly in Cell Profiler, for calculating surface area of a cell is the radius of the cell. To derive the radius of individual cells the 2D images of cells were used and the bacilli were modeled as a rectangle with half circles on each end. The resulting equation for area is then sum of the area of a circle and the area of a rectangle or $A=\pi r^2+2r((P/2)-2r)$ where A is the area of the cell, r is the radius of the cell and P is the perimeter of the cell. Since A and P are measured values the equation can be solved for r using the quadratic equation which yields two solutions, one of which is the real radius of the cell. Derived radius values were checked against the manually measured average radius along the length of individual cells. Calculated values are very close to measured values indicating the method can be used to accurately calculate cell radius in an automated format. Cell radius was used to calculate surface area of a three dimensional cell by modeling the cell as two halves of a sphere plus the surface area of a cylinder minus the ends. Surface area of individual cells was calculated for 900-1600 cells per time point. Cell numbers per ml were then used to calculate available surface area per unit volume. Surface area per ml of individual sample were used to normalize available surface area for interaction with algal cells between samples at different time points. The available surface area of *N. oceanica* IMET1 time points was determined using a similar pipeline to that used for RP1137 cells with the following modifications. Images were captured using chlorophyll auto fluorescence. *Nannochloropsis* cells are spherical so the measured area of the 2D images could be used to directly derive radius using the equation for the area of a circle ($A=\pi r^2$). Radius could then be used to calculate 3D surface area of a sphere ($A=4\pi r^2$). Surface area per unit volume was determined by combining surface area data with cell concentration data.

LiCl Treatment of RP1137 Cells.

Lithium chloride treatment was done according the protocol of Lortal et al. (43). RP1137 cells were concentrated by centrifugation at 20,000 g for 3 min and the cell pellet was suspended in either distilled water or 5 M LiCl. Cells were incubated for 15 minutes at room temperature and then concentrated by centrifugation. The cell pellets were suspended in pH 10.5 deionized water with 10 mM $CaCl_2$ for aggregation assays.

Base Titration of Whole Bacterial Cells.

Live RP1137 cells were used for base titration experiments. Cells were taken in exponential phase (OD=0.7) and stationary phase (OD=1.6). Culture volumes were normalized by surface area to ensure the same amount of bacterial cell surface was being titrated in each sample. Cells were concentrated by centrifugation at 15,000 g for 5 minutes and the cell pellet was suspended in pH 5 deionized water. This washing step was repeated twice more to ensure salts had been removed and the cells were equilibrated to pH 5. Base in the form of 0.25 M NaOH was added to the cell suspension and pH was recorded after each addition when the value stabilized.

Calcium Binding Assay.

Calcium binding was evaluated by measuring the concentration of calcium remaining after 1 ml of cells had been added. Calcium binding assays were performed with fixed RP1137 cells from the exponential phase (OD=0.7) of growth. Known concentrations of $CaCl_2$ were added to cells in pH 10 deionized water. Cells were then removed by centrifugation at 20,000 g for 3 minutes. The calcium concentration in the supernatant was measured using the LaMotte Calcium Hardness colormetric kit (Chestertown, Md.). The kit was adapted for use in a 96 well format and measurement in a Spectro Max M5 plate reader. The readout for the assay was absorbance at 635 nm. Absorbance at this wavelength is linear for calcium concentrations between 0-160 µM. Samples were diluted to ensure they were within the linear range of the assay. Absorbance values were compared to a $CaCl_2$ standard curve to determine the concentration of calcium remaining.

Calcium Coordination Experiment.

RP1137 and *Nannochloropsis* cells were separately suspended in pH 10.5 water with 10 mM $CaCl_2$. To ensure the cells were pre-loaded with calcium both bacteria and algae were concentrated by centrifugation at 20,000 g and the cell pellets were suspended in the same solution. This pre-loading step was repeated once more. The cells were then used in filtration aggregation assays compared to controls where only the algal cells were pre-loaded with calcium.

C18 Binding Assay.

Binding of cells to C18 resin was performed with fixed RP1137 cells from the exponential phase of growth (OD=0.7) and with fixed *Nannochloropsis* cells from +5 days post inoculation. Dry C18 beads with a 10 µm diameter were purchased from Hamilton (Reno, Nev.). Beads were reconstituted in methanol overnight. The beads were concentrated by centrifugation at 20,000 g for 1 minute and suspended in pH 10.5 deionized water with 10 mM $CaCl_2$. This process of concentration and suspension in pH 10.5 deionized water with 10 mM $CaCl_2$ was repeated twice more to ensure methanol was removed and the beads were equilibrated in the test solution. The equilibration process was repeated without $CaCl_2$ for a separate aliquot of beads to obtain beads for the "no calcium" samples. For each experiment 200 beads were used per cell as this was found to give maximal binding with the minimum number of beads. Equal numbers of algal or bacterial cells were incubated with C18 beads (200:1 bead to cell ratio) in the presence or absence of 10 mM $CaCl_2$. The mixtures were analyzed with an Accuri C6 flow cytometer to count the number of unbound algal or bacterial cells. The beads were distinguished from cells by their larger forward scatter area with an upper forward scatter area cutoff of 1,270,000. A lower cutoff of 44,000 was used to remove background particles found within the medium. RP1137 cells fell between these two cutoffs. Algal chlorophyll autofluorescence was used to distinguish *Nannochloropsis* cells from their associated bacterial cells using the FL3 channel (excitation 488 nm, emission 670 LP filter) on the flow cytometer. Only particles that were between the two forward scatter cutoffs and had a chlorophyll autofluorescence of greater than 10,000 were counted as algal cells. These settings counted the unbound bacterial or algal cells which allowed comparison of the number of bound cells in the presence or absence of calcium.

Zeta Potential.

Measurement of cell surface charge or zeta potential was done on a dynamic light scattering instrument (Malvern Instruments Ltd, Worcestershire, UK). Measurements were done on fixed algal cells from two, five and 17 days after being subcultured and on fixed RP1137 cells that were taken in exponential phase (OD=0.7) and stationary phase (OD=1.6). Cells were concentrated by centrifugation at 20,000 g for 1 min, supernatant was aspirated and the cells were suspended in pH 10.5 deionized water. To ensure removal of trace salts the cells were again concentrated by centrifugation, supernatant was aspirated and the cells were suspended in pH 10.5 deionized water. For each sample zeta potential was measured at 0, 0.156, 0.313, 0.625, 1.25, 2.5, 5, 10, 20 and 40 mM $CaCl_2$.

SDS Inhibition of Aggregation.

Inhibition of aggregation by sodium dodecyl sulfate (SDS) was tested using the filtration aggregation assay. Fixed algae from two days after subculture were used. Fixed RP1137 cells from exponential phase (OD=0.7) were used. Both algae and bacteria were concentrated by centrifugation at 20,000 g for 1 min, supernatant was aspirated and the cells were suspended in pH 10.5 deionized water with 10 mM $CaCl_2$. This washing step was repeated once. In the treatment samples SDS was added to algae to a final concentration of 1%. Filtration aggregation assays were carried out as described for quantitation of the percentage of algae aggregated in the SDS treated cells compared to the untreated controls.

Calcium Displacement of Pinacyanol.

To determine if calcium displaces pinacyanol bound to the bacterial cell surface, fixed RP1137 cells from exponential phase were concentrated by centrifugation at 20,000 g for 1 min, supernatant was aspirated and the cells were suspended in pH 10.5 deionized water. This washing step was repeated once. RP1137 cells were then stained with 20 µM pinacyanol chloride (Sigma). The stained cells were added to an equal volume of water or water with $CaCl_2$ resulting in a final pinacyanol concentration of 10 µM. The final concentration of $CaCl_2$ solutions tested were 0, 0.15, 0.6, 2.5 and 10 mM. The samples were mixed by vortexing and then centrifuged at 20,000 g for 3 minutes. The supernatant was aspirated to remove unbound dye and the cells were suspended in a fresh aliquot of water with the same calcium concentration. Absorbance of the dyed cell solutions were measured at 485 nm in an M5 Spectromax plate reader. Absorbance spectra from 450-650 nm were gathered at 5 nm increments for unstained RP1137 cells, stained cells, water+ pinacyanol and water+pinacyanol+10 mM $CaCl_2$.

Results and Discussion

Characterization of Cell Length Over a Growth Period.

In this study, we aimed to characterize the mechanism by which *Bacillus* sp. strain RP1137 aggregates algae. In previous, work we showed that divalent cations are important for aggregation and that fixed cells were just as effective at aggregating algae as live cells, pointing to the cell surface as the important cell structure for investigation of the aggregation mechanism (40). Our previous work also ruled out filament length as an important factor for aggregation but initial observations suggested aggregation ability changed over the growth cycle of a culture. Since the cell morphology changes over the growth period we cannot accurately normalize by optical density or cell counts. To accurately normalize between time points we first needed to characterize this change in morphology. Single cells and filaments of cells are present in RP1137 cultures. In this paper we define cell length as the total length of either a lone single cell or the length of a chain of cells in a filament. Changes in cell length are shown in FIG. 12 where we measured cell length over time through a combination of fluorescent microscopy and automated image analysis of thousands of cells. The results show cell length does change over a growth period.

Change in Aggregation Ability of RP1137 Over a Growth Period.

With the cell length data we were able to calculate cell surface area data which were used to normalize the cell surface area between different time points. Normalization of cell surface area allowed us to isolate changes in the cell surface composition from changes in the amount of cells or amount of cell surface area in a sample. Using normalization, we then asked whether aggregation potential changes over a 262 growth cycle. In FIG. 13, the percent algae aggregated is plotted with the growth curve of the bacterium. Aggregation was most effective in the exponential phase of growth where 80% of the algae are found in the aggregates. As the cells enter stationary phase the aggregation potential per normalized cell surface area decreases and reaches a minimum value of 40% aggregated algae at 20 hours. These data show the aggregation potential of the bacterial cell surface decreases when the cells enter stationary phase, indicating the surface chemistry of the cell was likely changing. From the perspective of applying RP1137 for algal harvest these results show it is important use bacteria from exponential phase to obtain the best aggregation ability.

Change in Aggregation Ability of *N. oceanica* IMET1 Over Time.

Next we measured the aggregation potential of *N. oceanica* IMET1 algal cultures at different growth stages. The same bacterial sample was used for the experiments and the algal cells were normalized between samples using the cell surface area. Unlike the bacteria, algal cell morphology does not change significantly over a growth cycle (data not shown). Algal aggregation was tested at two, five and 17 days after subculturing. Cells in the +2 days samples were just beginning to grow while the algae were fully into exponential phase by day five. At +17 days the algae were in stationary phase. Aggregation was most efficient with cells at the +5 day time point and was significantly more efficient than cells at +2 days and +17 days (FIG. 14). The data show the algae are most effectively aggregated during exponential phase and have decreased aggregation ability when they enter stationary phase. Little is known about the cell surface of *Nannochloropsis*, however these results suggests the surface chemistry of the cell is changing with the growth phase of the alga. Changes in surface chemistry will be investigated further in subsequent sections. The change in aggregation efficiency indicates that when harvesting algae in practice with RP1137 cells it best to harvest them while they are exponential phase.

LiCl Treatment and S-Layer Proteins.

Our previous work showed that proteinase K treatment of the cell surface did not significantly decrease aggregation, suggesting surface proteins were unlikely to be involved in aggregation (40). While proteinase K can cleave surface proteins (44), it may not cleave proteins that do not have an exposed cleavage site. S-layer proteins are often involved in adhesion of gram positive bacteria to either biotic or abiotic surfaces and can be involved in aggregation (45). S-layer proteins are also typically attached to peptidoglycan via electrostatic interactions and can be removed by LiCl treatment (43). To test if the S-layer is involved in aggregation RP1137 cells were treated with 5 M LiCl. The treated cells did not have a significant decrease in their aggregation ability (data not shown) suggesting the S-layer proteins are not involved in the aggregation phenotype.

Base Titration of the RP1137 Cell Surface.

The data we have collected show that specific or non-specific protein-protein interactions at the cell surface are inconsistent with available data. We next hypothesized that perhaps a more general property of the cell surface is involved in the aggregation phenotype of RP1137. Since the bacterial cells show a significant difference in aggregation ability between exponential and stationary phase we decided to test if the surface chemistry of the cells at these growth stages is different, specifically if the density of deprotonatable residues at the cell surface was different. To test this we used base titration of whole live cells. The results of base titration of RP1137 cells, in FIG. 15, show that cells in exponential phase have a lower number of deprotonatable residues compared to the cells in stationary phase because pH increases more quickly as base is added relative to stationary phase cells. Since these experiments were normalized by cell surface area this translates to more positive or neutral residues per unit area of cell surface. The data show there is a measurable difference in surface chemistry between these two populations of cells.

Binding of Calcium to the Cell Surface.

Cell surface chemistry can also be affected by the ions that are present. Previously, we showed that aggregation is dependent on divalent cations, and we hypothesized these ions reduce or neutralize negative charge at the cell surface (40). To determine if calcium ions bind to the surface of the bacterium we measured the amount of calcium removed by the cells at increasing calcium concentrations. Briefly, cells were incubated with known concentrations of calcium, cells were removed by centrifugation and the remaining calcium concentration in the supernatant was measured to determine the amount of calcium bound by the cells. FIG. 16 shows that calcium binds to the bacteria and that bound calcium increases with increasing calcium concentration up to a concentration of 0.625 mM. A saturating concentration of surface bound calcium ions could allow cells to aggregate in at least two ways. Charge neutralization eliminates electrostatic repulsion between cells and is commonly cited as a method in which cells can get close enough to adhere via other attractive forces such as hydrophobic or Van der Waals type interactions (46). Another method of interaction cited in the literature is coordination of ions bound to one cell by another cell (47). In this method of aggregation two cells interact via bridged ions. This is similar to the commonly used nickel-NTA affinity chromatography system which binds proteins via the common coordination of a nickel ion by the 6x-His tag on a protein and a nitrilotriacetic acid residue attached to a solid substrate. The ion coordination model of aggregation predicts that algal and bacterial cells that have been preloaded with calcium separately before combination should not interact efficiently because they are both already binding ions at their cell surface and thus are less likely to bind via common ions. However, the charge neutralization model predicts a different outcome. It predicts cells preloaded with calcium before combination should interact and lead to aggregation. We tested the hypothesis that aggregation occurs by coordination of common ions by preloading algal and bacterial cells with calcium separately before mixing them. The results showed that the cells still aggregated with an average value of 74.6±1.1% algae aggregated. These results point toward the charge neutralization model of aggregation rather than the coordination model.

Measurement of Zeta Potential.

To test the hypothesis that calcium ions are causing charge neutralization, we used dynamic light scattering to measure apparent cell surface charge or zeta potential at different calcium concentrations. Zeta potential was measured for both bacterial and algal cells at different stages of growth. The data shown in FIG. 17 demonstrate that surface charge in both bacteria and algae decreases with increasing calcium concentration. In the absence of salt the exponential phase bacterial cells have a more negative charge at $-110\pm6$ mV compared to the stationary phase cell with a zeta potential of $-72\pm6$ mV. As calcium concentration increases the zeta potential of both exponential and stationary phase bacterial cells becomes similar, with the charge curves overlapping at 10 mM calcium which is the optimal concentration for aggregation. At this concentration, charge is $-18.6\pm1.05$ mV for exponential cells and $-19.8\pm1.05$ mV for stationary phase cells, both of which are at or below $-20$ mV which is often considered as the threshold where charge is no longer strong enough to separate cells by electrostatic repulsion. The surface charge of algal cells also becomes less negative as calcium concentrations increase, but compared to the bacterial cells the algae require a higher calcium concentration to get below the $-20$ mV threshold. This result suggests the bacterial cells have a higher affinity for calcium ions than the algal cells or that the algae have a higher number of calcium binding sites. The calcium binding and zeta potential measurements show bacterial cells bind calcium which results in charge neutralization. Next we aimed to determine what forces were likely mediating the binding of the RP1137 and *Nannochloropsis* cells.

RP1137 Binding to C18 Resin.

From previous work we knew that surface proteins, filament length and lectin-carbohydrate type interactions were not involved in the underlying mechanism of aggregation (40). Aggregation of multiple and distinct algae species by RP1137 also pointed toward a general instead of specific mechanism of aggregation (40). Since the cell surface charge decreased upon addition of calcium, we hypothesized that bacterial and algal cells interact via hydrophobic type interactions and thus should be become more able to interact with a hydrophobic surface under these conditions. We tested this by measuring the number of individual cells that were not bound to hydrophobic C18 beads in the presence or absence of calcium. Unbound cells were measured because it is easier to get accurate data on free cells as compared to the number of cells bound to the beads. FIG. 18A shows that there are fewer unbound bacterial cells in the presence of calcium. This shows that the bacterial cells are more able to bind to a hydrophobic surface when calcium is added. The algal cells show a similar trend with fewer unbound cells present in the presence of calcium (FIG. 18B). These data demonstrate that the algal cells are also more able to interact with a hydrophobic surface in the presence of calcium. Together these data support the hypothesis that bacterial and algal cells interact at least in part through hydrophobic interactions. Hydrophobic interactions are often involved in aggregation (46), so this result fits with what others have found. If both bacterial and algal cells can interact with a defined hydrophobic surface then we propose they could interact with each other. This mechanism of interaction suggests that we should be able to inhibit the interaction by coating the cells with an anionic detergent prior to the aggregation process.

SDS Inhibition of Aggregation.

To test the hypothesis that an anionic detergent will disrupt an aggregation process that occurs via hydrophobic interactions we pre-coated the bacterial and algal cells with the anionic detergent sodium dodecylsulfate (SDS). SDS has a hydrophobic tail attached to an anionic sulfate group. If the bacterial and algal surface is more hydrophobic then the SDS should orient with the hydrophobic tail oriented toward the cell and the anionic sulfate residue facing the solvent (water). The cells in this setup now have an external negative charge which should inhibit aggregation. We observed that addition of SDS results in a significant decrease in aggregation ($p=5.19E-05$), these data are shown in FIG. 19. Visually, aggregation appears to be completely inhibited (FIG. 19A), however quantitation using the aggregation assay shows that small aggregates are still formed (FIG. 19B). The aggregation assay works by removing aggregates that do not pass through a mesh with 50 μm by 50 μm square holes. The results indicate the formation of large aggregates is inhibited but that smaller aggregates (>50 µm) are still being formed. These smaller aggregates incorporated less of the algae into the aggregates. These results indicate that the interaction between bacteria and algal cells were not completely disrupted under the conditions tested. It is possible other forms of bonding are important in the interaction between these cell types. Finally, the cells may have gained sufficient momentum when mixed with the vortexer to overcome the electrostatic repulsion and allow the some of the cells to get close enough to interact. The idea that the bacterial and algal cells bind each other via hydrophobic interactions implies the cells should also self-aggregate in the absence of the other cell type; this is observed for RP1137 cells at high pH in the presence of divalent cations.

Nannochloropsis cells do form small self-aggregates of 5-10 cells but they do not form large aggregates. The reason Nannochloropsis cells do not form large aggregates is unknown; however, in the C18 bead assays more of the bacterial population is bound to the beads than the algae population, suggesting there are less algal cells whose cell surface is hydrophobic enough to bind the beads within the population. We speculate that this smaller the population of hydrophobic cells has a lower chance of finding other hydrophobic cells in which they can interact with. This explanation must tempered with the knowledge that up to 95% of the algal population can be harvested with RP1137, which may imply the interaction between algae and bacteria is different than the interaction of algae with other algae. Further study is needed to clarify what other forces besides hydrophobicity may be at play.

Determining a Binding Site of Calcium at Cell Surface.

The calcium binding data indicated the ions are binding to the bacterial cells and result in charge neutralization. Teichoic acids are negatively charged and bind various cations including calcium (48), making them a plausible target for charge neutralization by calcium ions. Previous studies have shown that teichoic acids have a higher affinity for calcium relative to magnesium (48), matching data we have gathered in a previous study that showed the RP1137 has a higher affinity for calcium than magnesium (40).

We tested whether calcium binds the teichoic acid residues of RP1137 using the dye pinacyanol chloride. Pinacyanol chloride binds purified teichoic acids and upon binding undergoes an absorbance shift which results in a new absorbance band centered at 485 nm (49). Interestingly, calcium competes for binding of teichoic acid with the dye. When calcium is present the dye is removed from teichoic acid and the absorbance band at 485 nm is no longer present (49). Here we use this property to determine if calcium is binding teichoic acids on RP1137 cells. The absorbance spectra of the dye alone, dye with calcium, cells and cells with dye are shown in FIG. 20A. The cells with dye show the characteristic peak in absorbance at 485 nm as was observed in purified teichoic acid. The peak is not present in the cells alone, dye alone or dye with calcium. Next, the cells were stained with pinacyanol and then exposed to different concentrations of calcium. The cells are then washed to remove unbound dye and the absorbance of the cells at 485 nm is recorded. If calcium is binding teichoic acids then it should displace the dye and result in a decreased absorbance at 485 nm with increasing calcium concentration, which is what we observe in FIG. 20B.

CONCLUSION

Information about the mechanism of aggregation primarily is useful for predicting which algae RP1137 can harvest. The mechanistic data presented here suggests that RP1137 will be able to harvest algae where charge neutralization occurs in either sea water or fresh water with between 2-20 mM calcium ions at a pH of greater than or equal to 9. RP1137 will not likely aggregate algae that have significant negative charge (>−30 mV) under these conditions. The chemical characteristics of the RP1137 cell surface can be used to design means of attaching the cells to solid substrates such as hydrophobic or magnetic beads to aid in recovering the cells after aggregation. In a previous study, we show aggregation is pH dependent and reversible. If fixed RP1137 cells can be attached to beads and maintain their aggregation phenotype, then there is the possibility of reusing the cells multiple times. In this scheme the fixed cells would be attached to magnetic beads and then used to aggregate algae. The magnetic aggregates could be recovered and then pH would be lowered by either adding acid or by allowing the concentrated, and thus light limited, algae to lower pH via respiration. Lowering pH reverses the aggregation process and separates the algae from the bacterium-magnetic bead complex. The bacterium-bead complex can then be separated from the algae with a permanent magnet and reused for another round or harvest.

Example 4

Magnetite Synthesis

Magnetite microparticles were synthesized by the published procedure of Hu et al. 2013. Briefly the procedure involves dissolving ferric and ferrous chloride salts in water that has been purged of oxygen by bubbling with nitrogen gas. The reaction is carried out at 80° C. with constant mixing. Ammonium hydroxide is added resulting in the formation of the magnetite particles. The particles are washed with distilled water twice and are then ready for conjugation to the aggregating bacterium.

Magnetite/Bacterium Conjugation

The bacterium used has been designated Bacillus sp. strain RP1137 and was the subject of a prior invention disclosure (application #61607657). The bacterium is able to aggregate several algal species and has the advantage that the aggregation process can be reversed by decreasing the pH of the surrounding water. This can be achieved by the addition of acid or by simply letting the cells lower the pH automatically though respiration. The cells aggregate algae as well or better when fixed with paraformaldehyde, these dead cells are used for conjugation to the magnetite particles.

The magnetite particles are reported to have a positive surface charge, while the RP1137 cells have a highly negative surface charge. Conjugation of the cells is facile due to the cells and the particles having opposite surface charge. The conjugation is achieved by mixing the cells and the particles in water with a pH of 7 (FIG. 21). Note that conjugated cells can be purified from not conjugated cells using a magnetic field. Only those cells attached to magnetic particles will migrate to the source of the field. The conjugated particles are then ready to use.

Application

The primary application of the bacterium/magnetite particles is the large scale harvest of algae for biofuels. While algae are easy to harvest at the laboratory scale as the scale of production increases the difficulty of harvesting algae in an economically viable manner increases. The developed bacterium/magnetite particles represent a potential solution to this harvest problem. Another application is the harvest of algae for higher value algal commodities such as nutraceuticals, and pigments.

Example 5

Maghemite Particle Synthesis

To obtain maghemite particles, magnetite microparticles were first synthesized by the published procedure of Hu, Y.-R., et al., *Bioresource Technology* 138:387-390 (2013). Briefly, the procedure involves dissolving ferric and ferrous chloride salts in water that has been purged of oxygen by bubbling with nitrogen gas. The reaction is carried out at 80° C. with constant mixing. Ammonium hydroxide is added resulting in the formation of the black magnetite particles. The particles are then washed with distilled water twice. Magnetite is $Fe_3O_4$ and maghemite is $\gamma$-$Fe_2O_3$. To obtain the chemically distinct maghemite particles, the magnetite particles are then oxidized by exposure to atmospheric oxygen, a process described by Tang, J., et al., *J. Physical Chemistry B* 107:7501-7506 (2003). The oxidized particles are brown in color and are ready to be used for harvesting algae.

Harvesting of Different Species of Algae with Maghemite Particles

The maghemite particles are effective at harvesting a wide diversity of algae. The maghemite particles can be used to harvest several green algae including *Nannochloropsis*, *Tetraselmis* and *Scenedesmus*. The brown alga, *Isochrysis*, can also be harvested as well as several species of cyanobacteria found in fresh water, brackish water and the open ocean. The organisms, which have been successfully harvested span most of the known photosynthetic groups including both Eukaryotic and Eubacterial domains of life. These organisms live in diverse salinities that include fresh, brackish and salt water. The broad applicability of maghemite particles for harvesting diverse algae is best demonstrated in FIG. 22 where the particles are shown harvesting a mixed algae community found in natural pond water. As seen in FIG. 22, the majority of the algae are drawn to the magnets and can be removed from the solution when a magnet is placed near the tube. Microscopic examination of the magnets shows the particles bind various single and multicellular green algae, filamentous and single celled cyanobacteria and macroalgae such as *Lemnaceae* (duckweed). The ubiquity of the binding mechanism is likely due to the interaction of the positively charged surface of the maghemite with the negatively charged cell surface. Most living cells are negatively charged. These maghemite particles can be used to bind to algae and then be removed from solution in bound form using a magnet. This method can be used to harvest and dewater a wide variety of algae species.

Harvesting Algae from Pond Water

A sample of pond water was obtained that contained an unknown mixed culture of algae. The pond water contained single celled and filamentous cyanobacteria, single celled green algae and macro-algae (*Lemna* sp.). The pH of the water was 7, and no modifications were made to the water chemistry. Algae were harvested by the addition of maghemite nanoparticles, mixing and then exposing the sample to a magnetic field.

Results:

Both micro- and macro-algae were removed from solution and found to be attached to the maghemite beads by microscopic examination. The visual result of this process is shown in FIG. 22.

Harvesting of Individual Algal Species

Harvesting of eight different species of algae with the maghemite particles was tested. The algae were tested in their growth media with no modifications. The following algae were tested with the growth medium used listed in parentheses: *Isochrysis galbana* (F/2), *Tetraselmis chui* (F/2), *Tetraselmis suecica* (F/2), *Nannochloropsis oceanica* IMET1 (F/2), *Scenedesmus* sp. HTBI (BG11), *Synechococcus* WH7805 (SN30), *Synechococcus* CB0101 (SN15) and *Synechococcus* WH7803 (A+). For each species 500 µl of algae was harvested by the addition of 1 mg of maghemite. Samples were mixed and then exposed to a permanent magnetic field.

Results:

All algae were harvested to different degrees as determined by visual and microscopic examination of the algae/maghemite mixture. This result provides a qualitative test of aggregation confirming the efficacy of the particles at harvesting diverse algae.

Testing Harvesting Efficiency

Methods:

The efficiency of harvest of *Isochrysis galbana*, *Scenedesmus* sp. HTBI, *Synechococcus* CB0101, *Synechococcus* WH7803 and *Tetraselmis chui* was tested with different amounts of the maghemite particles. Per 200 µl sample of algae the following amounts of maghemite particles were tested: 0.065, 0.13, 0.26, 0.455, 0.65, 1.3 and 2.6 mg. Particles were added, mixed and then the solution was exposed to a magnetic field. The supernatant was aspirated and the amount of algae present was quantified using chlorophyll fluorescence (488 nm excitation, 515 nm cut off, 685 emission) using an M5 Spectromax plate reader. The fluorescence of the treated samples was compared to an untreated control to calculate the percentage of algae that had been removed from solution.

Results:

The results, shown in FIG. 23, demonstrate that *Tetraselmis chui*, *Synechococcus* WH7803 and *Scenedesmus* sp. HTBI are efficiently harvested by the maghemite particles. *Synechococcus* CB0101 and *Isochrysis galbana* are also harvested by the particles but have a lower percentage of the cells removed from solution.

Testing Particle Saturation

To determine if the particles are saturated the first time they are used, the same batch of particles was used to successively harvest different aliquots of a *Tetraselmis chui* cells. For this experiment 1.3 mg of particles were used with 200 µl of *Tetraselmis chui* cells. As before, the algae remaining in the non-bound supernatant were quantitated using chlorophyll fluorescence. The fluorescence values from the supernatants were compared to controls without added particles to determine the percentage of algae removed from solution.

Results:

The results, shown in FIG. 24, demonstrate the particles are not saturated after one round of harvesting. The particles do not become saturated until they have gone through four rounds of harvesting, with each successive round resulting in additional removal of algae from the supernatant, but with less algae harvested by each successive step.

Testing Removal of Algae from Maghemite Particles

To determine if the algae could be removed from the particles lowering or raising pH. In this experiment 50 µl of *Tetraselmis chui* cells bound to 0.325 mg of maghemite particles were used. To this either acid (0.2 M HCl) or base (0.25 M NaOH) were added. For both acid and base 1, 5, 10 and 20 µl were added. After each addition the mixture was mixed by vortexing, exposed to a magnetic field and observed.

Results:

Neither acid nor base was effective at releasing the algae from the particles, indicating the properties of the particles is different than those of the magnetite particles and that the binding is not reversible under the conditions tested.

The maghemite have been found to aggregate *Isochrysis galbana*, *Tetraselmis chui*, *Tetraselmis suecica*, *Nannochloropsis*, *Scenedesmus* sp. HTBI, *Synechococcus* WH7805, *Synechococcus* CB0101, *Synechococcus* WH7803, pond water algae, which include unknown filamentous, and single cell cyanobacteria, green algae with different morphotypes and macroalgae such as duckweed.

The particles have been used from pH 7 up to pH 10.5 and worked under all of these conditions. They have been used in undefined freshwater from a pond, in a freshwater algal growth medium named BG11 and in a salt water medium named f/2.

Particles with sizes from 10 nm up to 100 µm have been tested, a 10,000 fold size range. Particles at both ends of the spectrum are active, though the small particles seem to be better at harvesting diverse algae.

The particles were used to harvest twice their weight in algal biomass. For example 1 kg of particles can hold 2 kg of algae.

The algae cannot be removed from the particles by decreasing the pH or by increasing the pH. They also cannot be removed by adding calcium chloride or a combination of calcium chloride and base.

Applications

The primary application of the maghemite particles is the large scale harvest of algae for biofuels. While algae are easy to harvest at the laboratory scale, as the scale of production increases the difficulty of harvesting algae in an economically viable manner increases. The developed maghemite particles represent a potential solution to this harvest problem. Another potential application is the harvest of algae for higher value algal commodities such as nutraceuticals, and pigments. A final application may be for remediation of algal blooms in natural water ways. In many areas, such as Lake Erie, the Gulf of Mexico and the Chesapeake Bay, algal blooms occur seasonally with influxes of nutrients. When the bloom dies, its decay removes oxygen from the water resulting in dead zones. With this technology the biomass from the bloom could be harvested there by preventing the depletion of oxygen that results in dead zones. The collected biomass can then be converted into fuel.

REFERENCES

1. U.S. Energy Information Administration. 13 Jan. 2013, posting date. Your guide to understanding energy. U.S. Energy Information Administration, Washington, D.C.
2. U.S. Environmental Protection Agency. 13 Jan. 2013, posting date. Renewable fuel standard (RFS). U.S. Environmental Protection Agency, Washington, D.C.
3. Schenk P M, Thomas-Hall S R, Stephens E, Marx U C, Mussgnug J H, Posten C, Kruse O, Hankamer B. 2008. Second generation biofuels: high-efficiency microalgae for biodiesel production. Bioenerg. Res. 1:20-43.
4. Waltz E. 2009. Biotech's green gold? Nat. Biotechnol. 27:15-18.
5. Chisti Y. 2008. Biodiesel from microalgae beats bioethanol. Trends Bio-technol. 26:126-131.
6. Richardson J W, Johnson M D, Outlaw J L. 2012. Economic comparison of open pond raceways to photo bio-reactors for profitable production of algae for transportation fuels in the Southwest. Algal Res. 1:93-100.
7. Uduman N, Qi Y, Danquah M K, Forde G M, Hoadley A. 2010. Dewatering of microalgal cultures: a major bottleneck to algae-based fuels. J. Renewable Sustainable Energy 2:012701. http://dx.doi.org/10.1063/1.329 4480.
8. Sirin S, Trobajo R, Ibanez C, Salvado J. 2012. Harvesting the microalgae *Phaeodactylum tricornutum* with polyaluminum chloride, aluminium sulphate, chitosan and alkalinity-induced flocculation. J. Appl. Phycol. 24: 1067-1080.
9. Lavoie A, Noüe J. 1983. Harvesting microalgae with chitosan. J. World Maricult. Soc. 14:685-694.
10. Divakaran R, Sivasankara Pillai V. 2002. Flocculation of algae using chitosan. J. Appl. Phycol. 14:419-422.
11. Pavoni J L, Tenney M W, Echelberger W F, Jr. 1972. Bacterial exocellular polymers and biological flocculation. J. Water Pollut. Control Fed. 44: 414-429.
12. Yuan S J, Sun M, Sheng G P, Li Y, Li W W, Yao R S, Yu H Q. 2011. Identification of key constituents and structure of the extracellular polymeric substances excreted by *Bacillus megaterium* TF10 for their flocculation capacity. Environ. Sci. Technol. 45:1152-1157.
13. Nontembiso P, Sekelwa C, Leonard M V, Anthony O I. 2011. Assessment of bioflocculant production by *Bacillus* sp. Gilbert, a marine bacterium isolated from the bottom sediment of Algoa Bay. Mar. Drugs 9:1232-1242.
14. Gardes A, Iversen M H, Grossart H P, Passow U, Ullrich M S. 2011. Diatom-associated bacteria are required for aggregation of *Thalassiosira weissflogii*. ISME J. 5:436-445.
15. Oh H M, Lee S J, Park M H, Kim H S, Kim H C, Yoon J H, Kwon G S, Yoon B D. 2001. Harvesting of *Chlorella vulgaris* using a bioflocculant from *Paenibacillus* sp AM49. Biotechnol. Lett. 23:1229-1234.
16. Wang H, Laughinghouse H D T, Anderson M A, Chen F, Willliams E, Place A R, Zmora O, Zohar Y, Zheng T, Hill R T. 2012. Novel bacterial isolate from Permian groundwater, capable of aggregating potential biofuel-producing microalga *Nannochloropsis oceanica* IMET1. Appl. Environ. Microbiol. 78:1445-1453.
17. Yoon J H, Oh H M, Yoon B D, Kang K H, Park Y H. 2003. *Paenibacillus kribbensis* sp. nov. and *Paenibacillus terse* sp. nov., bioflocculants for efficient harvesting of algal cells. Int. J. Syst. Evol. Microbiol. 53:295-301.
18. Guillard R R L. 1975. Culture of phytoplankton for feeding marine invertebrates, p 29-60. In Culture of marine invertebrate animals. Plenum, New York, N.Y.
19. Lane D. 1991. 16S/23S rRNA sequencing, p 115-147. In Stackebrandt E, Goodfellow M (ed), Nucleic acid techniques in bacterial systematics. John Wiley & Sons, Inc., New York, N.Y.
20. Lee J, Cho D H, Ramanan R, Kim B H, Oh H M, Kim H S. 2013. Microalgae-associated bacteria play a key role in the flocculation of *Chlorella vulgaris*. Bioresour. Technol. 131:195-201.
21. Marquis R E, Mayzel K, Carstensen E L. 1976. Cation exchange in cell walls of gram-positive bacteria. Can. J. Microbiol. 22:975-982.
22. Dubinsky Z, Rotem J. 1974. Relations between algal populations and the pH of their media. Oecologia 16:53-60.
23. Schlesinger A, Eisenstadt D, Bar-Gil A, Carmely H, Einbinder S, Gressel J. 2012. Inexpensive non-toxic floc- 24. Waltz, E. 2009. Biotech's green gold? Nat. Biotechnol. 27:15-18.
25. Chisti, Y. 2008. Biodiesel from microalgae beats bio-ethanol. Trends Biotechnol. 26:126-131.
26. Schenk, P. M., S. R. Thomas-Hall, E. Stephens, U. C. Marx, J. H. Mussgnug, C. Posten, O. Kruse, and B. Hankamer. 2008. Second generation biofuels: high-efficiency microalgae for biodiesel production. Bioenerg. Res. 1:20-43.
27. Biddy, M., R. Davis, S. Jones, and Y. Zhu. 2013. Whole algae hydrothermal liquefaction technology pathway. Pacific Northwest National Laboratory (PNNL), Richland, Wash. (US). http://www.nrel.gov/docs/fy13osti/58051.pdf
28. Richardson, J. W., M. D. Johnson, and J. L. Outlaw. 2012. Economic comparison of open pond raceways to photo bio-reactors for profitable production of algae for transportation fuels in the Southwest. Algal Research 1:93-100.
29. Uduman, N., Y. Qi, M. K. Danquah, G. M. Forde, and A. Hoadley. 2010. Dewatering of microalgal cultures: A major bottleneck to algae-based fuels. J. Renew. Sustain. Ener. 2:017201.
30. Sirin, S., R. Trobajo, C. Ibanez, and J. Salvado. 2012. Harvesting the microalgae *Phaeodactylum tricornutum* with polyaluminum chloride, aluminium sulphate, chitosan and alkalinity-induced flocculation. J. Appl. Phycol. 24:1067-1080.
31. Lavoie, A., and J. Noüe. 1983. Harvesting microalgae with chitosan. J. World Maricult. Soc. 14:685-694.
32. Divakaran, R., and V. Sivasankara Pillai. 2002. Flocculation of algae using chitosan. J. Appl. Phycol. 14:419-422.
33. Pavoni, J. L., Echelber. W f, and M. W. Tenney. 1972. Bacterial exocellular polymers and biological flocculation. J. Water Pollut. Con. F 44:414-&.
34. Yuan, S. J., M. Sun, G. P. Sheng, Y. Li, W. W. Li, R. S. Yao, and H. Q. Yu. 2011. Identification of key constituents and structure of the extracellular polymeric substances excreted by *Bacillus megaterium* TF10 for their flocculation capacity. Environ. Sci. Technol. 45:1152-1157.
35. Nontembiso, P., C. Sekelwa, M. V. Leonard, and O. I. Anthony. 2011. Assessment of bioflocculant production by *Bacillus* sp. Gilbert, a marine bacterium isolated from the bottom sediment of Algoa Bay. Mar. Drugs 9:1232-1242.
36. Gardes, A., M. H. Iversen, H. P. Grossart, U. Passow, and M. S. Ullrich. 2011. Diatom-associated bacteria are required for aggregation of *Thalassiosira weissflogii*. Isme J. 5:436-445.
37. Oh, H. M., S. J. Lee, M. H. Park, H. S. Kim, H. C. Kim, J. H. Yoon, G. S. Kwon, and B. D. Yoon. 2001. Harvesting of *Chlorella vulgaris* using a bioflocculant from *Paenibacillus* sp AM49. Biotechnol. Lett. 23:1229-1234.
38. Wang, H., H. D. T. Laughinghouse, M. A. Anderson, F. Chen, E. Willliams, A. R. Place, O. Zmora, Y. Zohar, T. Zheng, and R. T. Hill. 2012. Novel bacterial isolate from Permian groundwater, capable of aggregating potential biofuel-producing microalga *Nannochloropsis oceanica* IMET1. Appl. Environ. Microbiol. 78:1445-1453.
39. Yoon, J. H., H. M. Oh, B. D. Yoon, K. H. Kang, and Y. H. Park. 2003. *Paenibacillus kribbensis* sp nov and *Paenibacillus terrae* sp nov., bioflocculants for efficient harvesting of algal cells. Int. J. Syst. Evol. Micr. 53:295-301.
40. Powell, R. J., and R. T. Hill. 2013. Rapid aggregation of biofuel-producing algae by the bacterium *bacillus* sp. strain RP1137. Appl. Environ. Microbiol. 79:6093-6101.
41. Guillard, R. R. L. 1975. Culture of phytoplankton for feeding marine invertebrates. Culture of marine invertebrate animals. Plenum: 29-60.
42. Kamentsky, L., T. R. Jones, A. Fraser, M. A. Bray, D. J. Logan, K. L. Madden, V. Ljosa, C. Rueden, K. W. Eliceiri, and A. E. Carpenter. 2011. Improved structure, function and compatibility for CellProfiler: modular high-throughput image analysis software. Bioinformatics 27:1179-1180.
43. Lortal, S., J. Vanheijenoort, K. Gruber, and U. B. Sleytr. 1992. S-Layer of *Lactobacillus*-Helveticus Atcc-12046—Isolation, chemical characterization and reformation after extraction with lithium-chloride. J. Gen. Microbiol. 138:611-618.
44. Sabarth, N., R. Hurvitz, M. Schmidt, U. Zimny-Arndt, P. R. Jungblut, T. F. Meyer, and D. Bumann. 2005. Identification of *Helicobacter pylori* surface proteins by selective proteinase K digestion and antibody phage display. J. Microbiol. Meth. 62:345-349.
45. Garrote, G. L., L. Delfederico, R. Bibiloni, A. G. Abraham, P. F. Perez, L. Semorile, and G. L. De Antoni. 2004. Lactobacilli isolated from kefir grains: evidence of the presence of S-layer proteins. J. Dairy Res. 71:222-230.
46. Hermansson, M. 1999. The DLVO theory in microbial adhesion. Colloid Surface B 14:105-119.
47. Sobeck, D. C., and M. J. Higgins. 2002. Examination of three theories for mechanisms of cation-induced bioflocculation. Wat. Res. 36:527-538.
48. Marquis, R. E., K. Mayzel, and E. L. Carstensen. 1976. Cation exchange in cell walls of gram-positive bacteria. Can. J. Microbiol. 22:975-982.
49. Pal, M. K., T. C. Ghosh, and J. K. Ghosh. 1990. Studies on the conformation of and metal ion binding by teichoic acid of *Staphylococcus aureus*. Biopolymers 30:273-277.
50. Lee, J., D. H. Cho, R. Ramanan, B. H. Kim, H. M. Oh, and H. S. Kim. 2013. Microalgae-associated bacteria play a key role in the flocculation of *Chlorella vulgaris*. Bioresour. Technol. 131:195-201.
51. Schlesinger, A., D. Eisenstadt, A. Bar-Gil, H. Carmely, S. Einbinder, and J. Gressel. 2012. Inexpensive non-toxic flocculation of microalgae contradicts theories; overcoming a major hurdle to bulk algal production. Biotechnol. Adv. 30:1023-1030.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed is:

1. A method for collecting algae, comprising binding algae in a culture to bare maghemite and forming an algae aggregate, wherein the culture is at a pH of 1-9 and the binding of algae to bare maghemite is not pH sensitive and is not reversible by altering the pH.

2. The method of claim 1, wherein the bare maghemite is produced by heating magnetite powder, and oxidizing the magnetite to form maghemite.

3. The method of claim 1, wherein the bare maghemite has an average particle diameter by mass (D50) of greater than 10 μm to 500 μm.

4. The method of claim 1, wherein the bare maghemite has an average particle diameter by mass (D50) of 1 nm to 1 μm.

5. The method of claim 1, wherein the culture is an artificial medium or fresh, brackish or salt water.

6. The method of claim 1, wherein the culture is a closed culture or an open culture.

7. The method of claim 1, wherein the culture is an open culture that is a pond, a lake, a bay, coastal waters, or an ocean.

8. The method of claim 1, wherein the culture is at a pH of 4-9.

* * * * *